(12) United States Patent
Penders et al.

(10) Patent No.: US 11,534,104 B2
(45) Date of Patent: Dec. 27, 2022

(54) SYSTEMS AND METHODS FOR CONTRACTION MONITORING AND LABOR DETECTION

(71) Applicant: Bloom Technologies NV, Genk (BE)

(72) Inventors: Julien Penders, San Francisco, CA (US); Michiel Rooijakkers, Eindhoven (NL); Marco Altini, San Francisco, CA (US); Eric Dy, San Francisco, CA (US)

(73) Assignee: BLOOM TECHNOLOGIES NV, Genk (BE)

( * ) Notice: Subject to any disclaimer, the term of this patent is extended or adjusted under 35 U.S.C. 154(b) by 504 days.

(21) Appl. No.: 16/665,569

(22) Filed: Oct. 28, 2019

(65) Prior Publication Data

US 2020/0107771 A1 Apr. 9, 2020

Related U.S. Application Data

(63) Continuation-in-part of application No. 15/523,072, filed as application No. PCT/US2015/058153 on Oct.
(Continued)

(30) Foreign Application Priority Data

Feb. 2, 2015 (BE) .................................. 2015/5056

(51) Int. Cl.
*A61B 5/00* (2006.01)
*G06N 20/00* (2019.01)
*A61B 5/024* (2006.01)

(52) U.S. Cl.
CPC .......... *A61B 5/4356* (2013.01); *A61B 5/0011* (2013.01); *A61B 5/024* (2013.01);
(Continued)

(58) Field of Classification Search
CPC ..... A61B 5/4356; A61B 5/0011; A61B 5/024; A61B 5/6833; A61B 5/7264;
(Continued)

(56) References Cited

U.S. PATENT DOCUMENTS 5,042,503 A 8/1991 Torok et al.
5,623,939 A 4/1997 Garfield et al.
(Continued)

FOREIGN PATENT DOCUMENTS

CA 2608497 A1 8/2006
CA 2754721 A1 9/2010
(Continued)

OTHER PUBLICATIONS

NS Medical "Philips secures CE mark for new Avalon obstetrical care solution" NS Medical Devices. Sep. 14, 2018. <https://www.nsmedicaldevices.com/news/philips-ce-mark-avalon/> (Year: 2018).*
(Continued)

*Primary Examiner* — David J. McCrosky
(74) *Attorney, Agent, or Firm* — Aurora Consulting LLC; Kristen J. Hansen; Ashley Sloat

(57) ABSTRACT

Described herein are methods for identifying a labor state in a pregnant female, including: receiving an input indicating a gestational age; acquiring a physiological signal; processing the physiological signal to extract a parameter of interest; and feeding the parameter of interest into a machine learning model. The machine learning model is configured to: determine a first labor probability based on the parameter of interest, determine a second labor probability based on the parameter of interest or a second parameter of interest and the gestational age, and classify the labor state of the pregnant female based on the first and second labor probability.

20 Claims, 34 Drawing Sheets

Related U.S. Application Data 29, 2015, now Pat. No. 10,456,074, application No. 16/665,569, which is a continuation-in-part of application No. 15/429,215, filed on Feb. 10, 2017, now abandoned.

(60) Provisional application No. 62/293,714, filed on Feb. 10, 2016, provisional application No. 62/072,348, filed on Oct. 29, 2014.

(52) U.S. Cl.
CPC .......... *A61B 5/6833* (2013.01); *A61B 5/7264* (2013.01); *G06N 20/00* (2019.01)

(58) Field of Classification Search
CPC ...... A61B 5/7275; G06N 20/00; G06N 5/046; G06N 7/005; G16H 50/20; G16H 50/70; G16H 40/60; G16H 40/63; G16H 40/67
See application file for complete search history.

(56) References Cited

U.S. PATENT DOCUMENTS

| | | |
|---|---|---|
| 5,776,073 A | 7/1998 | Garfield et al. |
| 5,954,663 A | 9/1999 | Gat |
| 6,134,466 A | 10/2000 | Rosenberg |
| 6,816,744 B2 | 11/2004 | Garfield et al. |
| 7,532,923 B1 | 5/2009 | Hayes-Gill et al. |
| 8,116,855 B2 | 2/2012 | James et al. |
| 8,229,550 B2 | 7/2012 | James et al. |
| 8,255,238 B2 | 8/2012 | Powell et al. |
| D717,674 S | 11/2014 | Vu et al. |
| 8,880,140 B2 | 11/2014 | Hayes-Gill et al. |
| D739,284 S | 9/2015 | Vu et al. |
| D739,775 S | 9/2015 | Vu et al. |
| D739,776 S | 9/2015 | Vu et al. |
| D739,777 S | 9/2015 | Vu et al. |
| D739,778 S | 9/2015 | Vu et al. |
| D740,706 S | 10/2015 | Vu et al. |
| D743,819 S | 11/2015 | Golnik et al. |
| D752,764 S | 3/2016 | Peters |
| 9,307,923 B2 | 4/2016 | Peters et al. |
| 9,314,203 B2 | 4/2016 | Peters |
| 9,392,952 B1 | 7/2016 | Oz et al. |
| 9,572,504 B2 | 2/2017 | Oz et al. |
| D781,568 S | 3/2017 | Workman |
| 9,642,544 B2 | 5/2017 | Oz et al. |
| 9,713,430 B2 | 7/2017 | Oz et al. |
| 9,717,412 B2 | 8/2017 | Roham et al. |
| 9,763,583 B2 | 9/2017 | Oz et al. |
| 9,999,367 B2 | 6/2018 | Vullings et al. |
| 10,064,566 B2 | 9/2018 | Atallah et al. |
| 11,324,437 B2 | 5/2022 | Mhajna |
| 2003/0004403 A1 | 1/2003 | Drinan et al. |
| 2004/0087840 A1 | 5/2004 | Main |
| 2005/0267376 A1 | 12/2005 | Marossero et al. |
| 2007/0191728 A1 | 8/2007 | Shennib |
| 2007/0255184 A1 | 11/2007 | Shennib |
| 2007/0260133 A1 | 11/2007 | Meyer |
| 2008/0029333 A1 | 2/2008 | Oz |
| 2008/0275316 A1 | 11/2008 | Fink et al. |
| 2009/0036787 A1 | 2/2009 | James et al. |
| 2009/0143650 A1 | 6/2009 | Guion-Johnson et al. |
| 2009/0192396 A1 | 7/2009 | Hayes-Gill et al. |
| 2009/0299212 A1 | 12/2009 | Principe et al. |
| 2010/0211594 A1 | 8/2010 | Penders et al. |
| 2010/0235782 A1 | 9/2010 | Powell et al. |
| 2010/0274145 A1 | 10/2010 | Tupin, Jr. et al. |
| 2011/0190652 A1 | 8/2011 | Fink et al. |
| 2011/0237972 A1 | 9/2011 | Garfield et al. |
| 2011/0251512 A1 | 10/2011 | Fink et al. |
| 2011/0251817 A1 | 10/2011 | Burns et al. |
| 2011/0270118 A1 | 11/2011 | Garfield et al. |
| 2011/0306893 A1 | 12/2011 | Harrold et al. |
| 2012/0075103 A1 | 3/2012 | Powell et al. |
| 2012/0150010 A1 | 6/2012 | Hayes-Gill et al. |
| 2012/0232398 A1 | 9/2012 | Roham et al. |
| 2012/0265090 A1 | 10/2012 | Fink et al. |
| 2012/0289789 A1 | 11/2012 | Jain et al. |
| 2013/0006132 A1 | 1/2013 | Brody et al. |
| 2013/0030831 A1 | 1/2013 | Powell et al. |
| 2013/0090538 A1 | 4/2013 | Garfield et al. |
| 2013/0275152 A1 | 10/2013 | Moore et al. |
| 2014/0180169 A1 | 6/2014 | Peters et al. |
| 2014/0249436 A1 | 9/2014 | Serguei et al. |
| 2015/0004912 A1 | 1/2015 | Diamond et al. |
| 2015/0022366 A1 | 1/2015 | Vu et al. |
| 2015/0105646 A1 | 4/2015 | Peters |
| 2015/0374328 A1 | 12/2015 | Ginestet et al. |
| 2016/0015315 A1 | 1/2016 | Auphan et al. |
| 2016/0058363 A1 | 3/2016 | Hayes-Gill et al. |
| 2016/0066827 A1 | 3/2016 | Workman et al. |
| 2016/0103590 A1 | 4/2016 | Vu et al. |
| 2016/0157717 A1 | 6/2016 | Gaster et al. |
| 2016/0256132 A1 | 9/2016 | VandeLaar et al. |
| 2016/0262649 A1 | 9/2016 | Hayes-Gill et al. |
| 2016/0262687 A1 | 9/2016 | Vaidyanathan |
| 2016/0331299 A1 | 11/2016 | Cline |
| 2019/0200916 A1 | 7/2019 | Hyde et al. |
| 2020/0085365 A1 | 3/2020 | McDonald et al. |
| 2020/0146614 A1 | 5/2020 | Cline et al. |
| 2020/0155027 A1 | 5/2020 | Lau et al. |
| 2020/0214618 A1 | 7/2020 | Vullings |
| 2022/0167911 A1 | 6/2022 | Brooker |

FOREIGN PATENT DOCUMENTS

| | | |
|---|---|---|
| CA | 2765124 A1 | 12/2010 |
| CA | 2870560 A1 | 10/2013 |
| EP | 1220640 B1 | 5/2008 |
| EP | 1941830 A2 | 7/2008 |
| EP | 1941832 A1 | 7/2008 |
| EP | 1680018 B1 | 11/2008 |
| EP | 2451345 A2 | 1/2011 |
| EP | 1952760 B1 | 4/2012 |
| EP | 2745774 A1 | 6/2014 |
| EP | 3011464 A1 | 12/2014 |
| EP | 2862511 A1 | 4/2015 |
| EP | 2328471 B1 | 9/2015 |
| EP | 2997892 A1 | 3/2016 |
| EP | 2185068 B1 | 9/2016 |
| WO | 2005110236 A1 | 11/2005 |
| WO | 2009013245 A1 | 1/2009 |
| WO | 2009150440 A1 | 12/2009 |
| WO | 2010105063 A1 | 9/2010 |
| WO | 2010144413 A1 | 12/2010 |
| WO | 2011004147 A2 | 1/2011 |
| WO | 2011094609 A2 | 8/2011 |
| WO | 2011119757 A2 | 9/2011 |
| WO | 2011130291 A2 | 10/2011 |
| WO | 2011130295 A2 | 10/2011 |
| WO | 2012061827 A1 | 5/2012 |
| WO | 2012131171 A1 | 10/2012 |
| WO | 2012142241 A2 | 10/2012 |
| WO | 2013052612 A2 | 4/2013 |
| WO | 2013158625 A1 | 10/2013 |
| WO | 2014035836 A1 | 3/2014 |
| WO | 2014162135 A1 | 10/2014 |
| WO | 2014205201 A1 | 12/2014 |
| WO | 2015013163 A1 | 1/2015 |
| WO | 2015020886 A1 | 2/2015 |
| WO | 2015056027 A1 | 4/2015 |
| WO | 2015063520 A1 | 5/2015 |
| WO | 2016131630 A1 | 8/2016 |

OTHER PUBLICATIONS

Jo, Young Chang, et al. "Wearable patch device for uterine EMG and preterm birth monitoring applications." TENCON 2018-2018 IEEE Region 10 Conference. IEEE, 2018. (Year: 2018).*

Hodsen, S. "GE Healthcare Expands Digital Offerings With Maternal-Infant Monitoring Acquisition" Med Device Online. Mar. 16, 2017

(56) References Cited

OTHER PUBLICATIONS

<https://www.meddeviceonline.com/doc/ge-healthcare-expands-digital-offerings-with-maternal-infant-monitoring-acquisition-0001> (Year: 2017).*

Internet Archive, Bloomlife.com, "How Bloomlife Works" Sep. 25, 2018. <https://web.archive.org/web/20180925151005/http://www.bloomlife.com/how-it-works/> (Year: 2018).*

Bakris, "A practical approach to achieving recommended blood pressure goals in diabetic patients", Archives of Internal Medicine, vol. 161, Issue 22, 2001, pp. 2661-2667.

Faurholt-Jepsen, et al., "Electronic monitoring of psychomotor activity as a supplementary objective measure of depression severity", Nordic Journal of Psychiatry, vol. 69.

Haakstad et al., "Stages of change model for participations in physical activity during pregnancy", Journal of Pregnancy, vol. 2013, 2013, 7 pgs.

Hjortskov, et al., "The effect of mental stress on heart rate variability and blood pressure during computer work", European Journal of Applied Physiology, vol. 92, Issue 1.

Intille, S., "Ubiquitous Computing Technology for Just-In-Time Motivation of Behavior Change", Studies in Health Technology and Informatics, vol. 107, 2004, pp. 1434-1437.

Kenny, et al., "Novel biomarkers for pre-edampsia detected using metabolomics and machine learning", Metabolomics, vol. 1, Issue 3, 2005, pp. 227-234.

Lathia et al., "Smart phones for large-scale behavior change interventions", Proceedings of IEEE Pervasive Computing, 2013, pp. 2-9.

MacMahon, et al., Blood pressure, stroke, and coronary heart disease: part 1, prolonged differences in blood pressure: prospective observational studies corrected for the reg.

Moriya, et al., "Weekly averaged blood pressure is more important than a single-point blood pressure measurement in the risk stratification of dialysis patients", Clinical Jou.

Pickering, et al., "Ambulatory Blood-Pressure Monitoring", New England Journal of Medicine, vol. 354, 2006, pp. 2368-2374.

Rodriquez-Roisin, "Toward a Consensus Definition for COPD Exacerbations", Chest, vol. 117, issue 5, Suppl 2, 2000, pp. 398S-401S.

Salah et al., "Human Behavior Understanding tor Inducing Behavioral Change: Application Perspectives", Human Behavior Understanding, Lecture Notes in Computer Science, Volume.

Woolf, S.H., "The power of prevention and what it requires", Journal of the American Medical Association, vol. 299, 2008, pp. 2437-2439.

Zhou et al., "Getting Clinicians Involved: Testing Smartphone Applications to Promote Behavior Change in Health Care", May 31, 2012, Retrieved from Internet: URL:http://citenpl.

Dovetail Care, "Pregnansi", SimilarWeb Ltd, 2016, 7 pages.

Shulgin et al., "Electrohysterographic Signals Processing for Uterine Activity Detection ad Characterization", IEEE XXXIV International Scientific Conference Electronics and Nanotechnology, 2014, pp. 269-272.

Horoba, et al., "Statistical Approach to Analysis of Electrohysterographic Signal", Proceedings of the First Joint BMES/EMBS Conference, Atlanta, GA, 1999, pp. 887.

International Search Report dated Dec. 24, 2014 from International Application PCT/US2014/049280, 4 pgs.

Written Opinion of International Search Report dated Dec. 24, 2014 from International Application PCT/JS2014/049280, 15 pgs.

De Lau Hinke et al., "Towards improving uterine electrical activity modeling and electrohysterography: ultrasonic quantification of uterine movements during labor.", Nordic Federation of Societies of Obstetrics and Gynecology, Acta Obstetricia et Gynecologica Scandinavica, 2013, 1323-1326, 92 (11).

Zimmer et al., "The relationship between uterine contractions, fetal movements and fetal heart rate patterns in the active phase of labor", Elsevier Science Publishers B.V. (Biomedical Division), 1987, 89-95, 25 (2).

International Search Report dated May 6, 2016 from International Application PCT/IB2015/002194, 7 pgs.

Written Opinion of International Search Report dated May 6, 2016 from International Application PCT/IB2015/002194, 11 pgs.

European Search Report and Written Opinon of European Search Report for Belgium National Application BE201505056, 18 pgs.

Supplementary European Search Report dated Feb. 17, 2017 for EP 14834450.0, 7 pgs.

Written Opinion of International Search Report dated Dec. 19, 2018 from International Application PCT/IB2018/055394, 12 pgs.

International Search Report dated Dec. 19, 2018 from International Application PCT/IB2018/055394, 8 pgs.

Lange, L. et al. "Velocity and Directionality of the Electrohysterographic Signal Propagation," Plos One, vol. 9, No. 1, Jan. 21, 2014, pp. 1-6.

Maner, W. et al. "Identification of Human Term and Preterm Labor using Artificial Neural Networks on Uterine Electromyography Data," Annuals of Biomedical Engineering, Kluwer Academic Publishers-Plem Publishers, NE, vol. 35, No. 3, Jan. 17, 2007, pp. 465-473.

Penders, J. et al. "Wearable Sensors for Healthier Pregnancies," IEEE, Proceedings of the IEEE, 2015, http://www.ieee.org/publications_standards/publications/rights/index.html.

* cited by examiner

SYSTEMS AND METHODS FOR CONTRACTION MONITORING AND LABOR DETECTION

CROSS-REFERENCE TO RELATED APPLICATIONS

This application is a continuation-in-part of U.S. patent application Ser. No. 15/429,215, titled "Systems and Methods for Detecting a Labor Condition," filed Feb. 10, 2017, which claims the priority benefit of U.S. Provisional Patent Application Ser. No. 62/293,714, entitled "Systems and Methods for Detecting a Labor Condition," filed Feb. 10, 2016, the disclosure of which is hereby incorporated by reference in its entirety.

This application is also a continuation-in-part of U.S. patent application Ser. No. 15/523,072, titled "A Method and Device for Contraction Monitoring," filed Apr. 28, 2017, which is the U.S. National Stage filing for PCT Application Ser. No. PCT/US2015/058153, now published as WO/2016/067101, titled "A Method and Device for Contraction Monitoring," filed Oct. 29, 2015, which claims priority benefits to U.S. provisional patent application Ser. No. 62/072,348, titled "Method and Device for Contraction Monitoring", filed on Oct. 29, 2014 and foreign priority benefits to Belgium patent application No. BE2015/5056, titled "Method and Apparatus for Monitoring Contractions in Pregnancy", filed on Feb. 5, 2015, each of which are herein incorporated by reference in their entireties.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This invention relates generally to the field of obstetrics and gynecology, and more specifically to new and useful systems and methods for pregnancy monitoring, contraction monitoring, and detecting and characterizing labor.

BACKGROUND

Pregnant women are full of questions about their pregnancy, their bodies, and their babies. One of the most stressful questions for late term women is am I having contractions? Answering this question is key to understand when labor is starting, allowing a pregnant couple to prepare for the imminent delivery and eventually leave, in a timely manner, for the hospital or the care institution where the delivery will happen. During the second and third trimester already, women may experience early contractions, also referred to as Braxton Hicks contractions. Braxton Hicks contractions are the manifestation that the uterus is slowly preparing for the delivery. The feeling of a contraction is completely new and it is impossible for a woman to reliably identify a contraction from other abdominal physiological disturbances such as abdominal cramps or bowel disturbances. This is especially true for first time moms, but second and third time moms also report this problem, as they would often forget what a contraction feels like.

Next to pregnant women, clinicians have a vast interest in monitoring contractions. History of contractions is part of the clinical examination in most countries, and an obstetrician will typically ask her pregnant patient whether she has had contractions since her last visit, and how often. The answer to this question is inevitably inaccurate since a woman is not able to reliably report contractions.

Despite the importance of monitoring contractions outside the hospital or physician's office, from both a consumer and clinician perspective, there is to date no solution available for contraction monitoring outside controlled clinical settings. The best alternative solution available today for consumers is a stopwatch, analog or digital. Stopwatches rely on the woman's perception and feeling of a contraction and are therefore intrinsically inaccurate and do not address the problem that women cannot recognize or detect their contractions.

In a healthcare setting, uterine contraction activity is commonly monitored using a tocograph or uterine pressure catheter. Such devices mechanically sense pressure changes caused by uterine contractions. The tocograph is strapped to a woman's midsection using a belt, and the pressure transducer is pressed against the woman's abdomen. The device is large and obtrusive and requires a woman to stay next to the bulky equipment, thus limiting her mobility once attached. Moreover, the device requires careful positioning in order to get a reliable measurement. As a consequence, the tocograph must be operated by a trained clinician. The uterine pressure catheter includes an intrauterine pressure sensor attached to a catheter; the device is inserted into a woman's uterus via the birth canal in order to detect changes in uterine pressure that occur during a contraction. Thus, the device is fairly intrusive and also must be operated by a trained clinician. Both tocography and intrauterine pressure catheters measure the change in pressure that results from a contraction rather than the physiological phenomena leading to the contraction. As a result, their accuracy in characterizing contractions, especially the intensity of contractions, is not high.

Physiologically, the contraction originates with the electrical activation of uterine cells, similar to the activation of muscle cells. Measuring the uterine electrical activity is a more accurate and more reliable way of measuring contractions called electrohysterography (EHG). US2012/0150010-A1 describes a device and method for monitoring uterine activity based on EHG. However, such devices are today limited to bulky devices with electrodes and wires, operated by clinically experienced staff, and limited to the clinical environment. Attempts have already been made to improve the ease of use and the bulkiness of such devices. US2007/0255184-A1 discloses a disposable labor detection patch using electromyogram signals of the uterus. However, such a concept of a disposable patch integrating all the electronics will inevitably be associated with a very high cost due to the cost of the electronic components, hindering is practicality and usability as a disposable system. Although the electrode part of the system needs to be often replaced for hygiene and signal quality reasons, the electronics can be used for hundreds or thousands of recordings without the need to be dispose or replace it. Furthermore, although a patch may be applicable for some pregnant women, attaching an adhesive on the abdomen of a pregnant women often will be considered uncomfortable as it may lead to itching sensations, irritations, allergies or other disturbances. For such cases, considering other form factors than a patch would be advantageous.

Furthermore, the devices of US2012/0150010-A1 and US2007/0255184-A1 are limited in their functionality. These devices merely provide a measurement of the contraction signal, and do not perform any further analysis on the signal. As a result, they are of limited value to the user directly but require the intervention of a clinically experienced staff to interpret the results.

Electrodes placed on the abdomen of a pregnant woman are capable of measuring bio-potential signals that comprise various electrical signals generated by the body such as the maternal electro-cardiogram (mECG), the fetal electro-cardiogram (fECG) as well as the uterine electrohysterogram (EHG) and uterine electromyogram (UEMG) which is equivalent to the electrical signature of the uterine muscle contraction. The electrohysterogram can be seen as a high-level view of the uterine electrical activity, looking at the slower waves that are generated by the common activation of a larger number of uterine cells.

Complementarily, the uterine electromyogram (UEMG) can be seen as a fine view on the uterine electrical activity, looking at the fast-paced electrical waves generated locally by smaller sets of uterine cells. EHG signals are usually analyzed in the time domain, using RMS, linear filters or other statistics, to come to an estimation of a contraction signal. UEMG signals are usually analyzed in the time frequency domain using Fourier transforms, wavelet transforms, etc. EHG and UEMG signals are superposed to the maternal and fetal electro-cardiogram. Signal processing techniques are also required to isolate every physiological contribution to the bio-potential signals.

All these signals are monitored during long periods of time in the hospital during labor or in the last months of the pregnancy for monitoring and need to be further analyzed by a care specialist. These signals are usually displayed on a screen or printed on a sheet of paper while the signals are being recorded.

Despite the existence of these technologies in the healthcare setting, pregnant women continue to face significant uncertainty outside of the healthcare setting when trying to determine whether contractions they experience are true labor contractions and whether it is an appropriate or necessary time to seek medical attention. The uncertainty pregnant women and their families face in deciphering whether a woman is, or soon will be, in labor causes significant anxiety and stress. The uncertainty may lead to over-utilization of the healthcare system due to false alarms. This may result in wasted time, wasted medical resources, and unnecessary medical costs. The uncertainty may alternatively cause women to wait too long to seek medical attention, resulting in unintentional deliveries outside of healthcare facilities. Delivering a child without a medical professional or birthing specialist present may increase the risk of complications to child and mother, eventually leading to increased risk of maternal and fetal death.

In view of the foregoing, a need exists in pregnancy monitoring for a device and a method for contraction monitoring that can be used by pregnant women in any environment, answering the most stressful questions that women have as they are progressing throughout pregnancy, while providing important clinical information that the healthcare practitioner can use during his clinical examination.

SUMMARY

These aims are achieved according to the embodiments of the invention. According to an aspect of the present invention, there is provided a contraction monitoring system comprising: an electrode patch comprising at least two electrodes, including a measurement electrode and a reference electrode, and a sensor module configured to be connected to the electrode patch, the sensor module comprising a signal acquisition module, a signal processing module, a power management module, a sensor control module and at least one of a memory module or a data transmission module, wherein the signal acquisition module is configured to perform a method comprising: measuring bio-potential signals by providing at least two electrodes on the abdomen of a pregnant woman; and the signal processing module is configured to perform a method comprising: processing the bio-potential signal to extract electrohysterogram signals, and processing the extracted signals to extract uterine contraction.

In an embodiment of the system according to the present invention, the method performed by the signal processing module further comprises processing the bio-potential signal to extract maternal electrocardiogram signals.

In another embodiment of the system according to the present invention, the method performed by the signal processing module further comprises processing the bio-potential signal to extract fetus electrocardiogram signals.

In a further embodiment of the system according to the present invention, the method performed by the signal processing module further comprises isolating from the electrohysterogram signals a part of the electrohysterogram signal that is relevant to the electrical activity of the uterus, and separating it out from the part of the electrohysterogram signal that is related to other physiological phenomena, noise, artifacts and any other contributions.

According to an embodiment of the present invention, the sensor module further comprises an inertial sensing module and the signal acquisition module further comprises acquiring inertial sensing module data.

In a specific embodiment, the method performed by the signal processing module further comprises processing the inertial sensing module data to extract uterine contraction signals.

Advantageously, the method performed by the signal processing module further comprises processing the inertial sensing module data to measure motion artifact and wherein processing the bio-potential signal to extract electrohysterogram signals, maternal electrocardiogram signals, and fetus electrocardiogram signals further comprises applying motion artifact filtering to at least one of the extracted signals based on the measured motion artifact.

In an embodiment of the present invention, artifacts are detected by advantageously combining electrohysterogram signals and inertial sensing module data. Motion artifacts are made up of broad spectrum frequency components and artifacts which affect the signal of interest will also be visible outside of the specific band of interest. In general, motion artifacts are characterized by a short-time high-energy peak over a wide spectral range of the bio-potential signals. Detection of artifacts in bio-potential signals can hence be performed by calculating the energy of the signal outside of the band of interest, and setting a moving threshold (TA) to detect the instances in which a motion artifact distorts the signal of interest. The threshold for artifact detection is dynamically changed based on the moving baseline energy in the frequency band used for artifact detection. This method has proven successful in detecting strong motion artifacts but is not sufficient in situations where the baseline energy level is high, or if the influence of the motion on the energy in the artifact detection band is low. In these cases, we can advantageously use of an inertial sensor to dynamically lower the threshold level during instances of increased motion of the sensor module. To this end, two features related to the rotational and translational energy of the inertial sensor are calculated and linearly combined as an indicator of the amount of sensor motion. When the amount of sensor motion exceeds a set minimum level (Lm), which can occur due to sensor noise of minor movements due to breathing, fetal movement, etc., the threshold TA, used to detect motion artifacts in the bio-potential signal, is lowered. The amount by which the threshold TA is lowered depends on the amount by which the sensor motion energy (Em) exceeds the minimum level Lm. This way, the motion energy Em can temporarily increase the sensitivity of the system in the detection of motion artifacts. Furthermore, as sharp motions often result in residual artifacts after the actual motion has subsided, a first order IIR filter is used to slowly return the threshold TA to its original value.

In an embodiment of the present invention, the method performed by the signal processing module further comprises: processing bio-potential signal to extract uterine electromyogram (UEMG) signals, processing the UEMG signals to extract UEMG markers, and classifying the bio-potential signals into contraction types based on the UEMG markers.

In one embodiment, UEMG markers comprise statistical features, such as at least one of average, mean, percentiles, standard deviation, kurtosis, any other statistical moments, power spectrum features such as at least one of total power in the bandwidth, peak power, mean power, average power, power in certain frequency bands, entropy features and spatial propagation features such as at least one of laplacian, gradient, and higher order propagation features to indicate the rate, the pattern and the spatial distribution of the firing of the uterine contractile cells.

According to another embodiment of the present invention, the method performed by the signal processing module further comprises analyzing the uterine contraction signals to compute uterine contraction statistics.

In one embodiment of the present invention, the sensor module further comprises an inertial sensing module and/or is configured to interact with an activity sensor provided by another device, and wherein the method performed by the signal processing module further comprises: measuring maternal activity, and correlating maternal activity with uterine contraction signals and/or uterine contraction statistics.

According to a further embodiment of the present invention, processing the individual signals to extract uterine contraction signals further comprises processing the mECG signals to extract a maternal heart rate (mHR) and maternal heart rate variation (mHRV), processing mHR and mHRV to extract maternal stress level, and correlating contractions with maternal stress level.

In an embodiment of the system according to the present invention, the method performed by the signal processing module further comprises providing user feedback.

According to another embodiment of the present invention, the method performed by the signal processing module further comprises processing the fECG signals to extract a fetal heart rate (fHR) and fetal heart rate variation (fHRV), and correlating contractions with fetal fHR and/or fHRV.

Advantageously, the method performed by the signal processing module further comprises extracting a position and movement of the fetus from the fECG, and measuring fetal activity from the position and movement of the fetus.

In some embodiments, the method performed by the signal processing module further comprises measuring fetal activity with the inertial sensing module.

According to an embodiment of the present invention, the method performed by the signal processing module further comprises correlating uterine contraction signals and/or uterine contraction statistics with fetal activity.

In one embodiment, the electrode patch further comprises a bias electrode and a second measurement electrode, wherein the first and second measurement electrodes are located on the two extremities of the electrode patch, and wherein the reference electrode is located substantially in the middle of the electrode patch.

In another embodiment, the electrode patch further comprises a third measurement electrode, wherein the first and second measurement electrode and the reference electrode are positioned substantially on a line, and wherein the third measurement electrode is positioned below the reference electrode substantially perpendicular to the line.

According to another aspect of the present invention, there is provided an electrode patch for use in the system as described above, comprising a bias electrode, three measurement electrodes and a reference electrode, wherein the first and second measurement electrodes and the reference electrode are positioned substantially on a line, wherein the third measurement electrode is positioned below the reference electrode substantially perpendicular to the line.

According to another aspect of the present invention, there is provided a sensor module for use in the system as described above, configured to connect to the electrode patch described in the present patent application, comprising the signal acquisition module, the signal processing module, the power management module, the sensor control module and at least one of the memory module or the data transmission module.

It is a further aspect of the present invention to provide a contraction monitoring device for use in the system disclosed in this application, comprising an electrode patch and a sensor module configured to communicate with a user personal device configured to perform parts of the functions carried out by the signal processing module and/or by the signal acquisition module of the sensor module.

Advantageously, functions carried out by the user personal device further comprise using context information coming from the user personal device to improve the accuracy and reliability of the user's uterine contraction activity estimation, maternal activity estimation, maternal stress estimation, fetal HR/HRV estimation, fetal movement estimation, fetal position estimation, and providing feedback to the user according to the measured parameters and estimated information to improve lifestyle and reduce risks related to pregnancy.

In an embodiment, a method for monitoring contractions is provided which comprises: (a) measuring bio-potential signals by providing at least two electrodes on the abdomen of a pregnant woman, (b) processing the bio-potential signals to extract EHG signals, (c) processing the EHG signals to extract uterine contraction signals, and (d) analyzing the uterine contraction signals to compute uterine contraction statistics.

This method allows the measurement of various types of bio-potential signals that carry information about the uterine activity of the pregnant woman Each bio-potential signal can be processed and provides specific information related to the uterine activity of the pregnant woman Combining the information corresponding to each type of bio-potential signal results in a more precise analysis of the uterine activity of the pregnant woman and allows a better and more precise diagnosis. Thanks to the uterine contraction statistics performed at step d) using the various contraction signals, this diagnosis is performed automatically by the method and no care specialist is required to interpret the various signals acquired. The uterine statistics computed are used to inform or alert the pregnant woman of the current status of her pregnancy and when she may need to go to the hospital. Such a device can therefore minimize risks of miscarriage, pre-term birth, and any complications related to pregnancy. Thanks to the method, the pregnant woman can be aware at all times of the current status of her pregnancy.

In embodiments of the invention, the processing of bio-potential signals comprises isolating and separating a part of the bio-potential signals that is relevant to the electrical activity of the uterus.

In embodiments of the invention, step b) comprises applying a filter having a bandpass of 0.3 Hz to 0.8 Hz to the biopotential signals.

In embodiments of the invention, the measured bio-potential signals comprise electrohysterogram signals, uterine electromyogram signals, material electrocardiogram signals, and fetus electrocardiogram signals.

In embodiments of the invention, measuring bio-potential signals comprises providing at least three electrodes on the abdomen of the pregnant woman, wherein the third electrode is used as a bias electrode or third leg electrode.

In embodiments of the invention, measuring bio-potential signals comprises three measurement electrodes, one reference electrode, and one bias electrode.

In embodiments of the invention, the reference electrode is positioned slightly under the navel.

In embodiments of the invention, the three measurement electrodes are such that one is positioned to the right, one is positioned to the left and one is positioned below the reference electrode.

In embodiments of the invention, the distance between the reference electrode and each measurement electrode is between 3 to 10 centimeters.

In embodiments of the invention, the electrodes are integrated in one electrode patch, wherein measuring bio-potential signals comprises providing the electrode patch for coupling to the abdomen of the pregnant woman.

In embodiments of the invention, processing the bio-potential signals comprises at least one of time-domain filtering, frequency-domain filtering, time-frequency-domain filtering, or blind source separation.

In embodiments of the invention, processing EHG signals comprises converting EHG signals into uterine contraction signals.

In embodiments of the invention, processing EHG signals comprises at least one of root-mean-square, averaging, linear filters, integration operators, energy operators, or entropy operators.

In embodiments of the invention, analyzing uterine contraction signals comprises extracting uterine contraction features to calculate uterine contraction statistics.

In embodiments of the invention, the uterine contraction features comprise at least one of: onset, end, or amplitude of a contraction.

In embodiments of the invention, analyzing uterine contraction signals comprises determining the contraction onset by determining the inflexion point of the uterine contraction signal, verifying whether the inflection point corresponds to an ascending slope and determining the closest zero-derivative point in the uterine contraction signal prior to the inflexion point.

In embodiments of the invention, analyzing uterine contraction signals comprises determining the end of a contraction by determining the inflexion point of the uterine contraction signals, verifying if this inflexion point corresponds to a descending slope and determining the closest zero-derivative point of the uterine contraction signals.

In embodiments of the invention, analyzing uterine contraction signals further comprises determining the contraction amplitude by determining the local maximum between the contraction onset and the end of a contraction.

In embodiments of the invention, analyzing uterine contraction signals comprises identifying patterns in the uterine contraction signals by applying a wavelet transform to the uterine contraction signals, wherein the onset of the contraction is determined by the point at which the energy of the wavelet raises above a predetermined value and the amplitude of the contraction is determined by the total power of the wavelet transform. The predetermined value may adapt overtime to learn a user's personal contraction pattern.

In embodiments of the invention, analyzing uterine contraction signals comprises matching the uterine contraction signals with template signals stored in a database.

In embodiments of the invention, the database is user specific.

In embodiments of the invention, the uterine contraction statistics comprise at least one of: frequency, duration, or intensity of contraction.

In embodiments of the invention, measuring bio-potential signals comprises receiving bio-potential signals, and conditioning and amplifying the received bio-potential signals.

In embodiments of the invention, measuring bio-potential signals comprises filtering artifacts.

In embodiments of the invention, the filtering of artifacts comprises measuring a motion artifact signal in parallel to the bio-potential signals.

In embodiments of the invention, the motion artifact signal is measured by an accelerometer attached to the at least two electrodes.

In embodiments of the invention, the motion artifact signal is a contact impedance measured using the at least two electrodes.

In embodiments of the invention, filtering artifacts comprises receiving measured motion artifact data.

In embodiments of the invention, analyzing the uterine contraction signals comprises extracting uterine contraction features from the uterine contraction signals, detecting contractions, and calculating uterine contraction statistics.

Non-limiting examples of uterine contraction statistics include: a number of contractions per hour, a standard deviation of a time between contractions (e.g., in seconds), a mean of the duration of the detected uterine contractions (e.g., in seconds), a standard deviation of the duration of the detected uterine contractions (e.g., in seconds), a mean of an amplitude of the IUP peak during detected contractions (mmHg), a standard deviation of an amplitude of an intra-uterine pressure (IUP) peak during detected contractions (e.g., in mmHg), a mean of the area under the IUP curve during detected contractions (e.g., in mmHg×second), and a standard deviation of the area under the IUP curve during detected contractions (e.g., in mmHg×second).

In embodiments of the invention, the method further comprises (e) processing the bio-potential signals to extract uterine electromyogram (UEMG) signals, (f) processing the UEMG signals to extract UEMG markers, and (g) classifying the bio-potential signals into contraction types based on the UEMG markers.

In embodiments of the invention, processing UEMG signals comprises extracting UEMG features to extract the UEMG markers.

In embodiments of the invention, at least one of the uterine contraction statistics of step (d) are used as input for the processing of UEMG signals in step (f).

In embodiments of the invention, the method further comprises (h) identifying bio-processing signals representing labor.

In embodiments of the invention, identifying bio-processing signals representing labor comprises at least one of: a uterine contraction statistic of step (d) or a contraction type of step (g).

In embodiments of the invention, the method further comprises (i) processing the bio-potential signals to extract maternal electrocardiogram (mECG) signals, and (j) processing the mECG signals to extract a maternal heart rate (mHR).

In embodiments of the invention, processing the mECG signals comprises analyzing the mECG signals to extract mECG R-waves.

In embodiments of the invention, the method further comprises (k) processing the maternal heart rate to extract maternal stress level.

In embodiments of the invention, the method further comprises (l) processing the bio-potential signals to extract fetal electrocardiogram (fECG) signals, and (j) processing the fECG signals to extract a fetal heart rate (fHR).

In embodiments of the invention, the processing to extract fECG signals in step (l) uses the mECG signals of step (i) as input to filter the mECG signals from the fECG signals. For example, mECG may be removed from fECG via subtraction in the time domain. Alternatively or additionally, adaptive filtering or Kalman filtering may be used.

In embodiments of the invention, the processing of the fECG signals comprises determining the morphology of the fECG signals.

In embodiments of the invention, the method further comprises simultaneously visualizing the uterine contraction signals and the fHR signals to determine fHR changes during a contraction.

In embodiments of the invention, the method further comprises measuring maternal activity using an activity sensor.

In embodiments of the invention, the method further comprises measuring fetal activity using an accelerometer positioned on the abdomen of the pregnant woman.

In embodiments of the invention, the method further comprises providing information to the pregnant woman based on at least one of: a uterine contraction statistic of step (d) or a contraction type of step (g).

In an embodiment, a contraction monitoring device is provided which comprises an electrode patch comprising at least two electrodes, including a measurement electrode and a reference electrode, and a sensor module configured to be connected to the electrode patch, the sensor module comprising a signal acquisition module, a signal processing module, a power management module, a sensor control module, and at least one of a memory module or a data transmission module.

While the electrodes are incorporated inside the electrode patch, there is no risk for the woman to misplace the various electrodes as their relative positioning is already correct on the electrode patch. The use of an electrode patch also improves the experience and the ease of use of contraction monitoring, as it does not require attaching multiple electrodes to the abdomen, but only requires attaching one single electrode patch. Also, this electrode patch can be just positioned on the woman's abdomen. It can then be attached by an adhesive layer or incorporated in any piece of garment or textile. The woman can also continue her normal activities while wearing it and does not need to lie down as compared to most of today's contraction monitoring devices used in medical environments. The sensor module is configured to receive all the biopotential signals through the signal acquisition module. The signal processing module is responsible for transforming these signals into data understandable by the user. These data are transferred to a user portable device via the data transmission module or can also be kept in memory on the device itself. All these operations are coordinated by the sensor control module. The sensor module therefore enables the user to visualize all the signals and the information related to the uterus activity on a portable device and be accordingly informed.

In embodiments of the invention, the electrode patch comprises a sensor module receiving area to connect the sensor module to the electrode patch.

In embodiments of the invention, the electrode patch is disposable.

In embodiments of the invention, the electrode patch and the sensor module are removably or fixedly positioned in a garment, clothing, textile, or belt.

In embodiments of the invention, the electrode patch comprises an adhesive layer to attach to the body of a user.

In embodiments of the invention, the electrode patch comprises electrode wires.

In embodiments of the invention, the electrode patch is connected to the sensor module by a magnetic connection, and wherein the magnetic connection is configured to provide an electrical contact between the sensor module and the electrode patch when connected.

In embodiments of the invention, the electrode patch is connected to the sensor module by a mechanical connection, wherein the mechanical connection is configured to provide an electrical contact between the sensor module and the electrode patch when connected.

In embodiments of the invention, the electrode patch further comprises a bias electrode.

In embodiments of the invention, the bias electrode is located substantially in the middle of the electrode patch, and wherein the measurement electrode is located on one side of the bias electrode and the reference electrode on the opposite side than the one side with respect to the bias electrode.

In embodiments of the invention, the electrode patch comprises a second measurement electrode, wherein the first and second measurement electrodes are located on the two extremities of the electrode patch, wherein the reference electrode is located substantially in the middle of the electrode patch and wherein the bias electrode is located between one of the measurement electrodes and the reference electrode.

In embodiments of the invention, the electrode patch comprises a back electrode which, during use, is positioned on the back of a pregnant woman.

In embodiments of the invention, the electrode patch further comprises a third measurement electrode, wherein the first and second measurement electrodes and the reference electrode are positioned substantially on a line, wherein the third measurement electrode is positioned below the reference electrode substantially perpendicular to the line, and wherein the bias electrode is located between a measurement electrode and the reference electrode.

In embodiments of the invention, the distance between the measurement electrode and the reference electrode is between three and ten centimeters.

In embodiments of the invention, the signal processing module is configured to perform any of the method embodiments provided.

In embodiments of the invention, the signal acquisition module comprises a conditioning module.

In embodiments of the invention, the signal acquisition module comprises an amplification module.

In embodiments of the invention, the signal acquisition module comprises an analog filter module.

In embodiments of the invention, the signal acquisition module comprises an analog-to-digital conversion module.

In embodiments of the invention, the memory module is configured to store data generated by the signal processing module.

In embodiments of the invention, the data transmission module is configured to transmit signals generated by the signal processing module to a user device.

In embodiments of the invention, the power management module is configured to deliver power to the contraction monitoring device.

In embodiments of the invention, the sensor module further comprises an inertial motion sensing module.

In embodiments of the invention, the inertial sensing module comprises at least one of a one-axis accelerometer, a two-axis accelerometer, or a tri-axis accelerometer.

In embodiments of the invention, the inertial sensing module further comprises at least one of: a one-axis gyroscope, a two-axis gyroscope, or a tri-axis gyroscope.

In embodiments of the invention, the inertial sensing module further comprises at least one of: a one-axis magnetometer, a two-axis magnetometer, or a tri-axis magnetometer.

In embodiments of the invention, the sensor module further comprises a contact-impedance measurement module.

In embodiments of the invention, the sensor module further includes a user interface module.

In embodiments of the invention, the user interface module comprises at least one LED.

In embodiments of the invention, the user interface module comprises at least one of a buzzer, a vibrating element, an audio speaker, or a display.

Another aspect of the present disclosure is directed to a computer-implemented method for identifying a labor state in a pregnant female. In various embodiments, the method includes: acquiring a physiological signal from a physiological sensor; processing the physiological signal to identify and extract a parameter of interest from the physiological signal; and analyzing the parameter of interest to determine whether the parameter is indicative of a labor state.

In some embodiments, the method further includes developing a personalized baseline. In some such embodiments, analyzing the parameter of interest to determine whether the parameter is indicative of a labor state includes: comparing the parameter of interest to the personalized baseline to identify a deviation from the personalized baseline, and determining whether the deviation is indicative of the labor state. The parameter of interest may be tracked over time to develop the personalized baseline.

In some embodiments, a plurality of parameters of interest are identified and extracted from the physiological signal. In some such embodiments, analyzing the parameter of interest to determine whether the parameter is indicative of a labor state includes: identifying a pattern in the plurality of parameters, and determining whether the pattern is indicative of the labor state. The plurality of parameters may include physiological and behavioral parameters.

In some embodiments, analyzing the parameter of interest to determine whether the parameter is indicative of a labor state includes feeding the parameter into a machine learning model trained to detect labor. The machine learning model may include one or more of: a generalized linear model, a decision tree, a support vector machine, a k-nearest neighbor, a neural network, a deep neural network, a random forest, and a hierarchical model.

In some embodiments, analyzing the parameter of interest to determine whether the parameter is indicative of the labor state includes comparing the parameter to community data stored in a database. The community data may include one or more of: recorded trends, rules, correlations, and observations generated from tracking, aggregating, and analyzing parameters from a plurality of users.

Acquiring a physiological signal may include acquiring a plurality of physiological signals from a plurality of physiological sensors. In some embodiments, acquiring a physiological signal includes acquiring one or more of: an electrohysterography signal, a signal indicative of maternal uterine activity, maternal uterine muscle contractions, maternal heart electrical activity, maternal heart rate, fetal movement, fetal heart rate, maternal activity, maternal stress, fetal stress, a force of contraction signal, and/or a frequency of contraction signal, as described elsewhere herein.

In some embodiments, processing the physiological signal to identify and extract a parameter of interest includes identifying and extracting one or more of: a maternal heart rate metric, a maternal heart rate variability metric, a fetal heart rate metric, a fetal heart rate variability metric, a range of an electrohysterography signal, a power of an electrohysterography signal in a specific frequency band, a frequency feature of an electrohysterography signal, a time-frequency feature of an electrohysterography signal, a frequency of contractions, a duration of contractions, an amplitude of contractions, and a force of contractions.

In some embodiments, the method further includes generating an alert related to the labor status. In some embodiments, the method further includes sharing the labor status or an alert related to the labor status with a contact. In some embodiments, the method further includes transmitting the labor status or an alert related to the labor status with a healthcare provider or labor support professional. In some embodiments, the method further includes performing an action based on the labor status. For example, in some embodiments, the method includes contacting a service provider to request services if the labor status is positive.

In some embodiments, the method further includes determining a probability that the pregnant female is experiencing labor-inducing contractions. The probability is computed using generalized linear regression models or logistic regression models where a set of parameters (e.g., EHG signals, maternal heart rate, etc.) are linearly combined into a number that represents the probability. A degree of certainty around the determined probability may also be determined. Additionally or alternatively, the method may further include determining a probability that the pregnant female will enter the labor state within a given time period. Additionally or alternatively, the method may further include determining an estimate of time until the pregnant female enters the labor state.

Another aspect of the disclosure is directed to a system for identifying a labor state in a pregnant female. In various embodiments, the system includes a physiological sensor, a processor communicatively coupled to the physiological sensor, and a computer-readable medium having non-transitory, processor-executable instructions stored thereon.

Execution of the instructions causes the processor to perform any one or more of the methods described above or elsewhere herein.

In some embodiments of the system, the physiological sensor includes at least one measurement electrode and at least one reference electrode. The system may include one, one or more, or a plurality of physiological sensors. In some embodiments, acquiring a physiological signal includes acquiring a plurality of physiological signals. The physiological sensor may include one or more physiological sensors configured, for example, to measure one or more of an electrohysterography signal, maternal uterine activity, maternal uterine muscle contractions, maternal heart electrical activity, maternal heart rate, fetal movement, fetal heart rate, maternal activity, maternal stress, fetal stress, a force of contractions, and a frequency of contractions. The one or more physiological sensors may sense one or more biopotential signals. In some embodiments, the parameter of interest includes one or more of: a maternal heart rate metric, a maternal heart rate variability metric, a fetal heart rate metric, a fetal heart rate variability metric, a range of an electrohysterography signal, a power of an electrohysterography signal in a specific frequency band, a frequency feature of an electrohysterography signal, a time-frequency feature of an electrohysterography signal, a frequency of contractions, a duration of contractions, a force of contractions, a variability in contractions, and an amplitude of contractions.

In some embodiments, the system also includes a portable and wearable sensor module. The sensor module includes the physiological sensor, an electronic circuit, and a wireless antenna. In some such embodiments, the sensor module further includes the processor and the computer-readable medium. Such a sensor module may be in wireless communication with a mobile computing device. In other embodiments, the processor and the computer-readable medium are located within a mobile computing device, and the sensor module is in wireless communication with the mobile computing device.

In some embodiments having a mobile computing device, the mobile computing device is a smartphone, a smart watch, smart glasses, smart contact lenses, other wearable computer, a tablet, a laptop, or a personal computer.

In some embodiments having a wearable sensor module, the sensor module connects to or forms a portion of: a patch, a belt, a strap, a band, a t-shirt, the elastic of a pair of pants, or other clothing or other wearable accessory.

Another aspect of the present disclosure is directed to a system for identifying a labor state in a pregnant female, the system including: a patch coupled to an abdominal region of the pregnant female; a physiological sensor coupled to the patch or integrated into the patch; a processor communicatively coupled to the physiological sensor; and a computer-readable medium having non-transitory, processor-executable instructions stored thereon, wherein execution of the instructions causes the processor to perform a method.

In some embodiments, the method includes: receiving an input indicating a gestational age of a pregnancy; acquiring a physiological signal from the physiological sensor, wherein the physiological signal is one or more of: an electrohysterography signal, a maternal heart rate signal, a contraction signal, a force of contraction signal, and a frequency of contraction signal; processing the physiological signal to identify and extract a parameter of interest; and feeding the parameter of interest into a machine learning model. In some embodiments, the machine learning model is configured to: determine a first labor probability based on the parameter of interest, determine a second labor probability based on the parameter of interest or a second parameter of interest and the gestational age of the pregnancy, and classify the labor state of the pregnant female based on the first and second labor probability.

In some embodiments, the machine learning model is further configured to determine whether the first labor probability is greater than a baseline, determine whether the second probability is greater than one or more of: a first threshold and a second threshold, and when the first labor probability is greater than the baseline and the second labor probability is greater than one or both of the first threshold and the second threshold, outputting an indication of a labor state of the pregnant female.

In some embodiments, the baseline comprises a personalized baseline.

In some embodiments, determining the personalized baseline includes: tracking the parameter of interest over time; determining a value of the parameter of interest over a period of time; and calculating a personalized baseline based on the determined value.

In some embodiments, the method performed by the processor further includes comparing the parameter of interest to the personalized baseline to identify a deviation from the personalized baseline, and determining whether the deviation is indicative of the labor state.

In some embodiments, the deviation is indicative of the labor state when the deviation is n standard deviations greater than the personalized baseline.

In some embodiments, the deviation is further analyzed using community data stored in a database.

In some embodiments, the community data includes one or more of: recorded trends, rules, correlations, and observations generated from tracking, aggregating, and analyzing parameters from a plurality of users.

In some embodiments, analyzing the parameter of interest to determine whether the parameter is indicative of a labor state includes: identifying a pattern in the parameter of interest over time, and determining whether the pattern is indicative of the labor state.

In some embodiments, the parameter of interest includes a plurality of parameters of interest, such that the plurality of parameters of interest include physiological and behavioral parameters.

In some embodiments, the machine learning models comprises one or more of a generalized linear model, a decision tree, a support vector machine, a k-nearest neighbor, a neural network, a deep neural network, a random forest, and a hierarchical model.

In some embodiments, the physiological sensor comprises a measurement electrode and reference electrode.

In some embodiments, the physiological sensor comprises one or more physiological sensors configured to measure one or more of the electrohysterography signal, the maternal heart rate signal, the contraction signal, the force of contraction signal, and the frequency of contraction signal.

In some embodiments, the parameter of interest comprises one or more of a maternal heart rate metric, a maternal heart rate variability metric, a range of an electrohysterography signal, a power of an electrohysterography signal in a specific frequency band, a frequency feature of an electrohysterography signal, and a time-frequency feature of an electrohysterography signal.

In some embodiments, the patch comprises a portable sensor module coupled to the patch or integrated into the patch, wherein the sensor module comprises the physiological sensor, the processor, and the computer-readable medium and further comprises an electronic circuit and a wireless antenna, and wherein the sensor module is in wireless communication with a mobile computing device.

In some embodiments, the method performed by the processor further includes generating an alert.

In some embodiments, the method performed by the processor further includes determining a degree of certainty around one or more of the first labor probability and the second labor probability.

In some embodiments, the method performed by the processor further includes determining a probability that the pregnant female will enter the labor state within a given time period.

In some embodiments, the method performed by the processor further includes determining an estimate of time until the pregnant female enters the labor state.

In some embodiments, the input further includes one or more of: clinical data, demographic information, activity, movement patterns, and behavioral parameters.

Another aspect of the present disclosure is directed to a computer-implemented method for identifying a labor state in a pregnant female, including: receiving, using a processor, an input indicating a gestational age of a pregnancy; acquiring a physiological signal from a physiological sensor coupled to or integrated into a patch coupled to an abdominal region of the pregnant female, wherein the physiological signal is one or more of: an electrohysterography signal, a maternal heart rate signal, a contraction signal, a force of contraction signal, and a frequency of contraction signal; processing, using the processor, the physiological signal to identify and extract a parameter of interest; and feeding, using the processor, the parameter of interest into a machine learning model.

In some embodiments, the machine learning model is configured to: determine a first labor probability based on the parameter of interest, determine a second labor probability based on the parameter of interest or a second parameter of interest and the gestational age of the pregnancy, and classify the labor state of the pregnant female based on the first and second labor probability.

In some embodiments, the machine learning model is further configured to determine whether the first labor probability is greater than a baseline, determine whether the second probability is greater than one or more of: a first threshold and a second threshold, and when the first labor probability is greater than the baseline and the second labor probability is greater than one or both of the first threshold and the second threshold, outputting an indication of a labor state of the pregnant female.

In some embodiments, the baseline includes a personalized baseline.

In some embodiments, determining the personalized baseline includes: tracking the parameter of interest over time; determining a value of the parameter of interest over a period of time; and calculating a personalized baseline based on the determined value.

These and other aspects of the disclosure are illustrated in the figures and described in more detail below.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

Figure 1:
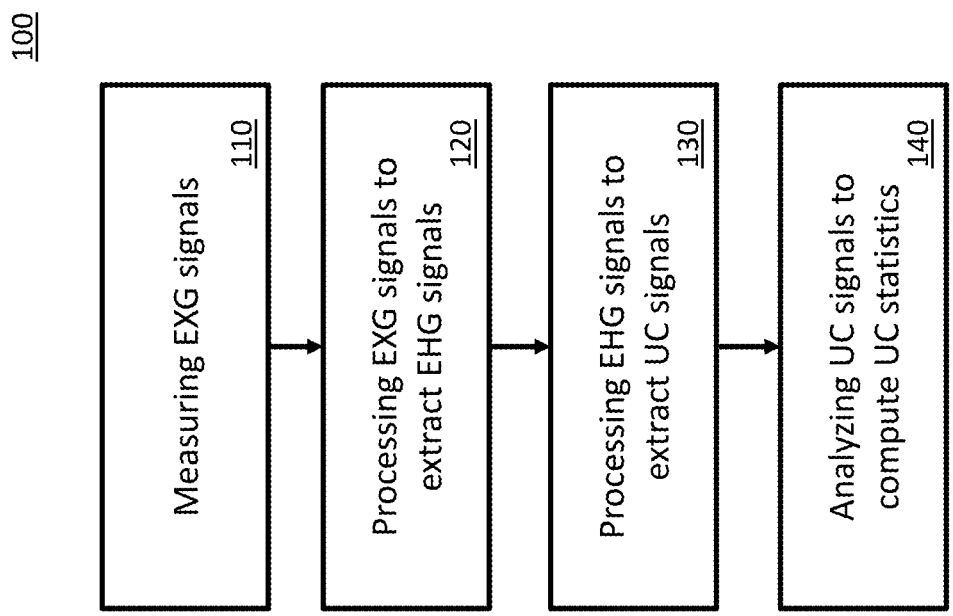
FIG. 1 is an exemplary top-level flow diagram illustrating an embodiment of the method for measuring contractions based on bio-potential signals.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

Furthermore, the various embodiments, although referred to as "preferred" are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present invention, the only enumerated components of the device are A and B, and further the claim should be interpreted as including equivalents of those components.

In general, the systems and methods described herein include a sensor module used to monitor contractions or monitor pregnancy or labor in a pregnant woman (i.e., a pregnant female human) or other pregnant female animal. Results of the monitoring may be provided to the pregnant woman being monitored and/or to a gynecologist, obstetrician, other physician, nurse practitioner, veterinarian, other healthcare provider, doula, midwife, other birthing specialist, spouse, partner, parent, sibling, other family member, friend, a healthcare facility administrator, a service provider who may provide ride-sharing, taxi, childcare, or other services to a woman in labor, or any other individual with whom the pregnant woman wishes to share such information.

As used herein, "pregnant woman" and "pregnant female" may be used interchangeably. It will be appreciated by one skilled in the art that each of the embodiments described herein may be used to monitor and detect a labor status in any pregnant mammal regardless of species.

As used herein, a "labor status" refers to a determination regarding the state of being in labor. Labor, or childbirth, is a process having various stages. In the first stage of labor (i.e., dilation), contractions become increasingly regular, the cervix dilates, and the baby descends to the mid-pelvis. In the second stage of labor (i.e., expulsion), the baby progresses through the birth canal (i.e., the cervix and vagina) and is expelled from the mother's body. The third stage of labor (i.e., placental stage) involves the delivery of the placenta and fetal membranes. The labor status may be positive (i.e., labor has begun) or negative (i.e., labor has not yet begun). The labor status may include a prediction of time until labor or a likelihood of beginning labor within a specified time period. The labor status may include a degree of likelihood that a woman is, or soon will be, in labor.

Current solutions for contraction monitoring are only available to care professionals and for use in a controlled care environment, are constrained in their functionality, and are limited in their portability and accuracy. As such, a method and a device for ambulatory contraction monitoring and labor detection can prove desirable for allowing pregnant woman to monitor their contractions and labor status at any time and in any environment, to get new insights on how other health parameters can affect her contractions or labor status, or share this information with her partner, family, friends and healthcare practitioners during or in between visits.

At least two cutaneous electrodes including a measurement electrode and a reference electrode, provided in a wearable system including an electrode patch and a sensor module, and placed on the pregnant woman's abdomen. The electrodes are configured to measure bio-potential (EXG) signals, which may include electrohysterogram (EHG), uterine electromyogram (UEMG), maternal electrocardiogram (mECG), fetus electrocardiogram (fECG), etc signals. This method allows the extraction and isolation of the required signals to improve the measurement of uterine contractions and labor detection.

The combination of the various signals improves the precision of the analysis of uterine contractions and all its implications for the mother and the fetus. Furthermore, the combination of the various signals provides new insights in the relation between the behavior of the mother and her contractions. The method is extremely robust and does not require a practitioner to position, operate, or analyze the signals obtained. Furthermore, the method is suitable for being used directly by the pregnant woman.

The method advantageously monitors contractions based on bio-potential (EXG) signals measured on the abdomen of a pregnant woman. This can be achieved, according to one embodiment disclosed herein, by the method 100 for monitoring uterine contractions from EXG signals, as illustrated in FIG. 1. As shown in FIG. 1, the method 100 for monitoring uterine contractions can include: measuring, at 110, bio-potential (EXG) signals, comprising EHG signals; processing, at 120, EXG signals to extract electrohysterogram (EHG) signals; processing, at 130, EHG signals to extract uterine contraction (UC) signals; and analyzing, at 140, UC signals to compute relevant UC statistics Measuring, at 110, EXG signals can be achieved using at least two electrodes, yielding at least one channel EXG signal. In this configuration, one electrode can be referred to as the measurement electrode, whereas the second electrode can be referred to as the reference electrode. In one embodiment, measuring EXG signals can be achieved using a third electrode, used as a bias electrode or as a right leg drive electrode, with the main objective to reduce the noise of the EXG measurement. In an alternative embodiment, measuring EXG signals can be achieved using additional electrodes, allowing the measurement of multiple channel EXG signals. The multiple electrodes can be positioned on different locations on the abdomen, advantageously providing multi-dimensional measurement of the uterine electrical activity.

Figure 2A:
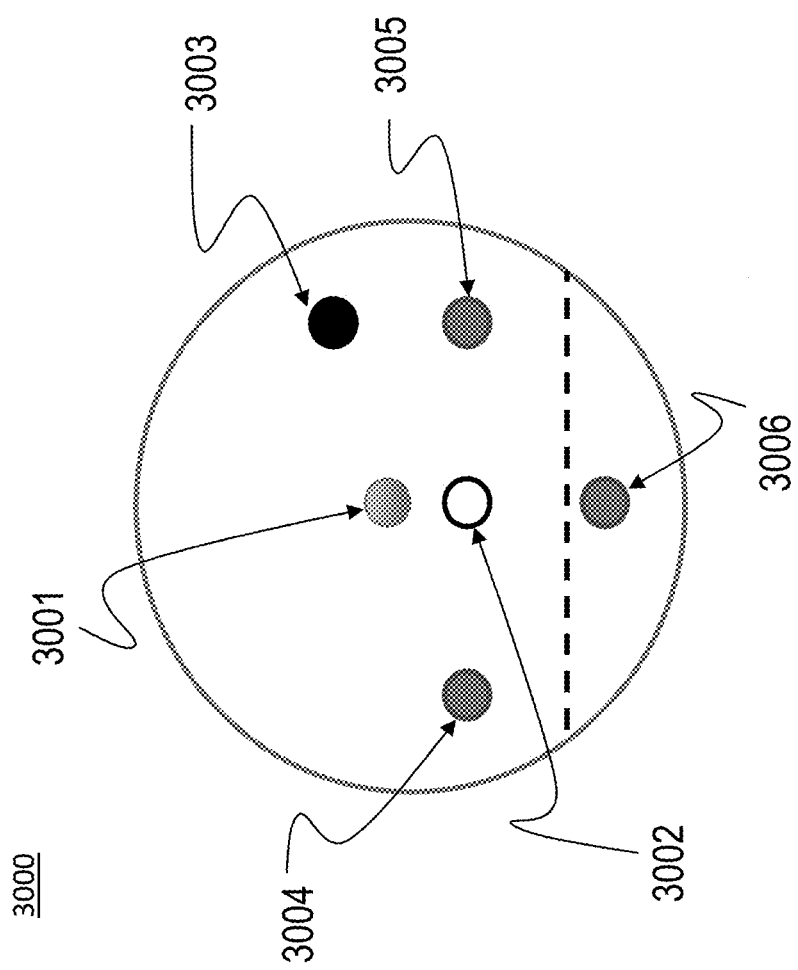
FIG. 2A is an exemplary diagram illustrating the position of the electrodes on the woman's abdomen.

In one embodiment, illustrated on FIG. 2A, the method 100 for contraction monitoring of FIG. 1 uses three measurement electrodes (3004, 3005, 3006), one reference electrode 3002 and one bias electrode 3003. The reference electrode 3002 is positioned slightly under the navel 3001. The three measurement electrodes (3004, 3005, 3006) are positioned respectively to the right, to the left, and below the reference electrode 3002, as illustrated on FIG. 2A. Preferably, the distance between the reference electrode 3002 and each measurement electrode (3004, 3005, 3006) comprises between three to ten centimeters. The bias or right leg drive electrode 3003 can be positioned anywhere on the abdomen, but not too far from the other electrodes. Preferably and advantageously, all electrodes can be integrated into an electrode patch. The electrode patch can significantly improve the reliability, the experience, and the use of the method 100 for monitoring contractions of FIG. 1. The use of an electrode patch improves the reliability of contraction monitoring, as it is not possible for a user to misplace the different electrodes relatively to each other, as they are always in the same relative position. The use of an electrode patch improves the experience and the ease of use of contraction monitoring, as it does not require attaching multiple electrodes to the abdomen but only requires attaching one single electrode patch.

Referring to again to FIG. 1, processing, at 120, EXG signals to extract EHG signals comprises isolating from the EXG signals the part of the EXG signals that is relevant to the electrical activity of the uterus, and separating it out from the part of the EXG that is related to other physiological phenomena, noise, artifacts, and any other contributions.

Processing, at 120, EXG signals to extract EHG signals can be achieved using signal processing techniques including but not limited to time-domain filtering, frequency-domain filtering, time-frequency-domain filtering, and/or blind source separation. For example, and because physiology teaches us that EHG signals are known to have a frequency content contained within the 0.3 to 0.8 Hz bandwidth, each EHG signal can be extracted from the corresponding EXG signal by applying a filter with a bandpass of 0.3 Hz to 0.8 Hz. In another example, the multiple EXG channels are combined and processed using independent component analysis or other blind source separation technique to separate components of EXG signals with different variance. The components with the most variance in the low frequency band can then be retained as the EHG signals.

Processing, at 130, EHG signals to extract UC signals comprises converting the EHG signals into UC signals. Processing, at 130, EHG signals to extract UC signals can be achieved using signal processing techniques including but not limited to root-mean-square, averaging, linear filters, integration operators, energy operators or entropy operators.

Figure 2B:
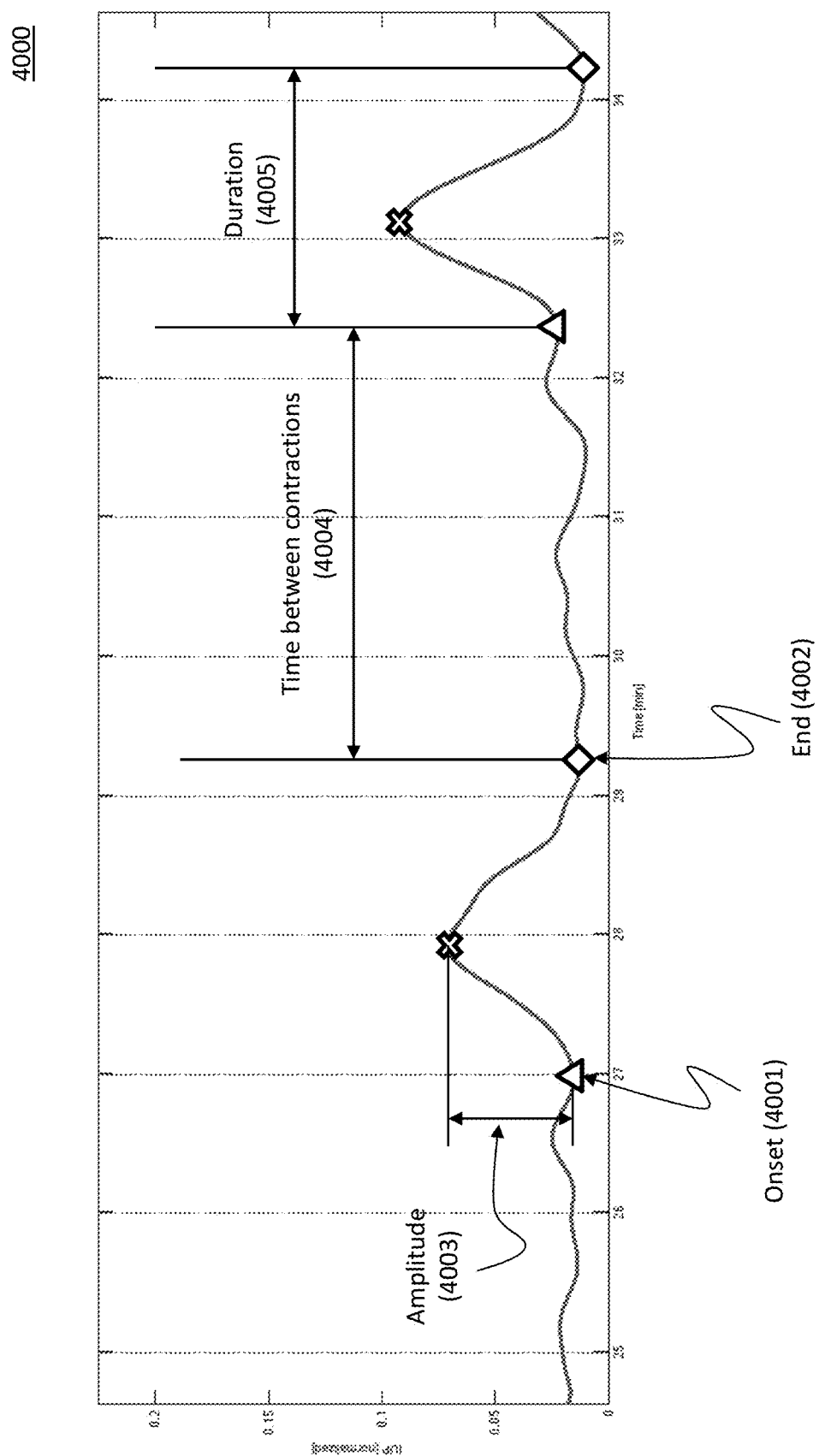
FIG. 2B is an exemplary representation of a uterine contraction, uterine contraction features and uterine contraction statistics.

Advantageously, analyzing, at 140, UC signals to compute relevant UC statistics comprises further analyzing the UC signals to extract relevant UC features and calculating relevant UC statistics. The UC signal is usually not intelligible for a person who does not have a clinical background. Therefore, although the UC signal can provide great information to the clinically trained expert, it can only provide very limited value to the non-clinically qualified user, like most pregnant women. Analyzing, at 140, UC signals to compute relevant UC statistics advantageously analyzes the UC signals to provide a set of features that are intelligible to the common user. Relevant UC features can include but are not limited to onset, end, amplitude of a contraction. In one embodiment, detecting the contraction on-set can be achieved by detecting the inflexion point in the UC signal, verifying that this inflection point corresponds to an ascending slope, and then finding the closest zero-derivative point in the UC signal prior to the inflexion point. The zero-derivative point can be used as an estimation of the contraction onset. Similarly, detecting the end of a contraction can be achieved by detecting the inflexion point in the UC signal, verifying that this inflection point corresponds to a descending slope, and then finding the closest zero-derivative point of the UC signal after the inflexion point. The zero-derivative point can be used as an estimation of the contraction end. Then the local maximum between the contraction onset and end can be used as the measurement of the contraction amplitude. In another example, the amplitude underneath the UC signal and between the contraction onset and end can be used as a measurement of the contraction amplitude. In another embodiment, a wavelet transform can be applied to the UC signal to identify patterns in the UC signal that correspond to a contraction. The onset (respectively the end) of the contraction can then be defined as the point at which the energy of the wavelet transform goes above (respectively below) a certain threshold. The amplitude of the contraction can then be computed as the total power of the wavelet transform between these two points, or as the local maximum in the time domain between the onset and the end of the contraction. In yet another embodiment, template matching can be used to recognize individual contractions. For example, a typical contraction template can be built from a database of contraction recordings. This database may or may not be user specific. Then the UC signal can be cross-correlated with the contraction template, and the maxima in the cross-correlation function can be considered to be the contraction. Onset, end, and amplitude can then be calculated as described above. Relevant UC statistics can include, but are not limited to, frequency, duration, and/or intensity of contractions. Frequency and duration can be directly calculated from the onset and the end of all contractions. The intensity of contractions can be calculated as the amplitude of the contraction. FIG. 2B shows an example of UC features and statistics extracted from a UC signal.

Figure 3A:
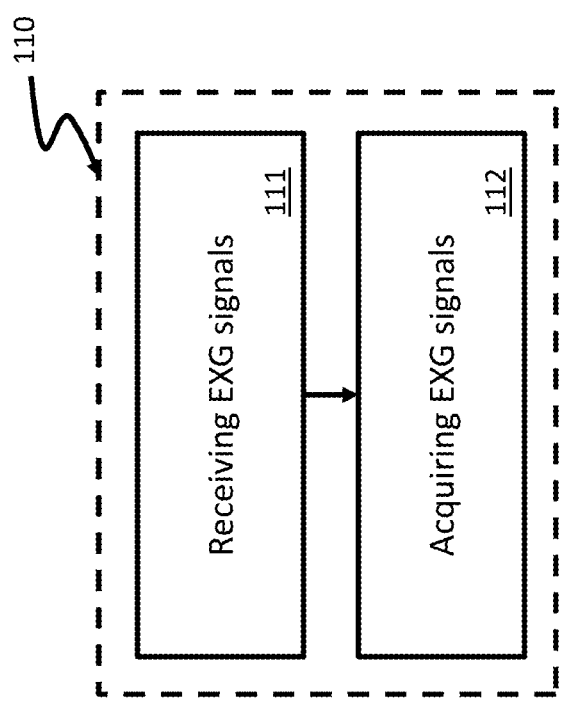
FIG. 3A is an exemplary flow diagram illustrating another alternative embodiment of the method for detecting uterine contractions of FIG. 1.

FIG. 3A shows another alternative embodiment of the method 100 for monitoring uterine contractions of FIG. 1, wherein measuring, at 110, EXG signals can include: receiving, at 111, EXG signals and acquiring, at 112, EXG signals. Acquiring, at 112, EXG signals can be achieved using electronics for conditioning and amplifying the EXG signals, and for converting the analog EXG signals into digital EXG signals (not shown).

Figure 3B:
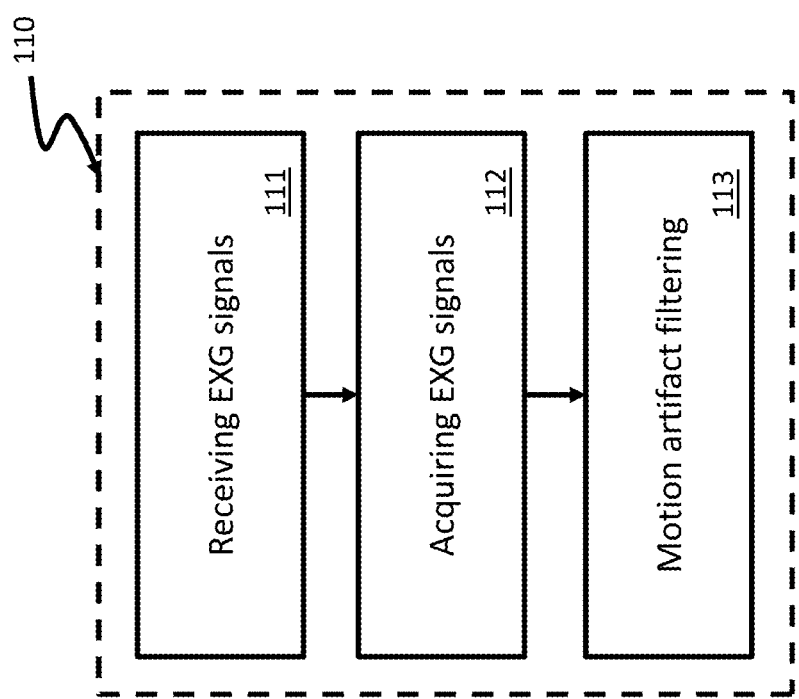
FIG. 3B is an exemplary flow diagram illustrating an alternative embodiment of the method for detecting uterine contractions of FIG. 3A.

EXG signals may be corrupted with movement artifacts, resulting in noise in the signal that can affect their interpretation. Movement artifacts are especially present in the case of ambulatory settings. Despite these artifacts, it is important to correctly and accurately measure the EXG signals. Preferably, the method comprises an automatic identification of motion artifacts. In fact, the presence of artifacts in the EHG signal may lead to misinterpretations of the signal. Processing techniques to identify motion artifacts are therefore required to be able to exclude excerpts of the EXG signals that are corrupted with artifacts. In one embodiment, processing techniques to remove such artifacts can be even more advantageous as the removal of motion artifacts from the EXG signals can avoid the need to exclude certain signal excerpts from the measurement. FIG. 3B shows an alternative embodiment of the method 100 for monitoring uterine contractions of FIG. 3A, wherein measuring, at 110, EXG signals can further include motion artifact filtering, at 113. Motion artifact filtering, at 113, can be done in the analog domain before amplifying the EXG signals, and/or in the digital domain. Motion artifact filtering, at 113, advantageously detects and removes artifacts from the EXG signals, in order to increase the quality and signal-to-noise ratio of the EXG signals. Motion artifact filtering, at 113, can be achieved using a variety of signal processing techniques, including but not limited to: band-pass filters, linear filters, adaptive filters, wavelet filters, or blind source separation techniques.

Figure 3C:
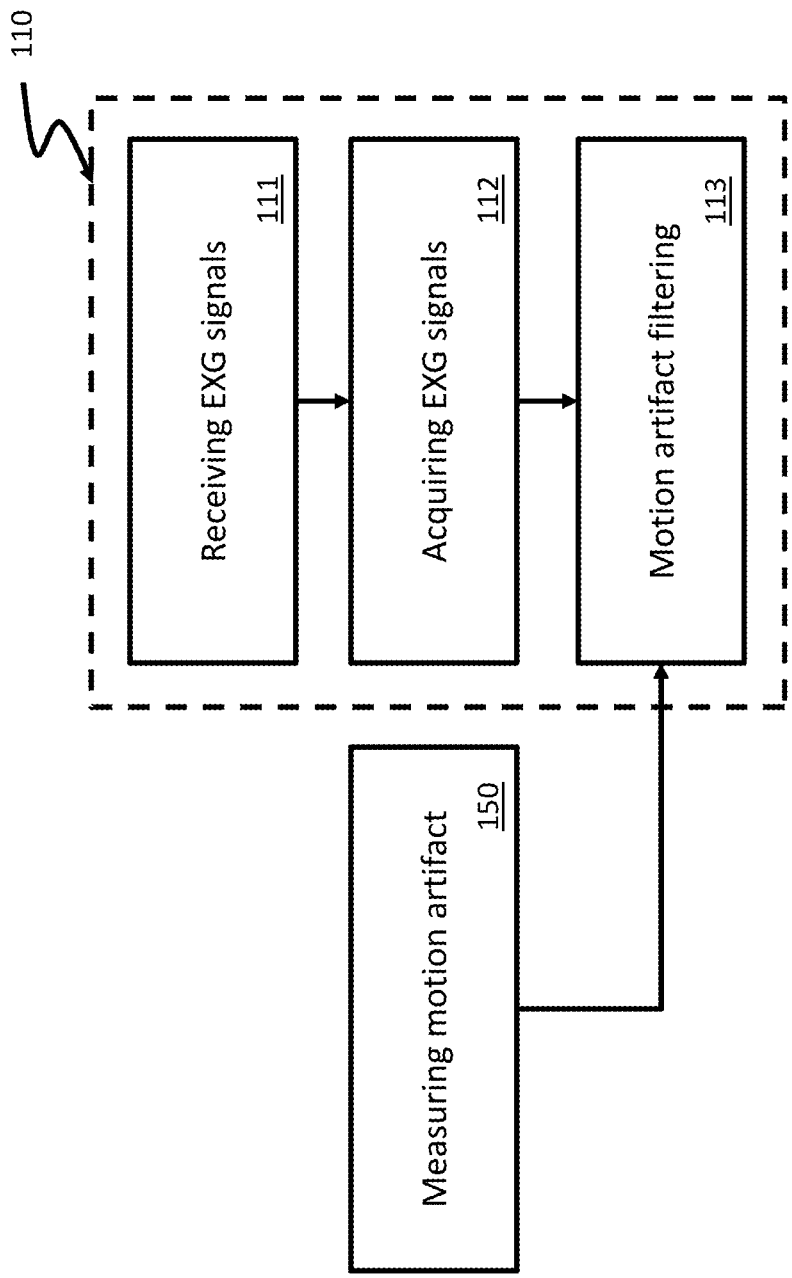
FIG. 3C is an exemplary flow diagram illustrating an alternative embodiment of the method of detecting uterine contractions of FIG. 3B.

Alternatively and advantageously, motion artifact filtering, at 113, can be achieved using an additional motion artifact signal that is measured in parallel to the EXG signals and mainly carries information about the artifacts. For example, the motion artifact signal can be measured using an accelerometer attached to the electrode patch. In another example, the motion artifact signal can be the contact impedance measured using the same electrodes as the ones used for measuring EXG signals. The motion artifact signal can be used as an input to the motion artifact filter. For example, the motion artifact signal can be used as the input to an adaptive filter representing an estimation of the noise. The adaptive filter, at 113, can then function to remove the noise estimation from the EXG signals, yielding cleaner and more accurate signals. FIG. 3C shows an alternative embodiment of the method 100 for monitoring uterine contractions of FIG. 3B, wherein measuring motion artifact signal, at 150, is used as an input to motion artifact filtering, at 113.

Figure 4:
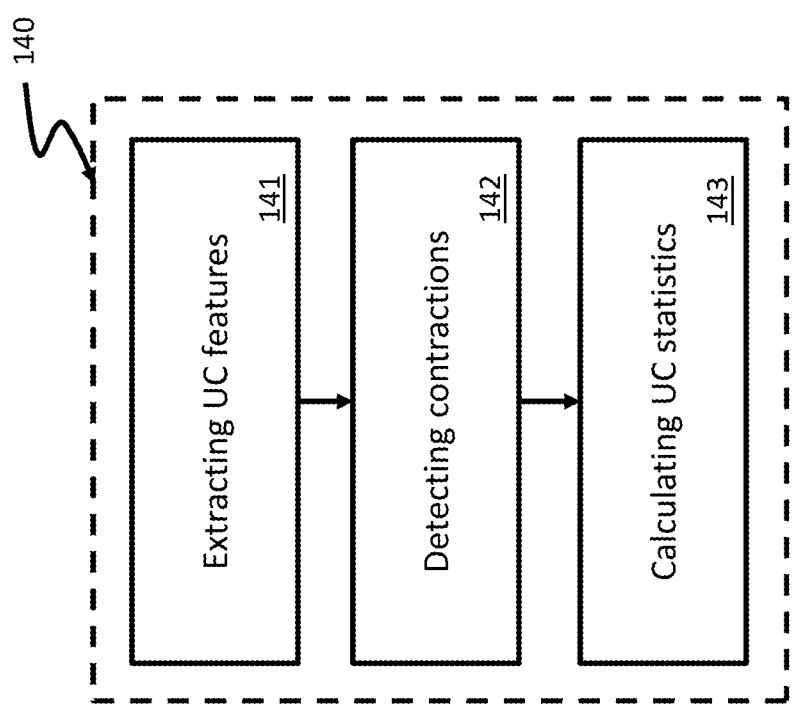
FIG. 4 is an exemplary flow diagram illustrating yet another alternative embodiment of the method for detecting uterine contractions of FIG. 1.

FIG. 4 shows another alternative embodiment of the method 100 for monitoring uterine contractions of FIG. 1, wherein analyzing, at 140, UC signals to compute relevant UC statistics can preferably include extracting, at 141, UC features, detecting, at 142, contractions, and calculating, at 143, UC statistics. Extracting, at 141, UC features can comprise processing UC signals to yield a set of features that characterize the UC signals. Example of features may include but are not limited to time-domain features (zero-derivative points, inflexion points, local minima, local maxima), frequency-domain features, or time-frequency features. Detecting contractions, at 142, can be performed using a set of thresholds and/or conditions on selected UC features. The thresholds or conditions can be manually set or can be automatically adapted based on the measured signal. For example, in the time domain, a contraction can be detected upon the identification of the following specific sequence: an inflexion point with ascending slope, followed by a local maximum, and followed by an inflexion point with a descending slope. In another example, in the time-frequency domain, a contraction can be detected when the energy of the wavelet transform in a predefined band corresponding to 0.3-0.8 Hz exceeds a certain threshold. Calculating, at 143, statistics can be achieved by further analyzing the UC data for the contractions detected at 142. For example, statistics such as average duration of contractions, time between contractions, or average amplitude can be calculated based on the features extracted at 141 for a set of contractions detected at 142.

Figure 5A:
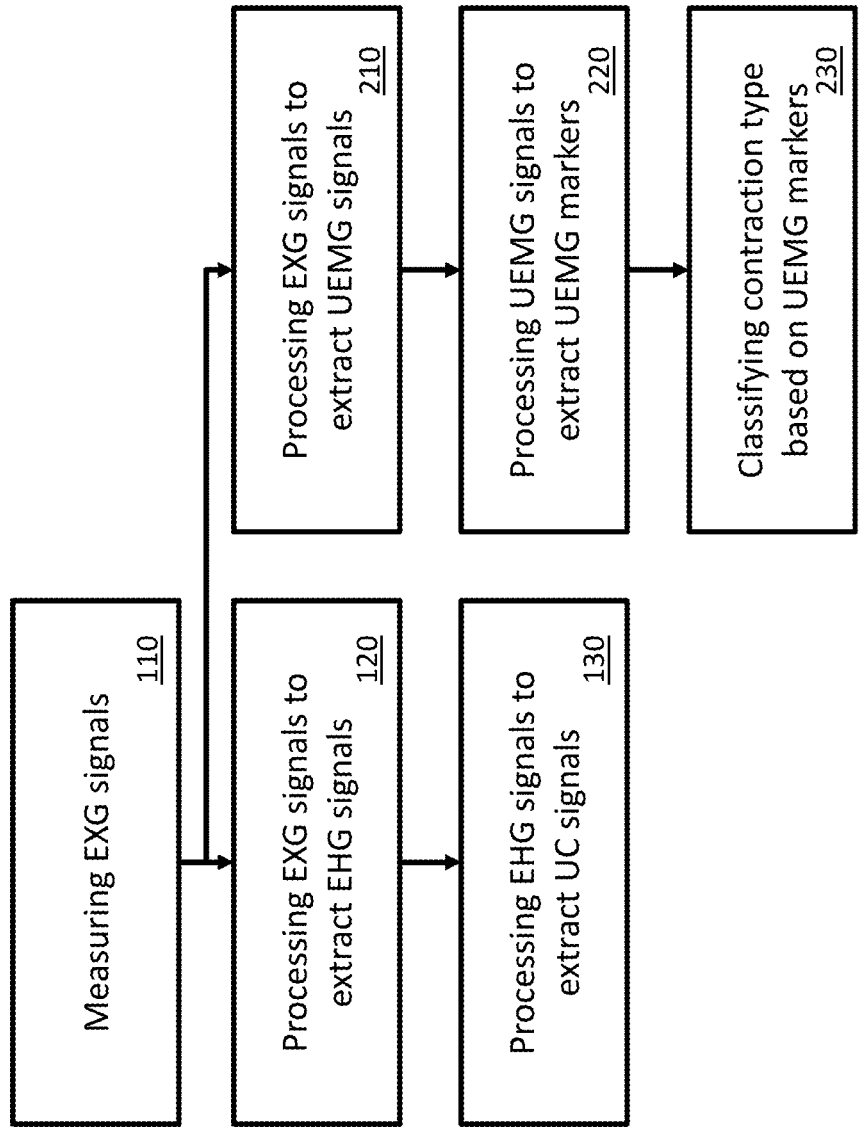
FIG. 5A is an exemplary flow diagram illustrating yet another alternative embodiment of the method for monitoring uterine contractions of FIG. 1.

EHG signals carry information about the UC signals. EHG signals are however limited in their frequency content. Stated somewhat differently, EHG signals provide a high level view on the electrical activity of the uterus. Next to the EHG, there is much more information contained in the EXG signals and that information pertains to the electrical activity of the uterus. Physiology teaches us that a contraction can be seen as the result of the common activation of thousands of uterus muscle cells. The rate at which the uterus contractile cells fire, the pattern at which they are firing, and the spatial distribution of their firing, all contain important information regarding the electrical activity of the uterus, that can be referred to as the fine information on the uterine electrical activity. Advantageously, the fine information can provide a greater detailed view on the contraction and can be used to gather additional knowledge on the contraction. The fine information may, for example, be used to differentiate different types of contractions, or to provide greater insight on whether a contraction may induce labor or not. The fine information on the uterine electrical activity is not included in the EHG signals. Advantageously, this information can be extracted, next to the EHG signal, in a uterine electromyogram signal, or UEMG signal. FIG. 5A shows yet another alternative embodiment of the method 100 for monitoring uterine contractions of FIG. 1, wherein the method 100 for monitoring uterine contractions can further include: processing, at 210, EXG signals to extract uterine electromyogram (UEMG) signals; processing, at 220, UEMG signals to extract UEMG markers; and classifying, at 230, contraction type based on the UEMG markers.

Processing, at 210, EXG signals to extract UEMG signals comprises isolating from the EXG signals the part of the EXG signals that is relevant to the uterine electromyogram, and separating it out from the part of the EXG that is related to other physiological phenomena, noise, artifacts and any other contributions. Processing, at 210, EXG signals to extract UEMG signals can be achieved using signal processing techniques including but not limited to time-domain filtering, frequency-domain filtering, time-frequency-domain filtering and/or blind source separation. It will be noted that UEMG and EHG signals need not be mutually exclusive. In other words, the UEMG signals may partially overlap with the EHG signals.

Processing, at 220, UEMG signals to extract UEMG markers comprises analyzing the UEMG signals to extract relevant UEMG features that can be considered as UEMG markers. Examples of UEMG markers can include but are not limited to UEMG statistical features (average, mean, percentiles, standard deviation, kurtosis or any other statistical moments), power spectrum features (total power in the bandwidth, peak power, mean power, average power, power in certain frequency bands), entropy features, spatial propagation features (laplacian, gradient, and higher order propagation features), etc. The UEMG markers provide a quantification of the fine grained detail of the uterine electrical activity. These markers can then be used to differentiate and classify different types of contractions (e.g., Braxton Hicks, true labor, etc.) and/or the labor state (e.g., labor vs. non-labor).

One exemplary embodiment of a UEMG marker is a standard deviation, a mean, an average, or a power of the EHG signal in the 0.3-0.7 Hz frequency range.

Another exemplary embodiment of a UEMG marker is a standard deviation, a mean, an average, or a power of the EHG signal in the 0.3-1.5 Hz frequency range.

Another exemplary embodiment of a UEMG marker is a standard deviation, a mean, an average, or a power of the EHG signal in the 0.7-1.5 Hz frequency range.

Another exemplary embodiment of a UEMG marker is a peak frequency of the EHG signal in Hertz.

Another exemplary embodiment of a UEMG marker is a median frequency of the EHG signal in Hertz.

Another exemplary embodiment of a UEMG marker is an entropy of the EHG signal.

Another exemplary embodiment of a UEMG marker is a maximum autocorrelation of the root mean square of the EHG signal.

Another exemplary embodiment of a UEMG marker is a conduction velocity of the EHG signal, a directionality of the EHG signal propagation on the abdomen, a number of zero crossings of the EHG signal, and/or an energy of the EHG signal.

One or more UEMG markers may be combined and input to a classifier, for example a machine learning based classifier.

Classifying, at 230, contraction type based on the UEMG markers comprises characterizing the specific type of contraction based on the UEMG markers. Classifying, at 230, can be done using supervised or unsupervised classification techniques. Examples of classification techniques can include, but are not limited to: decision trees, Bayesian networks, artificial neural networks, support vector machine, Markov chains, hierarchical models, etc. In a further embodiment, classifying, at 230, contraction type comprises recognizing a Braxton Hicks contraction from a true labor contraction.

Figure 5B:
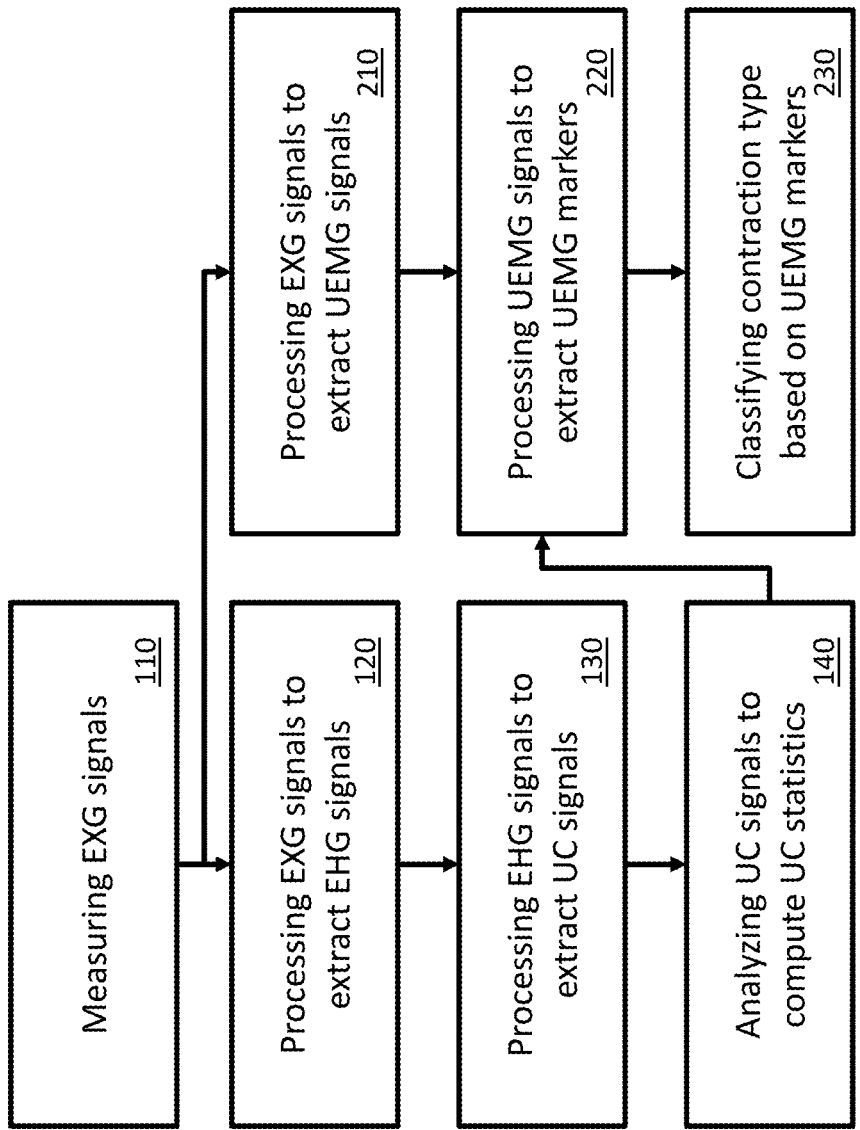
FIG. 5B is an exemplary flow diagram illustrating an alternative embodiment of the method for monitoring uterine contractions of FIG. 5A.

To improve the robustness of the method, FIG. 5B shows an alternative embodiment of the method 100 for monitoring uterine contractions of FIG. 1 and FIG. 5A, wherein the output of analyzing, at 140, UC signals is used in processing, at 220, UEMG signals to extract UEMG markers. For instance, contractions detected through the analysis of UC signals can be used to define the excerpt of the UEMG signals on which the UEMG markers can be extracted. Processing, at 220, the UEMG signals to extract the UEMG markers can then provide a finer and more detailed analysis of the contraction, wherein the finer time, frequency and time-frequency features can be extracted to provide a complete characterization of the contraction. Advantageously, the finer characterization can either provide new information, and/or be used to improve the accuracy and the robustness of classifying, at 230, contraction type.

Figure 6:
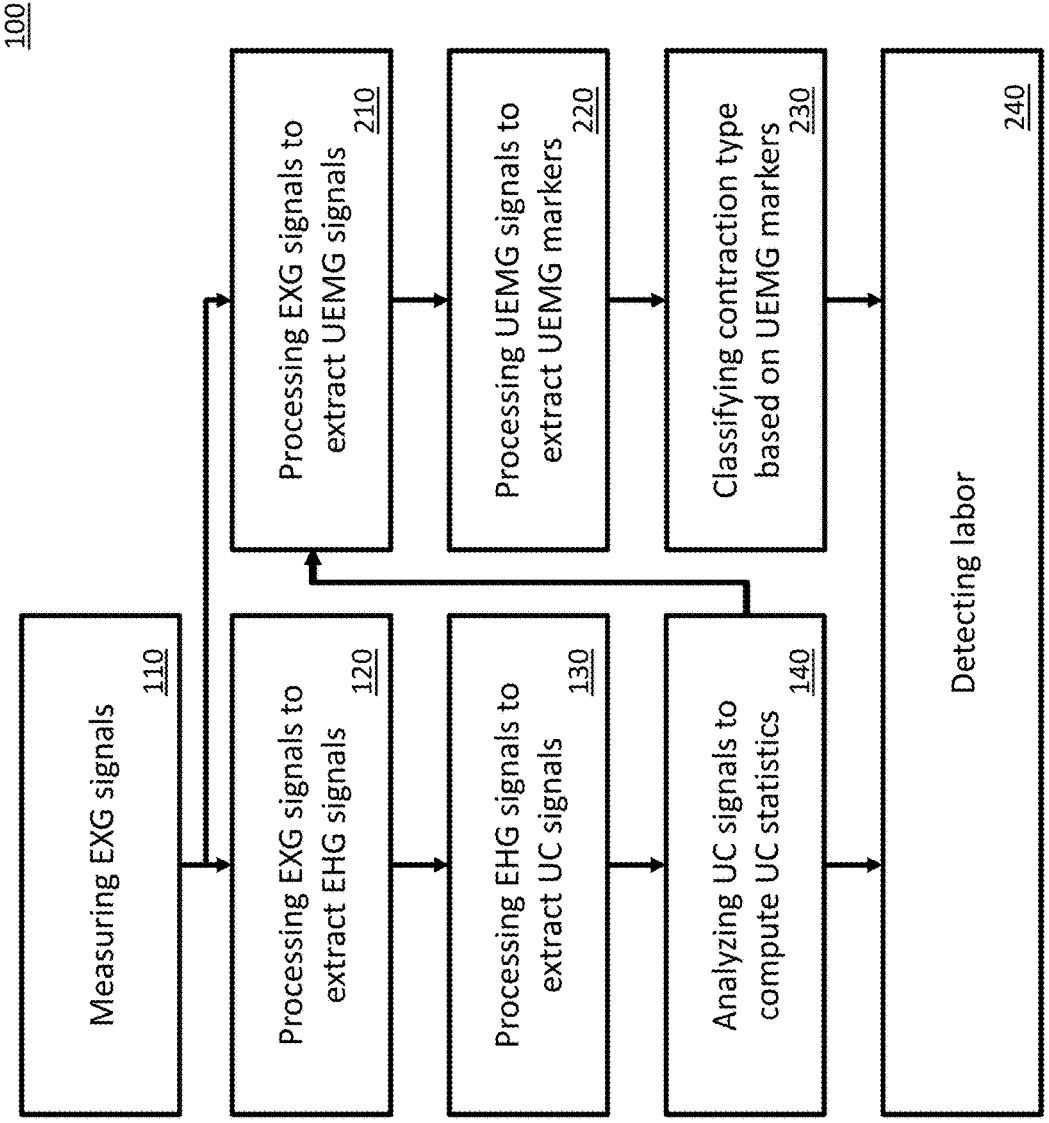
FIG. 6 is an exemplary flow diagram illustrating an alternative embodiment of the method for monitoring uterine contractions of FIG. 5A or FIG. 5B.

FIG. 6 shows another alternative embodiment of the method 100 for monitoring uterine contractions of FIG. 5A or FIG. 5B, wherein the method 100 for monitoring uterine contractions can further include detecting labor, at 240. Detecting labor, at 240, can use the UC statistics determined by analyzing, at 140, UC signals and/or the contraction type determined by classifying, at 230, contractions to detect whether a pregnant woman has gone into labor. Providing that an estimation of the gestational age can be available, detecting labor can also be used to detect onset of preterm labor, defined as labor starting before 37 weeks of gestational age.

Figure 7:
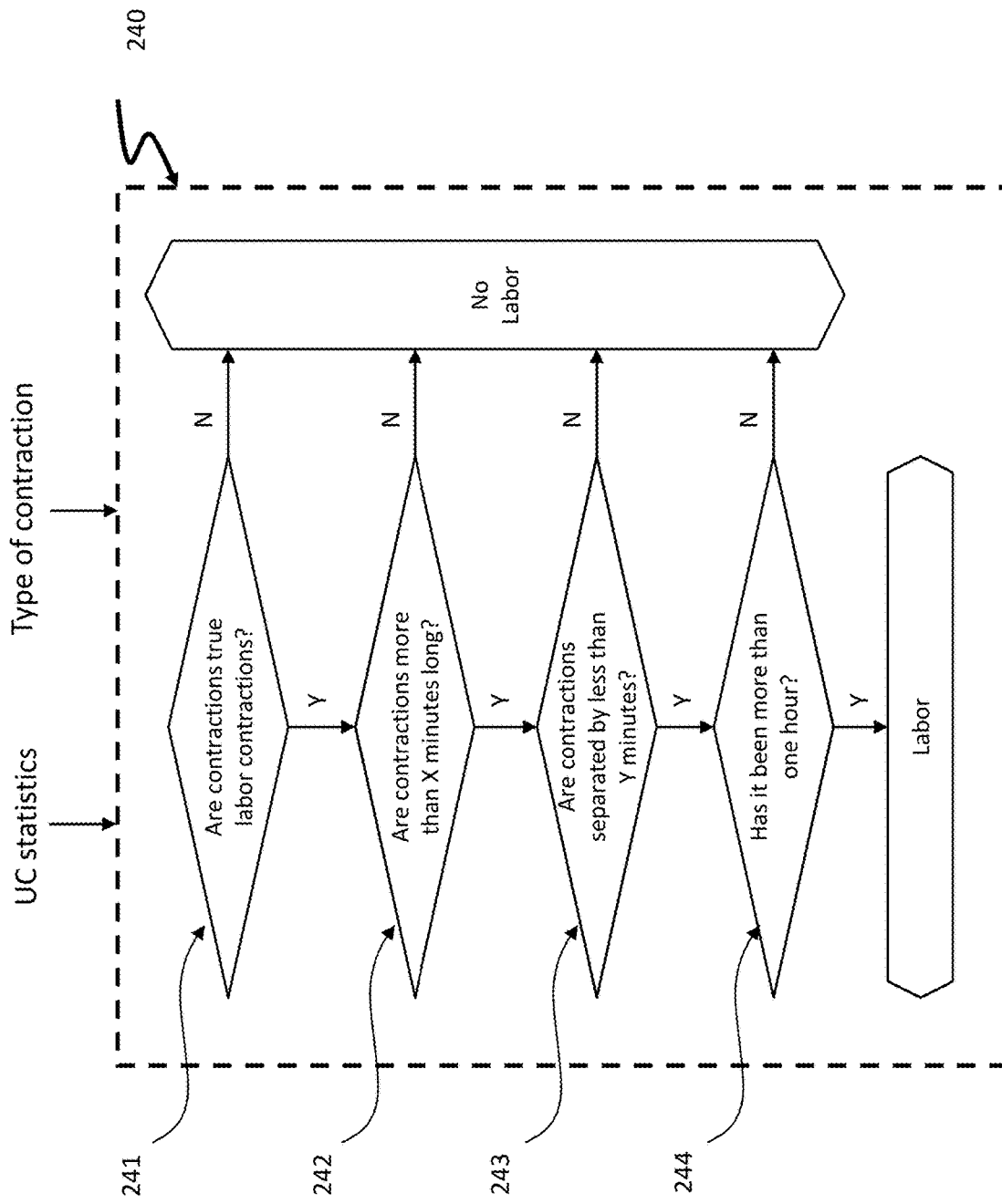
FIG. 7 is an exemplary flow diagram illustrating an alternative embodiment of the method for monitoring uterine contractions of FIG. 6.
Figure 24:
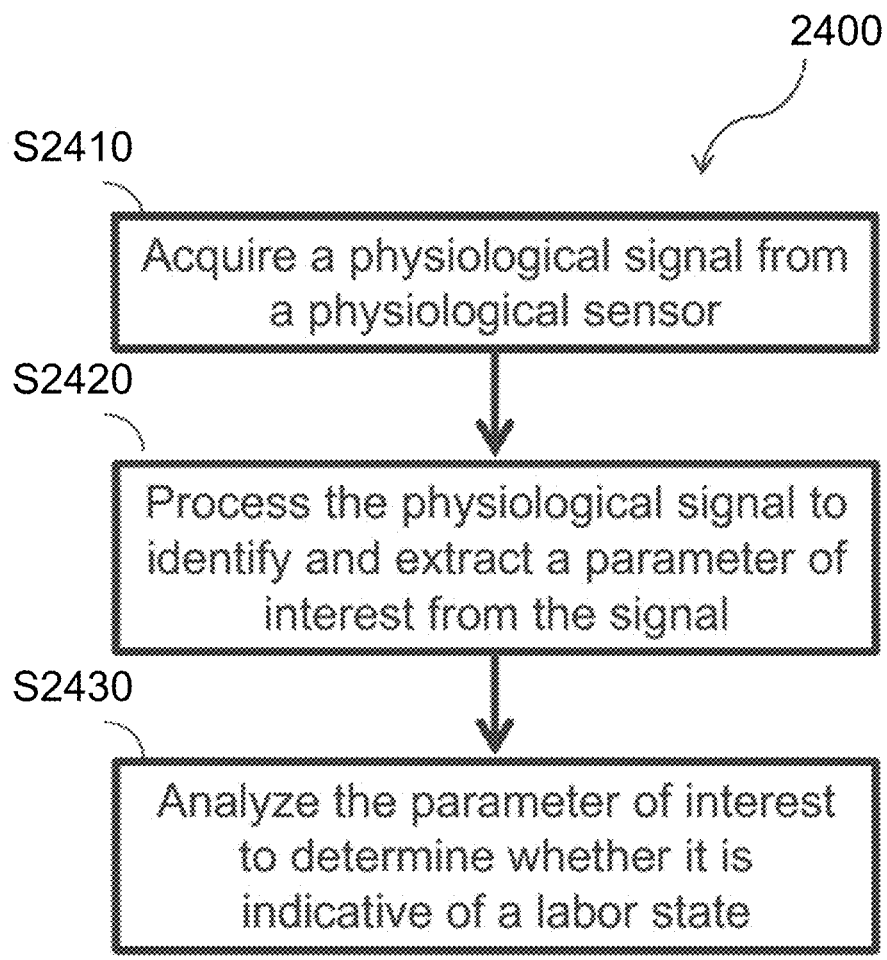
FIG. 24 is an exemplary flow diagram illustrating one embodiment of a method for identifying a labor state in a pregnant female.

Detecting labor, at 240, can be achieved using analytics methods that include but are not limited to decision trees, conditional logic, support vector machines, artificial neural networks, Bayesian networks, Markov chains, hierarchical model, etc. In one example, detecting labor, at 240, can be implemented according to common pregnancy practice such as the "411" rule, according to which a pregnant woman should go to the hospital for labor if she is having contractions at least every four minutes, of at least one minute duration, and for at least one hour. Preferably, the "411" rule can be combined with an assessment of the type of contractions, to ensure that the contractions that are detected are true labor contraction and not Braxton Hicks contractions or any other physiological phenomena. FIG. 7 illustrates an exemplary embodiment of detecting labor, at 240, of FIG. 6, wherein detecting labor, at 240, can be achieved using a decision tree based on the UC statistics and contraction type. Turning to FIG. 7, the decision tree can take the UC statistics and the contraction type as input, to output the status of labor, namely "labor" or "no labor". As illustrated on FIG. 7, detecting labor, at 240, can include: determining, at 241, whether the contraction type corresponds to true labor contractions; determining, at 242, whether contractions are at least X minute long; determining, at 243, whether contractions are separated by at least Y minute; and determining, at 242, whether this has happened for at least Z hour In one particular example, X=1, Y=4 and Z=1, implementing the "411 rule" well known to pregnancy care experts. Additional methods for detecting a labor state or determining a labor status are described elsewhere herein, at least for example in FIGS. 24-26.

During pregnancy, contractions are known to prepare the body of the pregnant woman for labor and delivery. Painful and frequent contractions may however be problematic as they may lead to early delivery and possibly to preterm birth, with dramatic consequence for the baby. There is today very limited knowledge available on the relationship between lifestyle behaviors of a pregnant woman and the number, frequency, duration, and intensity of her contractions. Stated somewhat differently and more generally, there is limited information on the relationship between lifestyle behaviors and contraction profiles. An important lifestyle behavior known to have impact on pregnancy outcomes is maternal stress.

Figure 8:
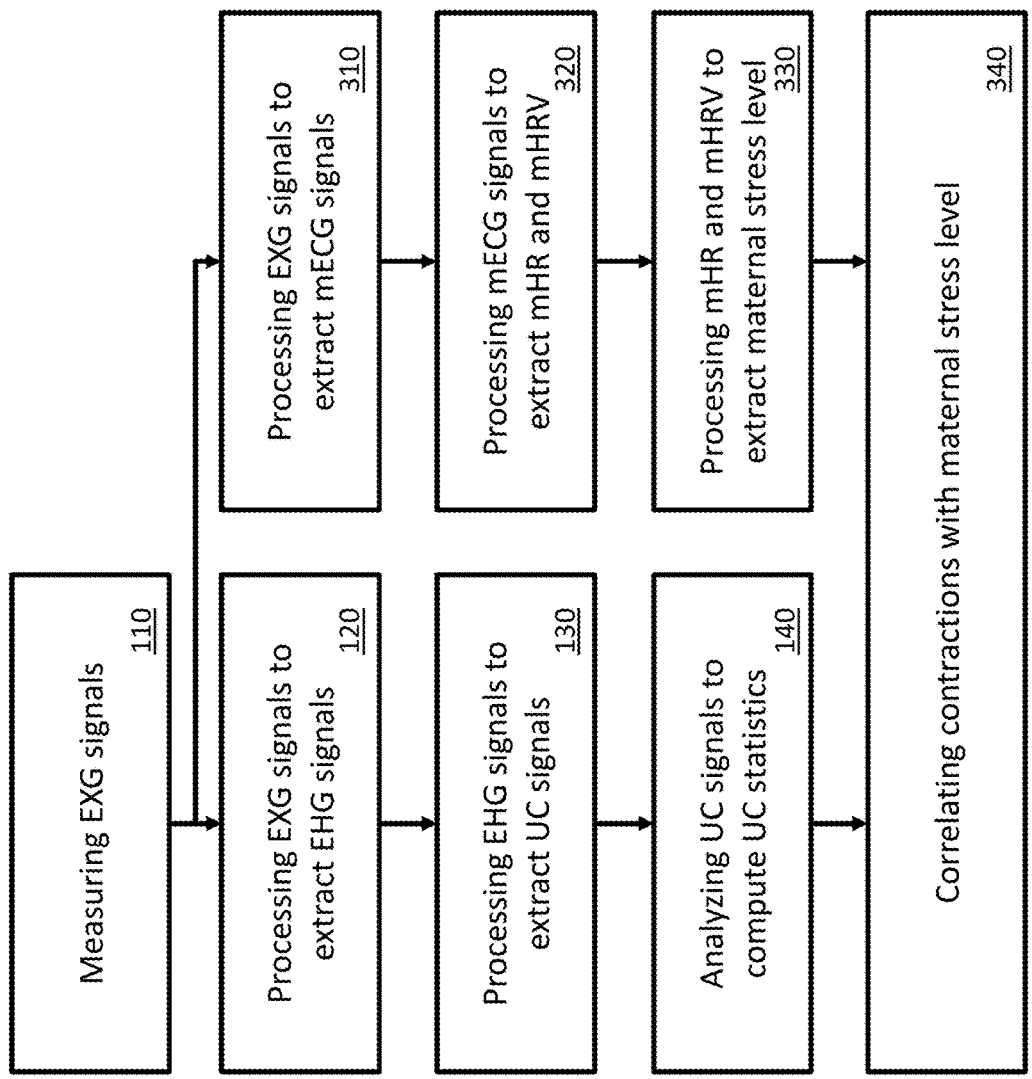
FIG. 8 is an exemplary flow diagram illustrating yet another alternative embodiment of the method for monitoring uterine contractions of FIG. 1.

Maternal stress can be extracted from heart rate variability. Information about heart rate variability is carried in the EXG signals measured according to the method 100 for contraction monitoring of FIG. 1. Therefore, it is possible, by extending the method 100 for contraction monitoring of FIG. 1, to advantageously measure maternal stress and correlate the maternal stress with the contraction profile. FIG. 8 shows yet another alternative embodiment of the method 100 for monitoring uterine contractions of FIG. 1, wherein the method 100 for monitoring uterine contraction can further include: processing, at 310, EXG signals to extract maternal ECG (mECG) signals; processing, at 320, mECG signals to extract maternal heart rate (mHR) and maternal heart rate variability (mHRV); processing, at 330, mHR and mHRV to extract maternal stress level; and correlating, at 340, contractions with maternal stress level.

Processing, at 310, EXG signals to extract mECG signals comprises isolating from the EXG signals a part of the EXG signals that is relevant to the maternal electrocardiogram, and separating it out from a part of the EXG that is related to other physiological phenomena, noise, artifacts, and any other contributions. Processing, at 310, EXG signals to extract mECG signals can be achieved using signal processing techniques including, but not limited to, time-domain filtering, frequency-domain filtering, time-frequency-domain filtering, and/or blind source separation.

Processing, at 320, mECG signals to extract mHR and mHRV comprises analyzing the mECG signals to extract mECG fiducial points, in particular the mECG R-wave (also called R-peak), from which RR intervals, instantaneous mHR, and mHRV can be calculated. Example of signal processing techniques to detect the R-wave from the mECG signals can include, but are not limited to: averaging, derivative filters, linear filters, band-pass filters, continuous wavelet, discrete wavelet, template matching, etc. Instantaneous mHR can be computed from the distance between two successive R-waves. mHRV can then be computed from the variations in heart rate. mHRV can be calculated using time-based or frequency-based statistical features. Preferably, the R-waves can be detected using continuous wavelet transform, for example using a Mexican hat or Daubechies wavelet. The mECG signals can then be processed with a wavelet filter, and a threshold is applied on the output of the wavelet filter to detect possible R-wave candidates. All R-wave candidates are then filtered and only the one with the highest energy within a certain time window, for example 1 second, is kept as the R-wave. This process filters out other ECG waves (e.g., T-wave) and/or artifacts.

Processing, at 330, mHR and mHRV to extract maternal stress can be achieved by combining mHR, mHRV, and/or trends and deviations in mHR or mHRV to obtain a measurement of the autonomic nervous system that is associated to stress. In a further embodiment (not shown), processing, at 330, mHR and mHRV to extract maternal stress using context information coming from a user device, e.g. a smart phone, to improve the accuracy and reliability of the stress estimation. Accuracy can be improved by identifying context in which mHR and mHRV are most likely linked to the activation of the autonomic nervous system, as opposed to an increase in physical activity for instance. Context can be obtained from user activity and/or user daily routines. Daily routines can be estimated from the user low-level activity and/or location.

Correlating, at 340, contractions with maternal stress level can be achieved by looking at correlation between the maternal stress level on one end, and UC statistics and/or contraction type on the other end. Correlating, at 340, contractions with maternal stress level can advantageously provide new insights on how maternal stress level may affect contractions. For example, a woman may be able to discover that she has more contractions when her stress level is higher.

Figure 9A:
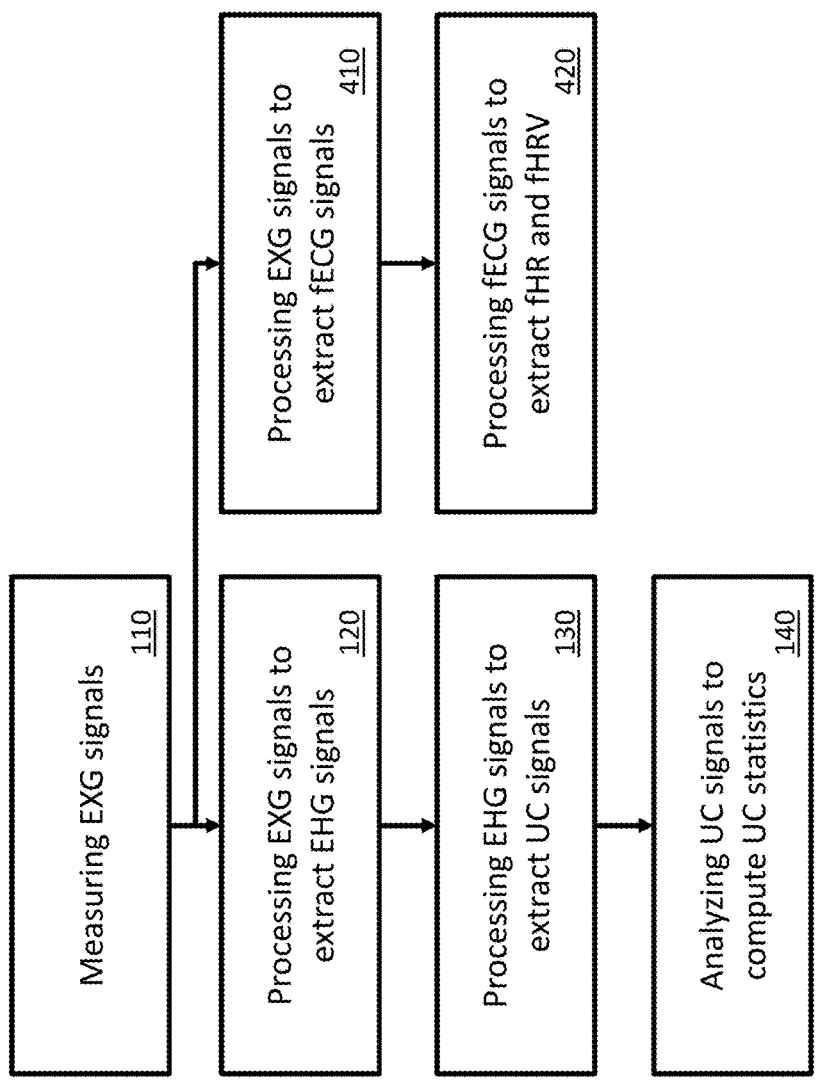
FIG. 9A is an exemplary flow diagram illustrating yet another alternative embodiment of the method for monitoring uterine contractions of FIG. 1.

FIG. 9A shows yet another alternative embodiment of the method 100 for monitoring uterine contractions of FIG. 1, wherein the method 100 for monitoring uterine contraction can further include: processing, at 410, EXG signals to extract fetal ECG (fECG) signals; and processing, at 420, fECG signals to extract fetal heart rate (fHR) and fetal heart rate variability (fHRV).

Processing, at 410, EXG signals to extract fECG signals comprises isolating from the EXG signals the part of the EXG signals that is relevant to the fetal electrocardiogram, and separating it out from the part of the EXG that is related to other physiological phenomena, noise, artifacts, and any other contributions. Processing, at 410, EXG signals to extract fECG signals can be achieved using signal processing techniques including, but not limited to, template matching, averaging, time-domain filtering, frequency-domain filtering, time-frequency-domain filtering, and/or blind source separation.

Processing, at 420, fECG signals to extract fHR and fHRV comprises analyzing the fECG signals to extract fECG fiducial points, in particular the fECG R-wave (also called R-peak), from which RR intervals, instantaneous fHR, and fHRV can be calculated. Example of signal processing techniques to detect the R-wave from the fECG signals can include, but are not limited to: averaging, derivative filters, linear filters, band-pass filters, continuous wavelet, discrete wavelet, template matching, etc. Instantaneous fHR can be computed from the distance between two successive R-waves. fHRV can then be computed from the variations in heart rate. fHRV can be calculated using time-based or frequency-based statistical features.

Figure 9B:
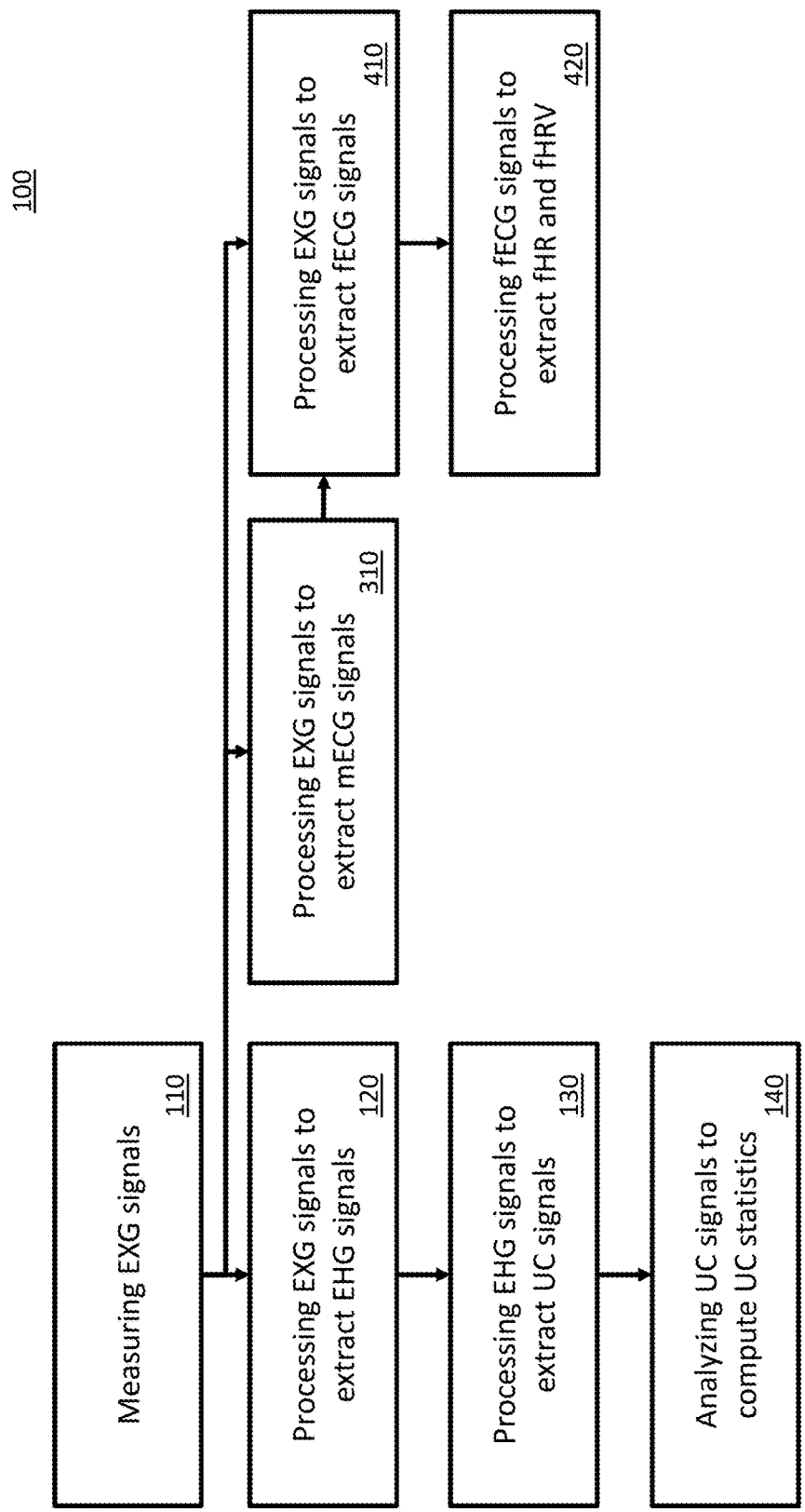
FIG. 9B is an exemplary flow diagram illustrating an alternative embodiment of the method for monitoring uterine contractions of FIG. 9A.

FIG. 9B shows an alternative embodiment of the method 100 for monitoring uterine contractions of FIG. 9A, wherein processing, at 410, EXG signals to extract fetal ECG (fECG) signals can take the mECG signal as input. The mECG signals can be used in processing the EXG signals to filter the mECG signals from the fECG signals, therefore improving the signal-to-noise ratio on the fECG signals. Preferably, processing, at 410, EXG signals to extract fECG signals can include adaptive filtering, wherein the EXG signals and the mECG signals can be used as an input to the adaptive filter. The mECG signals can be used as the input to an adaptive filter representing an estimation of the noise on the fECG signals. The adaptive filter can then function to remove the noise estimation from the EXG signals, or in other words to remove the mECG from the EXG signals, yielding a cleaner version of the EXG signals with a reduced contribution of the mECG signals. The cleaner EXG signals can then be further processed using the method of FIG. 9A.

Figure 9C:
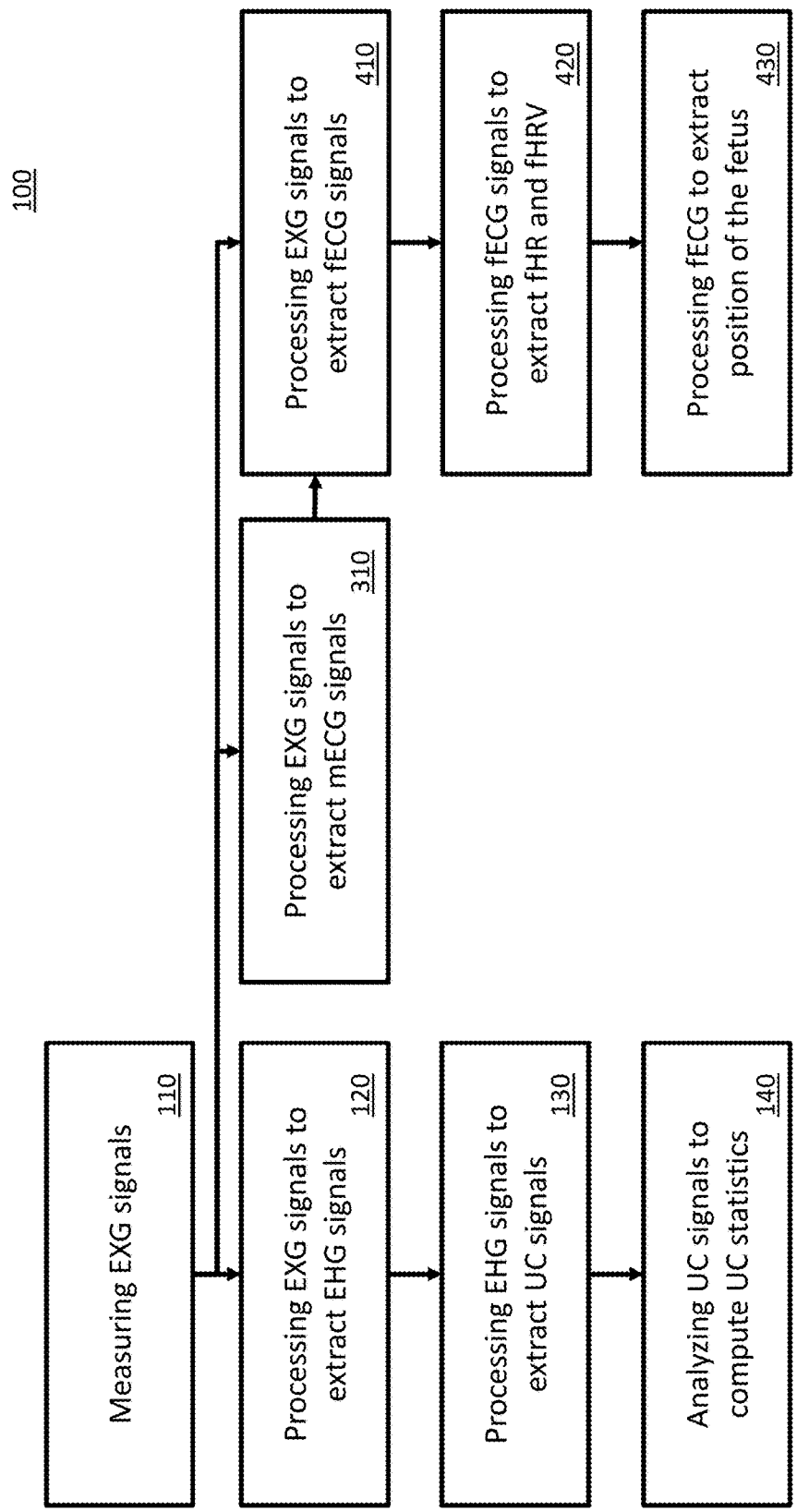
FIG. 9C is an exemplary flow diagram illustrating an alternative embodiment of the method for monitoring uterine contractions of FIG. 9A or FIG. 9B.

FIG. 9C shows an alternative embodiment of the method 100 for monitoring uterine contractions of FIG. 9A or FIG. 9B, wherein the method 100 for monitoring uterine contraction can further include processing, at 430, fECG to extract position of the fetus. Processing, at 430, fECG to extract position of the fetus can be done advantageously by exploiting the fact that the morphology of the fECG is affected by the relative position of the fetus from the measurement electrodes.

Figure 9D:
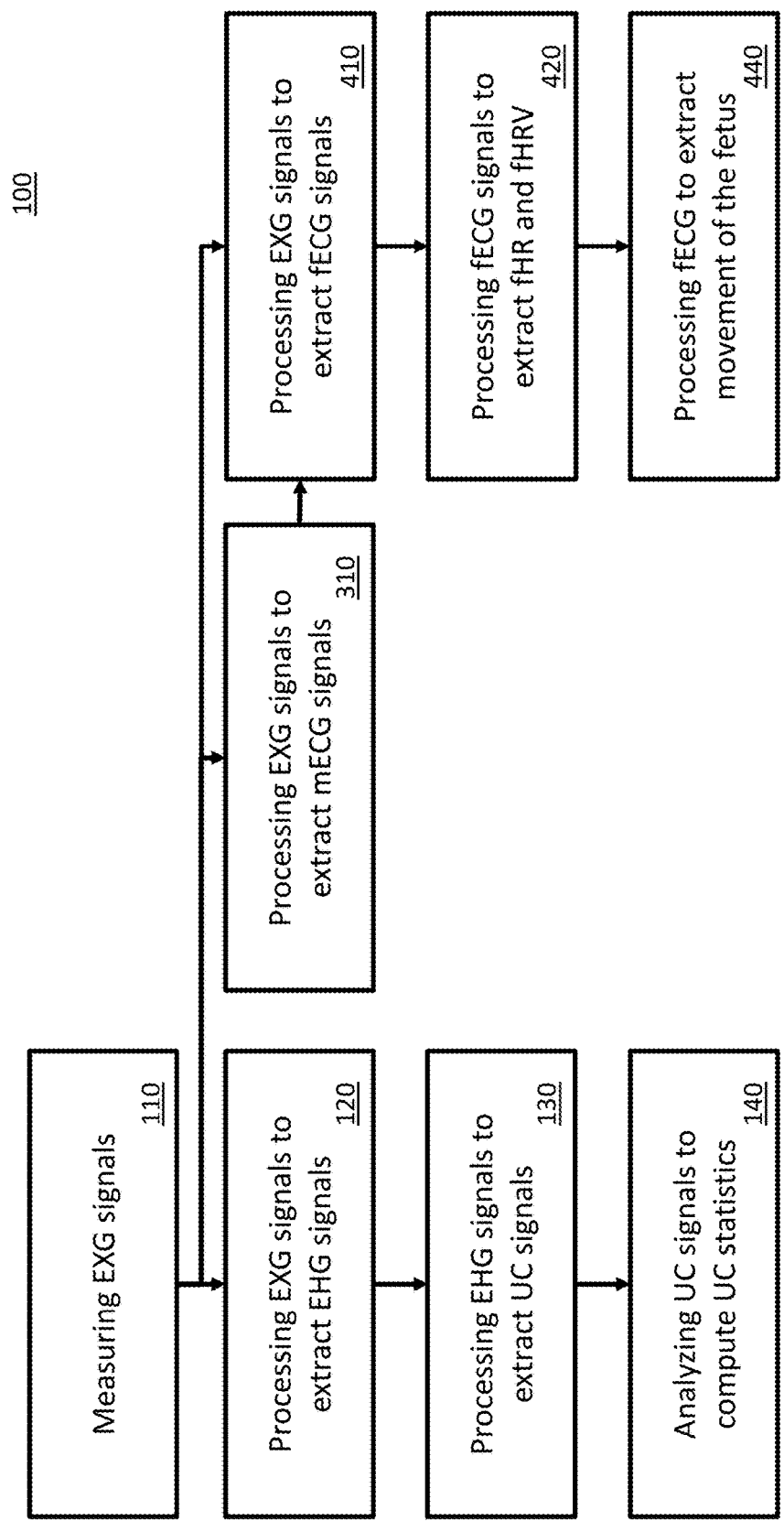
FIG. 9D is an exemplary flow diagram illustrating another alternative embodiment of the method for monitoring uterine contractions of FIG. 9A or FIG. 9B.

FIG. 9D shows an alternative embodiment of the method 100 for monitoring uterine contractions of FIG. 9A or FIG. 9B, wherein the method 100 for monitoring uterine contraction can further include processing, at 440, fECG to extract movement of the fetus. Processing, at 440, fECG to extract position of the fetus can be done advantageously by exploiting the fact that the morphology of the fECG is affected by the relative movement of the fetus from the measurement electrodes.

For example, fetal movement detection may be based on variations in an amplitude (i.e., the difference between the value at the R-peak position and the mean of the Q- and S-peaks) of the fetal QRS complex. The fetal ECG waveform changes as a result of a displacement of the cardiac vector with respect to the measurement electrodes on an abdomen of the mother. A change in fetal QRS-wave height and shape, which is dependent on rotational and translational movement of the fetus, may indicate thoracic movement and ultimately fetal motility. Fetal movement may be categorized into one of several categories, for example: major fetal movement (i.e., simultaneous movement of multiple limbs or head, turning of thorax, other large movements, etc.), minor fetal movement (i.e., small or intermittent movement of one of the limns or the head, etc.), fetal respiration (i.e., clear and sustained fetal breathing or hiccups, etc.), and fetal rest. Movement may be further based on a predetermined length of movement, for example 5 seconds.

Further, detection of fetal movement may further require band pass filtering the signal between 1-95 Hz to remove out-of-band noise and interference. Additionally, a band-stop filter around 50 Hz, with cut-off frequencies of 49 Hz and 51 Hz, is applied to remove power-line interference. For removing maternal QRS peaks, maternal R-peaks are removed by identifying each R-peak and an interval around each peak (e.g., +/−90 ms). Each identified R-peak and interval are blanked before fetal QRS peak identification.

Figure 10:
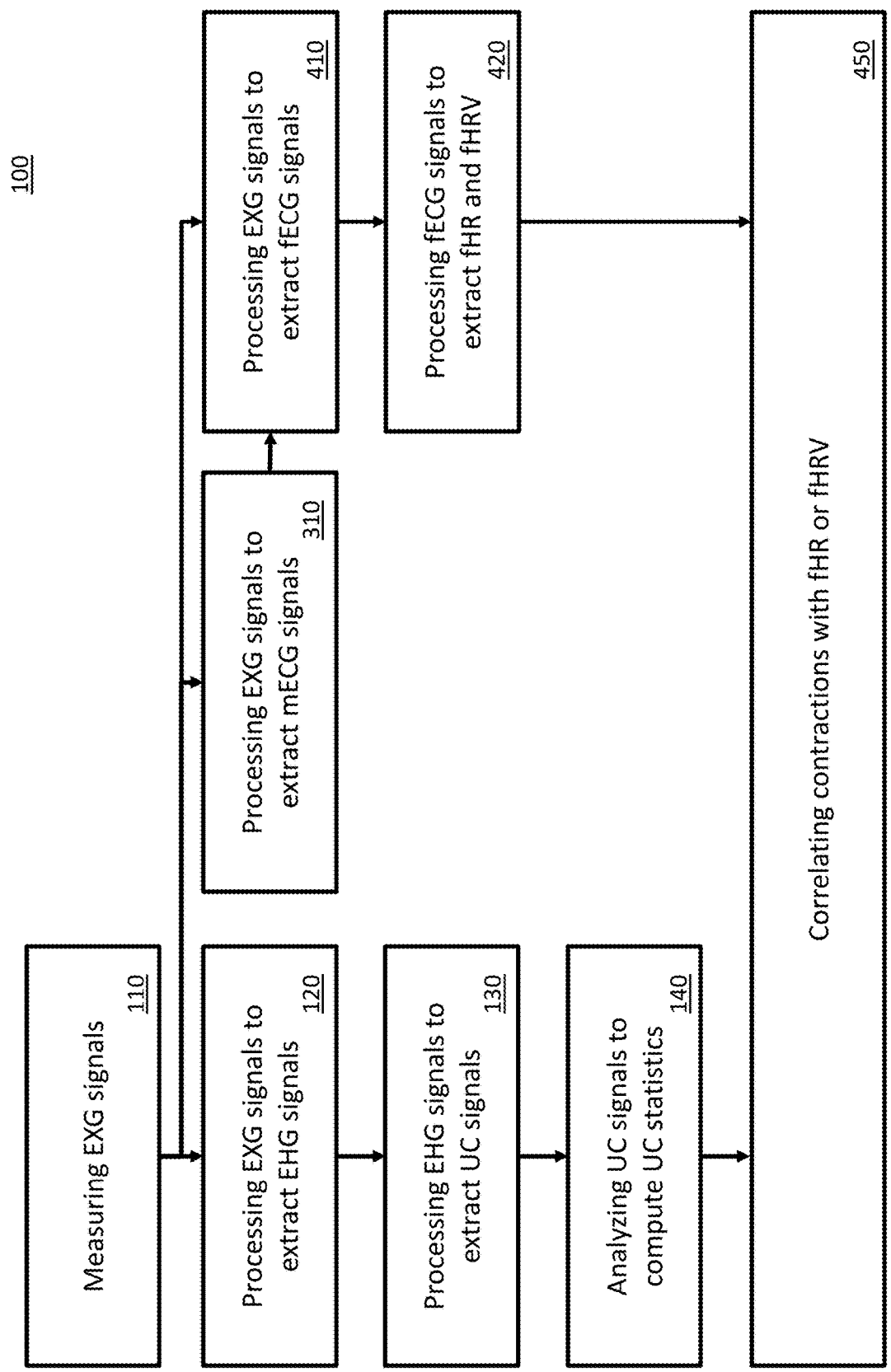
FIG. 10 is an exemplary flow diagram illustrating yet another alternative embodiment of the method for monitoring uterine contractions of FIG. 9A or FIG. 9B.

FIG. 10 shows yet another alternative embodiment of the method 100 for monitoring uterine contractions of FIG. 9A or FIG. 9B, wherein the method 100 for monitoring uterine contraction can further include correlating, at 450, contractions with the fHR or fHRV. Correlating, at 450, here can correspond to visualizing the UC signals and the fHR signals on two synchronized graphs positioned on top of each other. The fHR changes during a contraction can provide insights on the fetus response to the contractions and therefore can carry important information regarding the health status of the fetus. Advantageously, the method 100 for monitoring uterine contraction of FIG. 10 can simultaneously extract, from the only measurement of EXG signals, contractions and fHR, thus providing all the information necessary to perform the clinical standard non-stress test with an extreme simplicity of use that can be performed in any locations including the home. Preferably, this information can then be shared remotely with a clinical trained staff, who can interpret the data.

Figure 11:
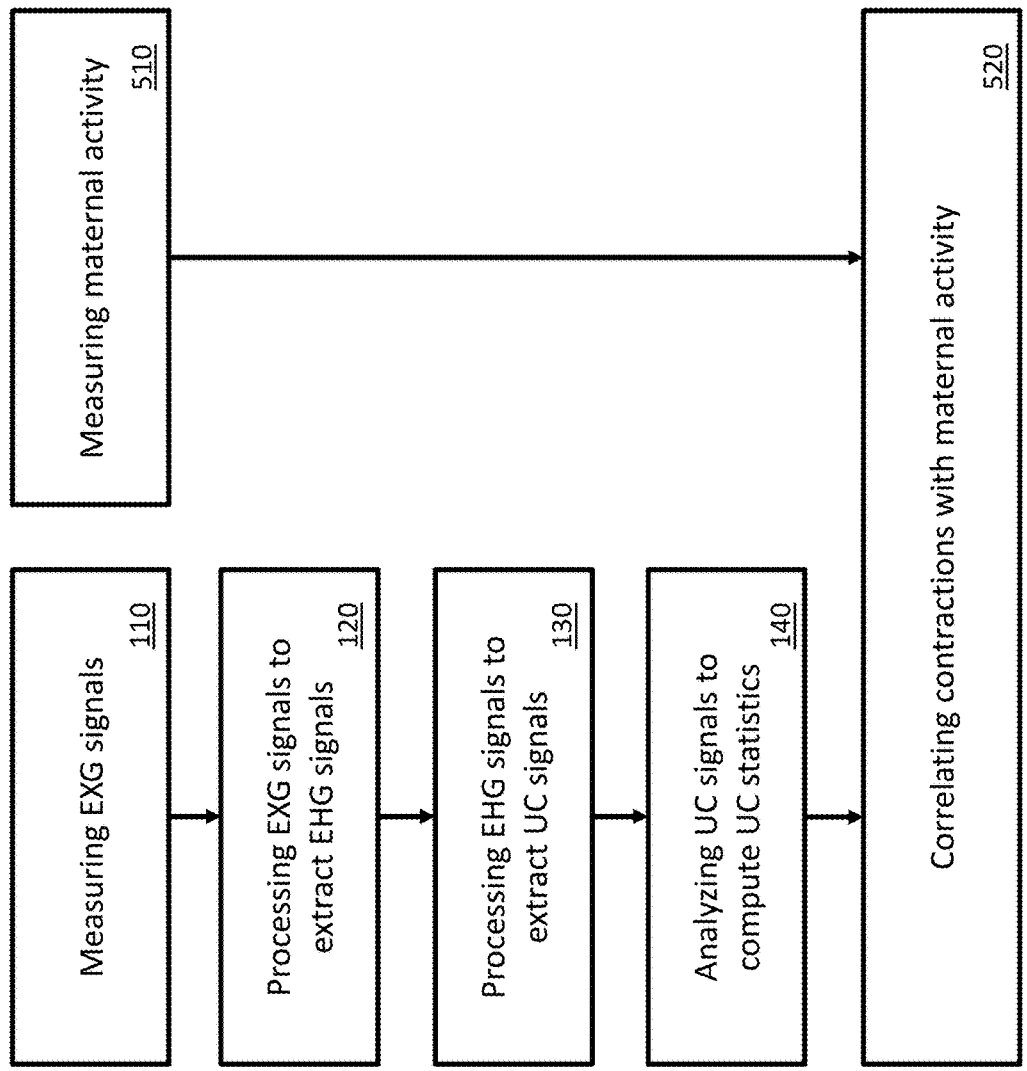
FIG. 11 is an exemplary flow diagram illustrating yet another alternative embodiment of the method for monitoring uterine contractions of FIG. 1.

FIG. 11 shows yet another alternative embodiment of the method 100 for monitoring uterine contractions of FIG. 1, wherein the method 100 for monitoring uterine contraction can further include: measuring, at 510, maternal activity; and correlating, at 520, contractions with maternal activity.

Measuring, at 510, maternal activity can be achieved using an activity sensor embedded in a smartphone, using a dedicated activity tracker or using an activity sensor embedded in the contraction monitor. Activity measures can include, but are snot limited to: steps, activity time, activity types, time spent in different activity types, energy expenditure, calorie burned, sleep duration, sleep quality. The activity sensor can track maternal activity over time, for specific recording sessions, or continuously and 24/7.

Correlating, at 520, contractions with maternal activity can be achieved by looking at correlation between maternal activity levels on one end, and UC statistics and/or contraction type on the other end. Correlating, at 520, contractions with maternal activity can advantageously provide new insights on how maternal activity may affect contractions. For example, a woman may be able to discover that she has more contractions when she is more active or decrease when she is less active or sleeping or more active at night if she has been active during the day.

Figure 12:
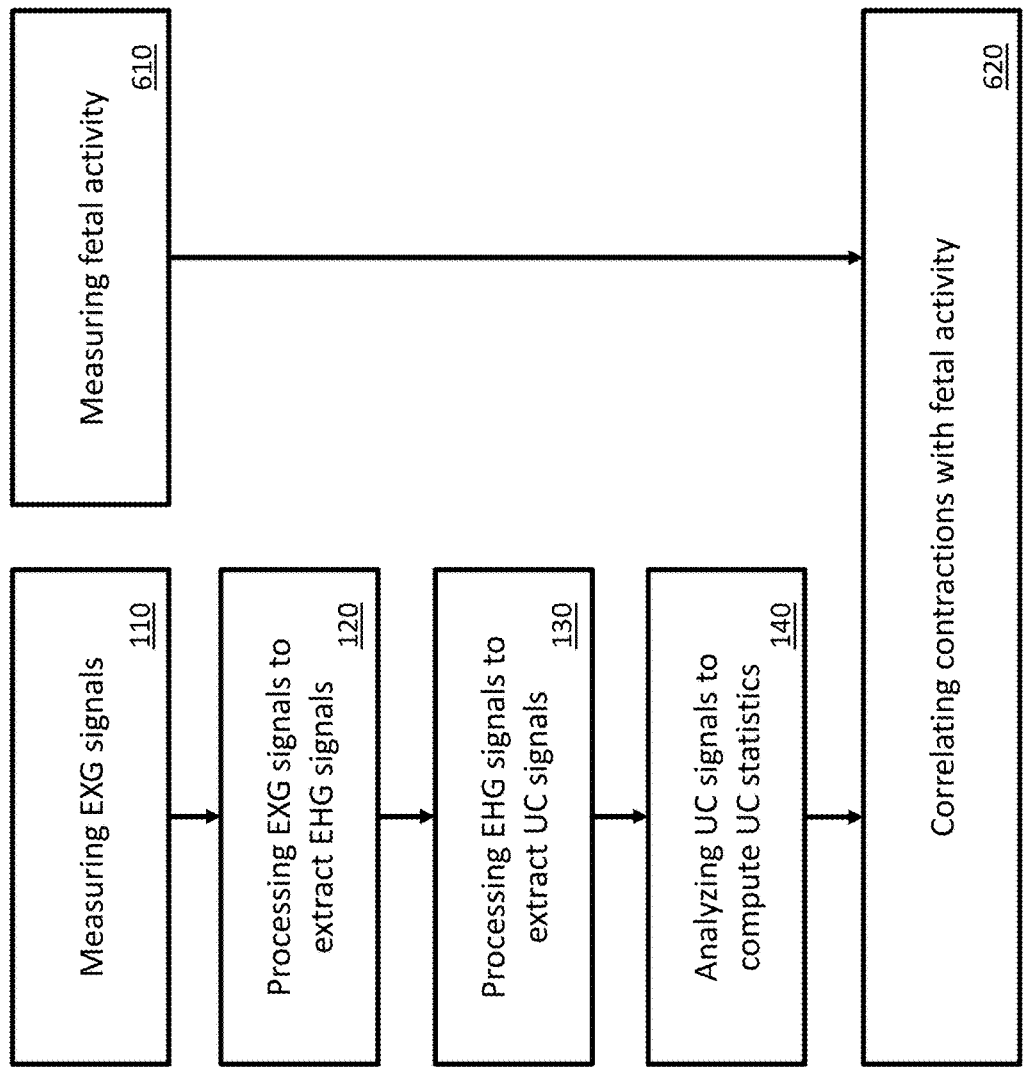
FIG. 12 is an exemplary flow diagram illustrating yet another alternative embodiment of the method for monitoring uterine contractions of FIG. 1.

FIG. 12 shows yet another alternative embodiment of the method 100 for monitoring uterine contractions of FIG. 1, wherein the method 100 for monitoring uterine contraction can further include: measuring, at 610, fetal activity; and correlating, at 620, contractions with fetal activity.

Measuring, at 610, fetal activity can be achieved using the method of FIG. 9D. Alternatively or additionally, fetal activity can be measured, at 610, using an accelerometer positioned on a woman's abdomen. Advantageously, fetal activity can be measured, at 610, using a combination of the method of FIG. 9D and accelerometers. This is advantageous because the method of FIG. 9D may be more accurate in detecting overall movement of the fetus, whereas accelerometer-based fetal activity measurement may be more accurate for localized fetus movement such as kicks. Combining both methods therefore can allow detecting both overall and local fetal movements. Fetal activity can be measured, at 610, during specific recording sessions, or continuously and 24/7.

Correlating, at 620, contractions with fetal activity can be achieved by looking at correlation between fetal activity levels on one end, and UC statistics and/or contraction type on the other end. Correlating, at 620, contractions with maternal activity can advantageously provide new insights on how fetal activity is related to contractions. For example, a woman may be able to discover that her baby is less active when she has contractions.

In yet another alternative embodiment (not shown) of the method 100 for monitoring uterine contractions of FIGS. 5A-12, wherein the method 100 for monitoring uterine contraction can further include providing user feedback. Providing user feedback can provide recommendations or suggestions to the pregnant woman based on the UC statistics determined by analyzing, at 140, UC signals and/or the contraction type determined by classifying, at 230, contractions. User feedback can be provided to help women reduce the pain associated with contractions, or to attempt to reduce the number or the frequency of contractions. User feedback can for example include recommendations for a better body position, for specific food, for specific activities (e.g. take a warm bath), etc. In a further embodiment, providing user feedback can provide recommendations or suggestions to the pregnant woman based on the correlation between contractions and maternal stress level, computed at 340. For example, if an elevated number of contractions and an elevated stress level are detected simultaneously, feedback can be provided to the woman to watch her stress level and to try to relax. The feedback can also include tips to help the user relax, or exercises that the user may be able to do to decrease her stress level. In a further embodiment, providing user feedback can provide recommendations or suggestions to the pregnant woman based on the correlation between contractions and maternal activity, computed at 520. For example, if an elevated number of contractions and an elevated activity level are detected simultaneously, feedback can be provided to the woman to reduce her activity and relax for a few days. The user feedback can take the form of a message displayed in an App for smartphone, tablets, smart watch, or smart glasses, or a text message sent to the mother. Alternatively or additionally, the feedback can take the format of a message, graph, picture, figure, or any multimedia messages transmitted to the partner, family, or friends of the pregnant women. Alternatively or additionally, the user feedback can take the form of a report with graphs, tables or text, sent to an obstetrician or a clinically trained staff for further interpretation.

According to the method 100 for monitoring uterine contractions of FIGS. 5A-12, the data collected can include at least one of UC statistics, contraction type, mHR, mHRV, maternal stress, fHR, hHRV, or maternal activity. In yet another alternative embodiment, the data collected using the method 100 for monitoring uterine contractions can be used to stratify pregnant woman in different patient categories, based on their lifestyle and/or physiological profiles. In a further embodiment, the data collected using the method 100 for monitoring uterine contractions can be used identify possible risk factors for pregnancy complications or negative outcomes. Pregnancy complications may include hypertension, gestational hypertension, gestational diabetes, preeclampsia, etc. Negative pregnancy outcomes may include preterm birth, low birth weight, stillbirth, etc.

Figure 13:
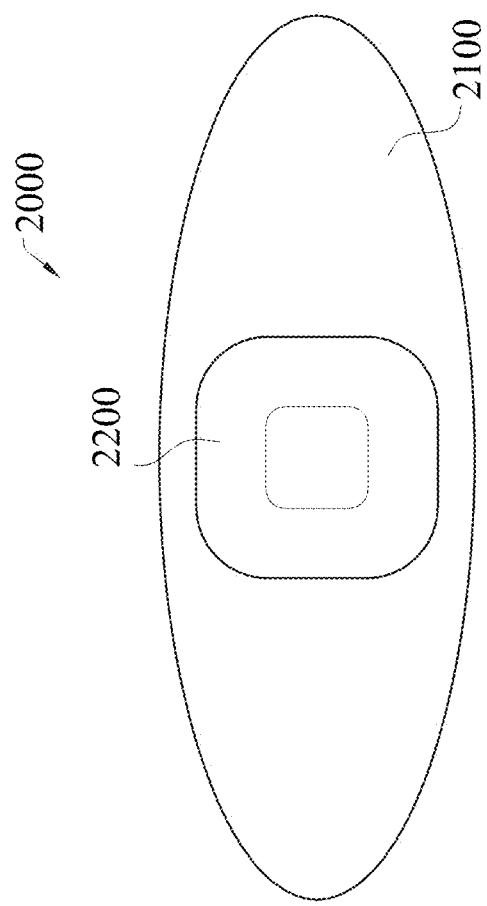
FIG. 13 shows an exemplary illustration of one embodiment of the device for contraction monitoring.

The method 100 for uterine contraction monitoring can be achieved, according to one embodiment disclosed herein, by the device 2000 for contraction monitoring illustrated in FIG. 13.

Turning to FIG. 13, the device 2000 for contraction monitoring comprises an electrode patch 2100 and a sensor module 2200, advantageously combined to monitor at least one channel of uterine contraction signals. The electrode patch 2100 and the sensor module 2200 may be in one part or may be made of two separate parts. The two separate parts can be provided with a mechanical and electrical system for attaching one to the other, such as a clipping system, a magnet, etc. Other embodiments are described elsewhere herein.

Figure 14:
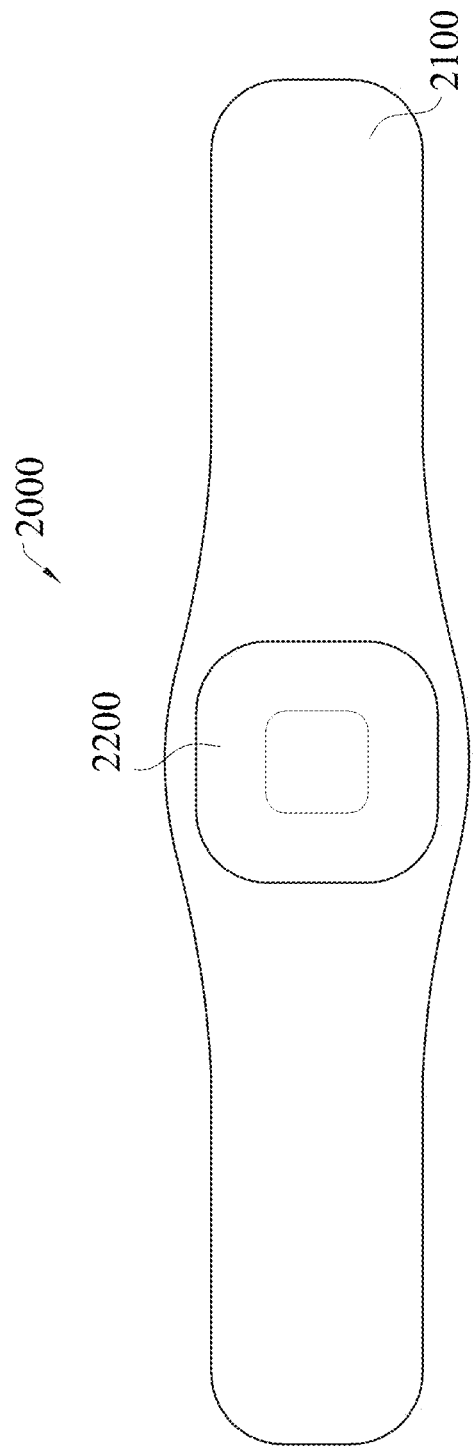
FIG. 14 shows an exemplary illustration of another embodiment of the device for contraction monitoring.

FIG. 14 illustrates another embodiment of the device 2000 for contraction monitoring. By comparing FIG. 13 and FIG. 14, one will easily understand that the electrode patch 2100 or the sensor module 2200 can take many different form factors.

Stated somewhat differently, the device 2000 for contraction monitoring can take many different shapes, sizes, colors, materials, and levels of conformability to the body. The device 2000 may or may not take the form of a plaster. For example, the device 2000 may be integrated in a piece of garment. In some embodiments, the device 2000 may take the form of a piece of clothing or textile. In some embodiments, the device 2000 may take the form of a belt that is worn around the abdomen. For the last three examples, the electrode patch 2100 may be an integral part of the piece of garment, clothing, or belt, or may be attached to such piece of garment, clothing, or belt.

Figure 15:
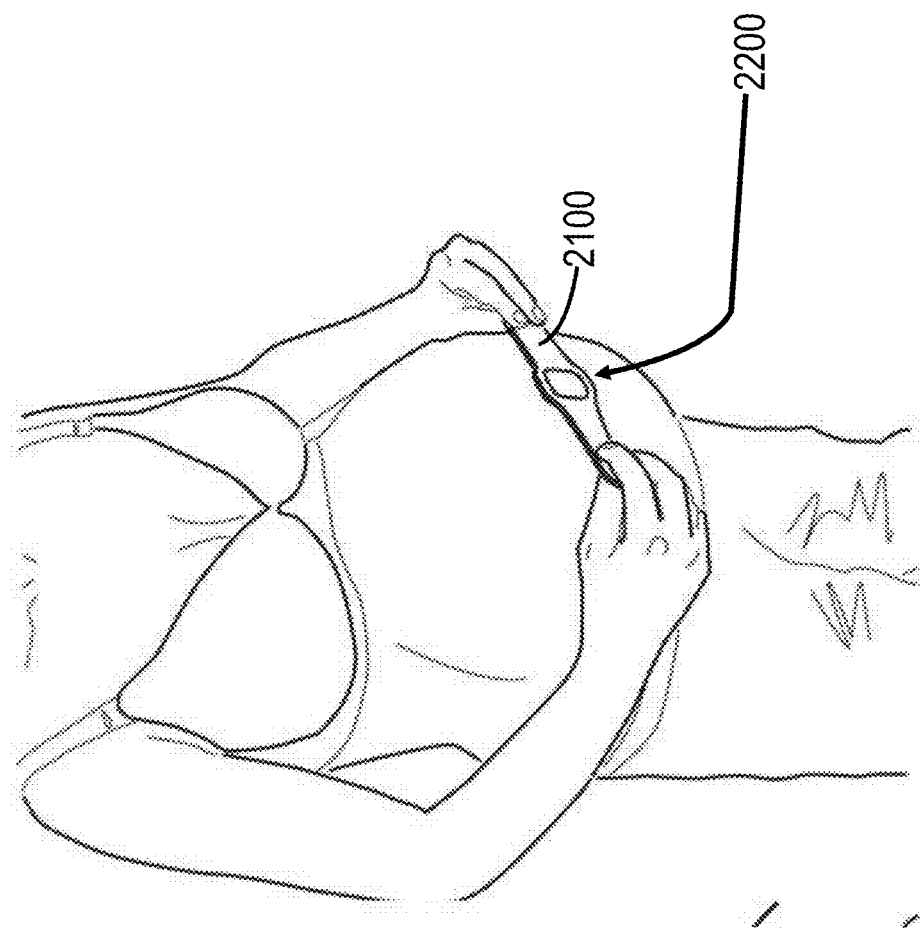
FIG. 15 shows an exemplary illustration of yet another embodiment of the device for contraction monitoring of FIG. 13.

FIG. 15 shows an exemplary embodiment of the contraction monitoring device 2000, wherein the electrode patch 2100 and the sensor module 2200 can be integrated and encapsulated into one unique part solely making the device 2000. Preferably, the contraction monitoring device 2000 of FIG. 15 can have at least three electrodes, including one measurement electrode located on one extremity of the device, one reference electrode located on the other extremity of the device, and one bias electrode in the middle. Such configuration enables the measurement of one channel EXG signal, along the horizontal direction. In some embodiments, the device 2000 of FIG. 15 can have 4 electrodes, two measurement electrodes located on the two extremities, one reference electrode located in the middle of the device, and one bias electrode located between a measurement electrode and the reference electrode. Advantageously, a variant of the device 2000 of FIG. 15 (not shown) can have 5 electrodes, two measurement electrodes located on the two extremities of the device, one reference electrode located in the middle of the device 2000, one additional measurement electrode located below the reference electrode, at 90 degrees from the line between the first three electrodes, and one bias electrode located between a measurement electrode and the reference electrode. Such configuration enables the measurement of two channel EXG signals, one along the horizontal direction and one along the vertical direction. In a further exemplary embodiment, the device 2000 can be attached to the body using an adhesive layer. In another embodiment, the adhesive layer can be replaced by the user. In another exemplary embodiment, the device 2000 can be attached to the body using a strap or a piece of textile that can maintain the device 2000 in contact with the body.

Figure 16:
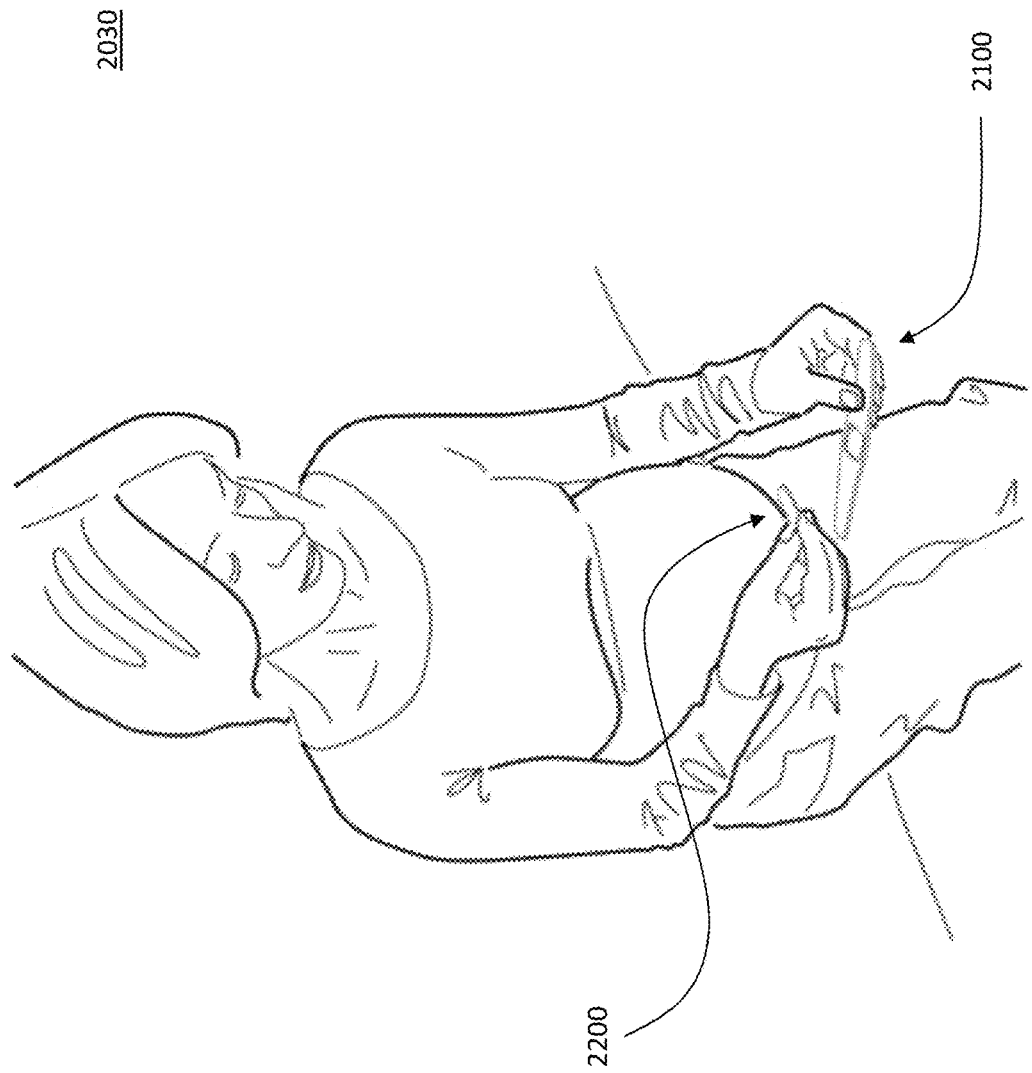
FIG. 16 shows an exemplary illustration of yet another embodiment of the device for contraction monitoring of FIG. 13.

FIG. 16 shows another exemplary embodiment of the contraction monitoring device 2000, wherein the electrode patch 2100 and the sensor module 2200 can be two separate parts of the device. The sensor module 2200 can be attached to the electrode patch 2100 before being used to monitor contractions. In some embodiments, the contraction monitoring device 2000 of FIG. 16 can have at least three electrodes, including one measurement electrode located on one extremity of the device 2000, one reference electrode located on the other extremity of the device 2000, and one bias electrode in the middle. Such a configuration enables the measurement of one channel EXG signal, along the horizontal direction. In some embodiments, the device 2000 of FIG. 16 can have 4 electrodes, two measurement electrodes located on the two extremities, one reference electrode located in the middle of the device 2000, and one bias electrode located between a measurement electrode and the reference electrode. The electrode patch 2100 can be reusable and washable. Alternatively, the electrode patch 2100 can be disposable, that is the user can change the electrode patch 2100 after each use of the contraction monitoring device 2000.

Figure 17:
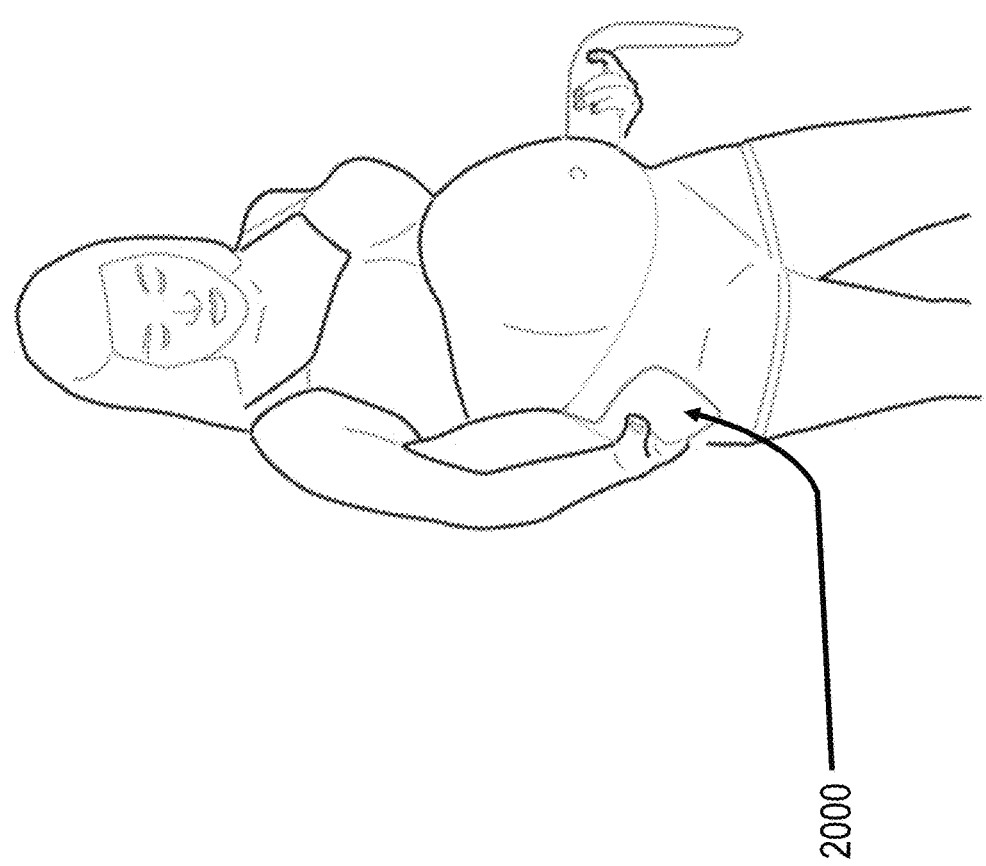
FIG. 17 shows an exemplary illustration of yet another embodiment of the device for contraction monitoring of FIG. 13.

FIG. 17 shows an exemplary embodiment of the contraction monitoring device 2000, wherein the electrode patch 2100 and the sensor module 2200 can be integrated in a textile or clothing accessory. Examples of clothing accessorys can include, but are not limited to: a shirt, T-shirt, belly-band, a pregnancy support belt, or a belt. In some embodiments, the contraction monitoring device 2000 of FIG. 16 can have at least three electrodes arranged next to each other so that one measurement electrode is located on the right (respectively left) side of the abdomen, one reference electrode is located on the left (respectively right) side of the abdomen, and one bias electrode in the middle. In some embodiments, the device of FIG. 15 can have a fourth electrode positioned at 90 degrees from the linear arrangement, in the center of the abdomen. This fourth electrode can provide a measurement of the EXG signals in the vertical direction. In some embodiments, the device 2000 of FIG. 15 can have a fifth electrode positioned at the back of the woman, and provide a signal free of uterine activity but carry physiological and recording artifacts that can be used in processing the EXG signals to obtain cleaner and more accurate EHG, mECG, and fECG signals.

Figure 18:
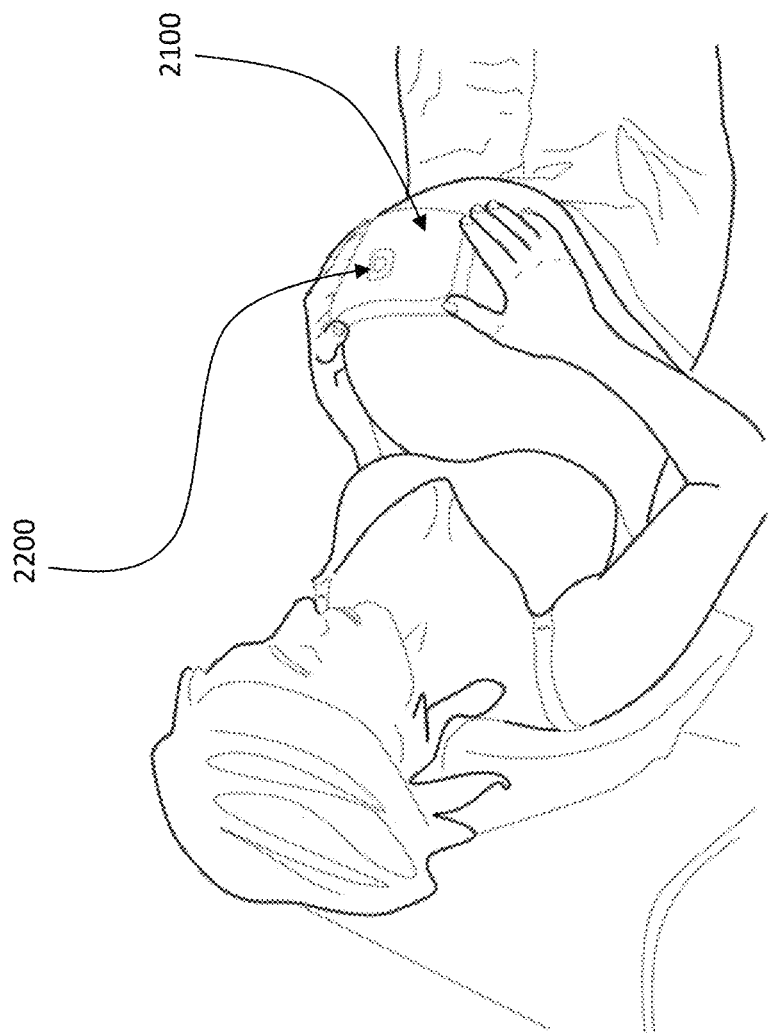
FIG. 18 shows an exemplary illustration of yet another embodiment of the device for contraction monitoring of FIG. 13.

FIG. 18 shows an exemplary embodiment of the contraction monitoring device 2000, wherein the electrode patch 2100 and the sensor module 2200 can be integrated into an accessory of every-day life that can be positioned on a woman's abdomen. For instance, the electrode patch 2100 and the sensor module 2200 can be integrated in a pillow or in a cover.

As it can be seen from FIGS. 13-18, the device 2000 for contraction monitoring is integrated in a small and easy to use form factor that does not require operation by clinical staff. Stated somewhat differently, the device 2000 for contraction monitoring is advantageously implemented in such a way that a pregnant woman can operate it on her own. The small size and extreme miniaturization can be achieved thanks to low-power electronics system design, that is a combination of low-power circuit design, low-power architecture design, and firmware optimization. Low-power system design allows minimizing the size of the battery and therefore can achieve very small size for the overall system. The ease of use can come from a combination of smart electronics and high level of integration. With smart electronics, the device 2000 can automatically turn on when it is positioned on the body, or the device 2000 can automatically detect contractions and trigger feedback accordingly, or the system can automatically detect a specific situation—for example the fact that the woman is moving—and adapt its signal processing accordingly. With high level of integration, the electrode patch 2100 can integrate all wires to the electrode, and provide a very simple way for the user to connect the sensor 2200 to the electrode patch. Connecting the electrode patch 2100 to the sensor 2200 can be done through magnetic interface, through a snap on mechanism, through a slide on mechanism, through a screw on mechanism, or any other mechanisms that provide a good mechanical and electrical contact between the sensor module 2200 and the electrode patch 2100.

The use of an electrode patch 2100 improves the reliability of contraction monitoring as it is not possible for a user to misplace the different electrodes relatively to each other, as they are always in the same relative position. The use of an electrode patch 2100 improves the experience and the ease of use of contraction monitoring as it does not require attaching multiple electrodes to the abdomen, but only requires a user to attach one single electrode patch.

The device 2000 can be designed such that it is clear for the pregnant woman how to wear the device, and where to place it. The device 2000 can be designed such that it is very easy to put on. Preferably, the pregnant woman simply has to take the sensor module 2200, attach it to the electrode patch 2100, and wear it.

The electrode patch 2100 comprises at least two electrodes, referred to as the measurement electrode and the reference electrode, and allows the measurement of one channel bio-potential (EXG) signal. In an alternative embodiment of the device, the electrode patch 2100 can include a third electrode, which can be used for biasing the signal acquisition electronics to the body voltage, or for applying a common mode voltage to the body in order to reduce the measurement noise, a measurement principle also known as right leg drive. In another alternative embodiment of the device 2000, the electrode patch 2100 can include additional measurement electrodes, allowing the measurement of multiple channels of EXG signals, leading to multiple channels of uterine contraction signals. The multiple measurement electrodes can be positioned on different locations on the abdomen, advantageously providing multi-dimensional measurement of the uterine electrical activity. The electrodes may or may not include conductive gel. Conductive gel may be used to improve the quality of the contact between the body and the electrodes. The electrode patch 2100 may or may not be adhesive.

In a preferred embodiment, and according to the method 100 for contraction monitoring of FIG. 1 and FIG. 2A, the electrode patch 2100 integrates three measurement electrodes, one reference electrode and one bias electrode. Turning to FIG. 2A, the reference electrode 3002 is positioned slightly under the navel 3001. The three measurement electrodes (3004, 3005, 3006) are positioned respectively to the right, to the left and below the reference electrode 3002. The distance between the reference electrode 3002 and each measurement electrode (3004, 3005, 3006) is between three to ten centimeters. The bias or right leg drive electrode 3003 can be positioned anywhere on the abdomen, but not too far from the other electrodes. Preferably and advantageously, all electrodes can be integrated into an electrode patch 2100. The electrode patch 2100 can significantly improve the reliability, the experience, and the use of the method for monitoring contractions of FIG. 1.

The sensor module 2200 can include the electronic circuitry required to measure EXG signals and extract uterine contraction signals according to the method 100 for uterine contraction monitoring of FIG. 1.

Figure 19:
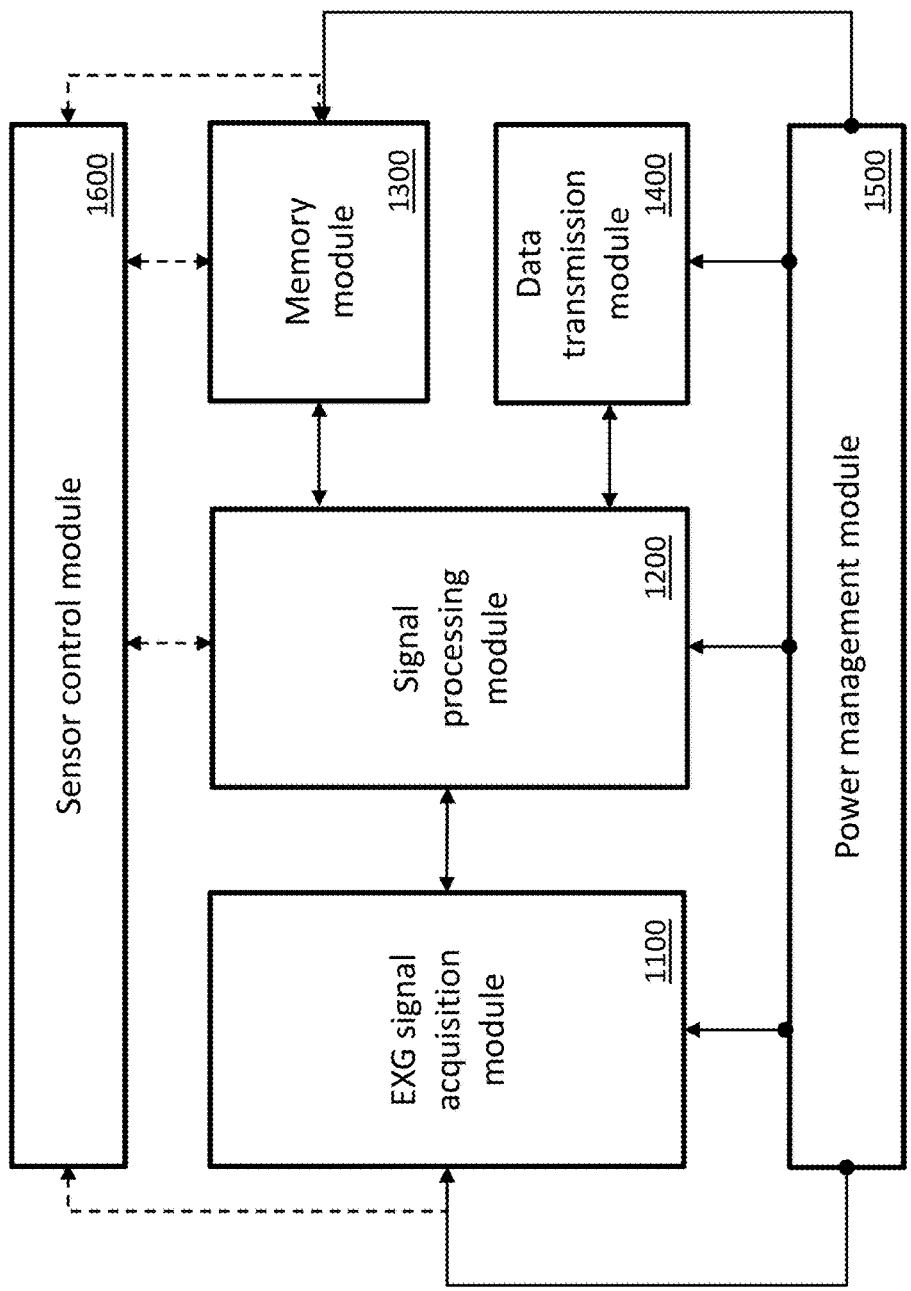
FIG. 19 is an exemplary an exemplary block-diagram of one embodiment of the sensor module of FIG. 13-18.

FIG. 19 shows an exemplary block diagram of one embodiment of the sensor module 2200 of FIGS. 13-18. Turning to FIG. 19, the sensor module 2200 includes: An EXG signal acquisition module 1100, a signal processing module 1200, at least one of a memory module 1300 or a data transmission module 1400, a power management module 1500, and a sensor control module 1600.

The EXG signal acquisition module 1100 acquires the at least one channel EXG signals measured with the electrode patch 2100. In another embodiment (not shown) of the sensor module 2200 of FIG. 19, the EXG signal acquisition module 1100 may further include: a conditioning module, an amplification module, an analog filter module, and an analog-to-digital conversion module. Preferably, the conditioning module conditions the EXG signals before amplification. For instance, the conditioning system comprises removing the DC component from the EXG signals or filtering the EXG signals. In another, more advanced example, the conditioning module includes an analog artifact filter that filters out artifacts such as motion artifacts. Advantageously, the amplification module amplifies the EXG signals to a level that is compatible with the remaining of the sensor module electronics. More advantageously, the analog filter module further filters the amplified EXG signals, for instance to avoid aliasing during the analog-to-digital conversion. The analog-to-digital conversion module can convert the analog EXG signals to digital EXG signals. In another alternative embodiment, the EXG signal acquisition module 1100 can further include a digital motion artifact filter. The digital motion artifact filter system can further filter the digital EXG signals to specifically remove artifacts and improve the quality of the EXG signals.

More preferably, the signal processing module 1200 can process the EXG signals to extract the UC signals according to the method 100 for contraction monitoring of FIG. 1. In an alternative embodiment, the signal processing module

1200 is configured to process the EXG signals to extract the UC signals, at 120, and compute the UC statistics, at 140, according to the method 100 for contraction monitoring of FIG. 2. In another alternative embodiment, the signal processing module 1200 can process the EXG signals to extract the UC signals, and at least one of the UEMG signals, the mECG signals, the mHR, the mHRV, the fECG signals, the fHR or the fHRV. In another alternative embodiment, the signal processing module 1200 can include dedicated processing blocks to remove artifacts from the EXG signals after the EXG signals are acquired by the EXG signal acquisition module and before any further processing. The signal processing module 1200 can be implemented in a digital signal processor (DSP), in a micro-controller unit (MCU), in a field programmable gate array (FPGA), in an application specific integrated circuit (ASIC), in application specific processor (ASP), etc.

Preferably, the memory module 1300 stores the data corresponding to at least one of the signals generated by the signal processing module 1200. The data can be stored on a volatile or non-volatile support. For example, the data can be stored on FLASH memory.

Advantageously, the data transmission module 1400 transmits at least one of the signals generated by the signal processing module 1200 to a user personal device. The user personal device can be a smartphone, a tablet, a smart-watch, smart-glasses, a personal computer, and/or any multimedia device that is equipped with wired, wireless, or optical communication. Wired communication can be achieved using USB, Ethernet, HDMI, FireWire, Thunderbolt, RS232 or any other wired communication protocol. Wireless communication can be achieved using Bluetooth, Bluetooth low-energy, WiFi, Zigbee, NFC or any other wireless communication protocol.

The power management module 1500 can deliver power to the different modules of the contraction monitoring device 2000. In an alternative embodiment, the power management module 1500 can include power management circuitry, a battery and on/off circuitry. The power management circuitry can convert the battery voltage to the right level of input voltage for the different modules of the device. The power management module 1500 can deliver an input voltage that is specific and may be different for every module. The battery can be rechargeable or alkaline and can be of different chemistry and shape. In the case of a rechargeable battery, the power management circuitry can also include charging circuitry. The on/off circuitry can be a switch that allows the user to switch the device on and off. In another alternative embodiment, the on/off circuitry can advantageously include electronic circuitry to detect when the electrode patch 2100 is connected to the sensor module 2200. The device 2000 can then automatically start upon detection of a connection between the sensor module 2200 and the electrode patch 2100, and/or stop when the sensor module 2200 is detached from the electrode patch 2100, thus greatly improving the user experience. In yet another alternative embodiment, the on/off circuitry can advantageously include electronic circuitry to detect when the contraction monitoring device 2000 is attached to the body. The device 2000 can then automatically start upon attachment of the contraction monitoring device 2000 on the body, and/or stop upon removal of the contraction monitoring device 2000 from the body, thus greatly improving the user experience.

The sensor control module 1600 controls the operation of the sensor module 2200 and ensures that the EXG signal acquisition module 1100, the signal processing module 1200, the memory module 1300, and the data transmission module 1400 can work together in an efficient implementation of the sensor module 2200. Preferably, the sensor control module 1600 can be implemented in a micro-controller unit.

Figure 20:
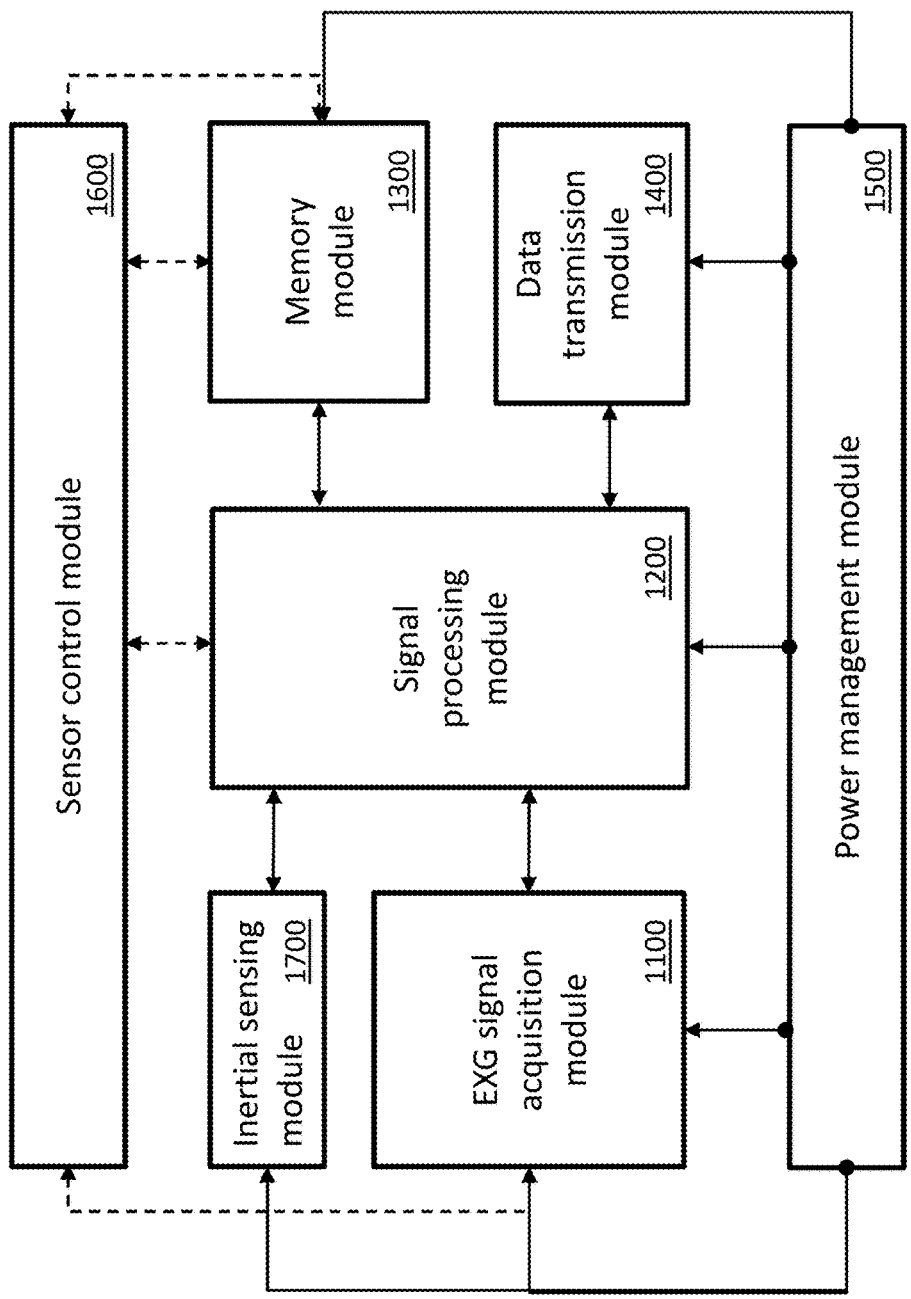
FIG. 20 is an exemplary an exemplary block-diagram of an alternative embodiment of the sensor module of FIG. 13-18.

FIG. 20 shows an alternative embodiment of the sensor module 2200 of FIG. 19, wherein the sensor module 2200 can further include an inertial motion sensing module 1700. The inertial motion sensing module 1700 can include at least a one-axis accelerometer, a two-axis accelerometer, or a tri-axis accelerometer. The inertial motion sensing module 1700 can also include a one, two, or tri-axis gyroscope, and/or a one, two, or tri-axis magnetometer. The inertial motion sensing module 1700 can be used to monitor the overall movement of the pregnant woman or the movements of the abdomen induced by fetus movement and kicks.

Alternatively or additionally, the inertial motion sensing module 1700 can be used to measure the local movement of the sensor module. In a further embodiment, the data coming from the inertial motion sensing module 1700 can be used by the signal processing module 1200 to filter artifacts from the EXG signals.

Figure 21:
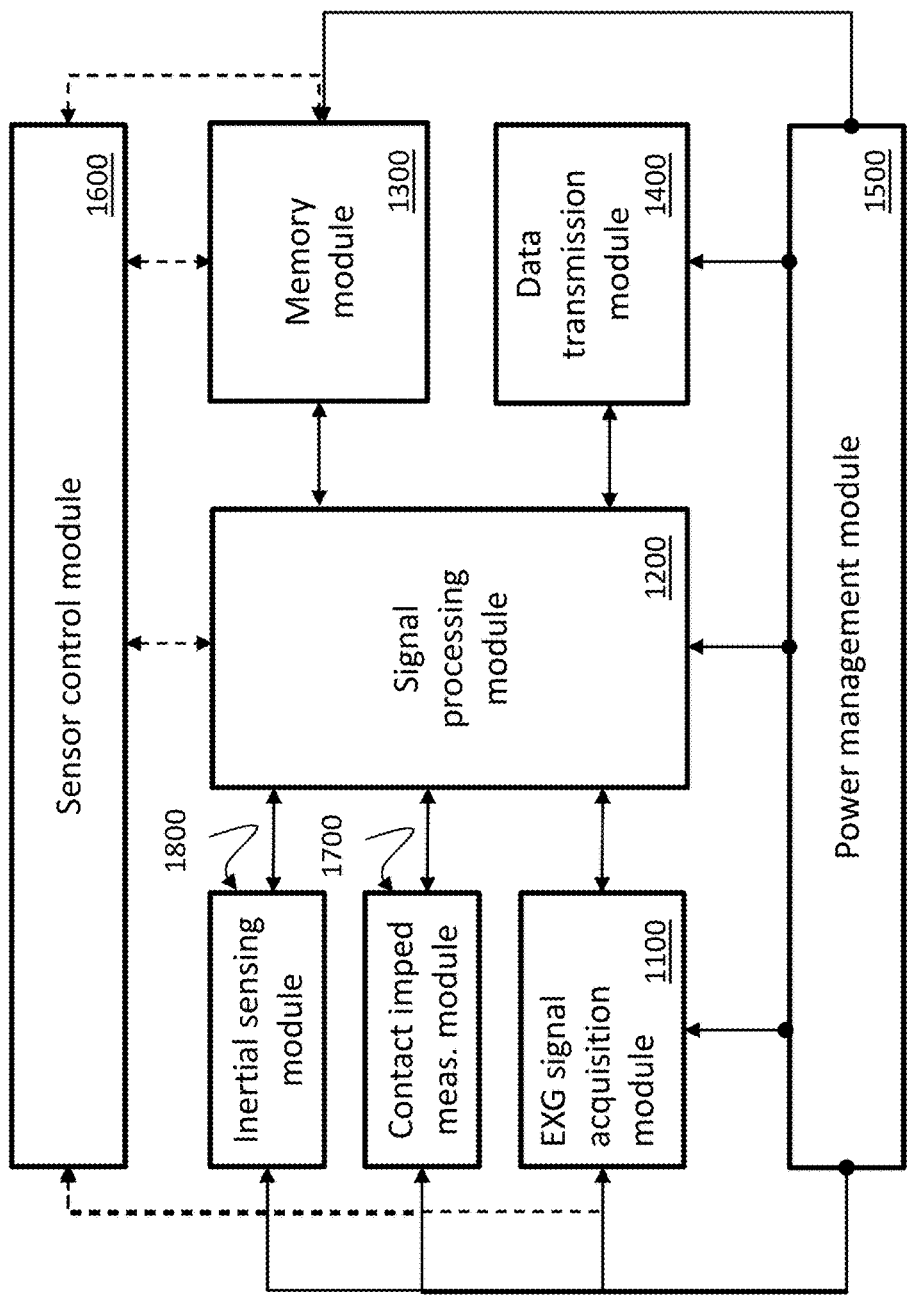
FIG. 21 is an exemplary an exemplary block-diagram of another alternative embodiment of the sensor module of FIG. 13-18.

FIG. 21 shows an alternative embodiment of the sensor module 2200 of FIG. 19 or FIG. 20, wherein the sensor module 2200 can further include a contact-impedance measurement module 1800. The contact-impedance measurement module 1800 can be used to continuously or intermittently measure the impedance of the contact of each electrode with the body. Accordingly and advantageously, the contact impedance can be used to provide an estimation of the quality of the contact, or to provide an estimation of motion artifacts. In a further embodiment, the contact impedance signals can be used by the signal processing module 1200 to filter artifacts from the EXG signals.

Figure 22:
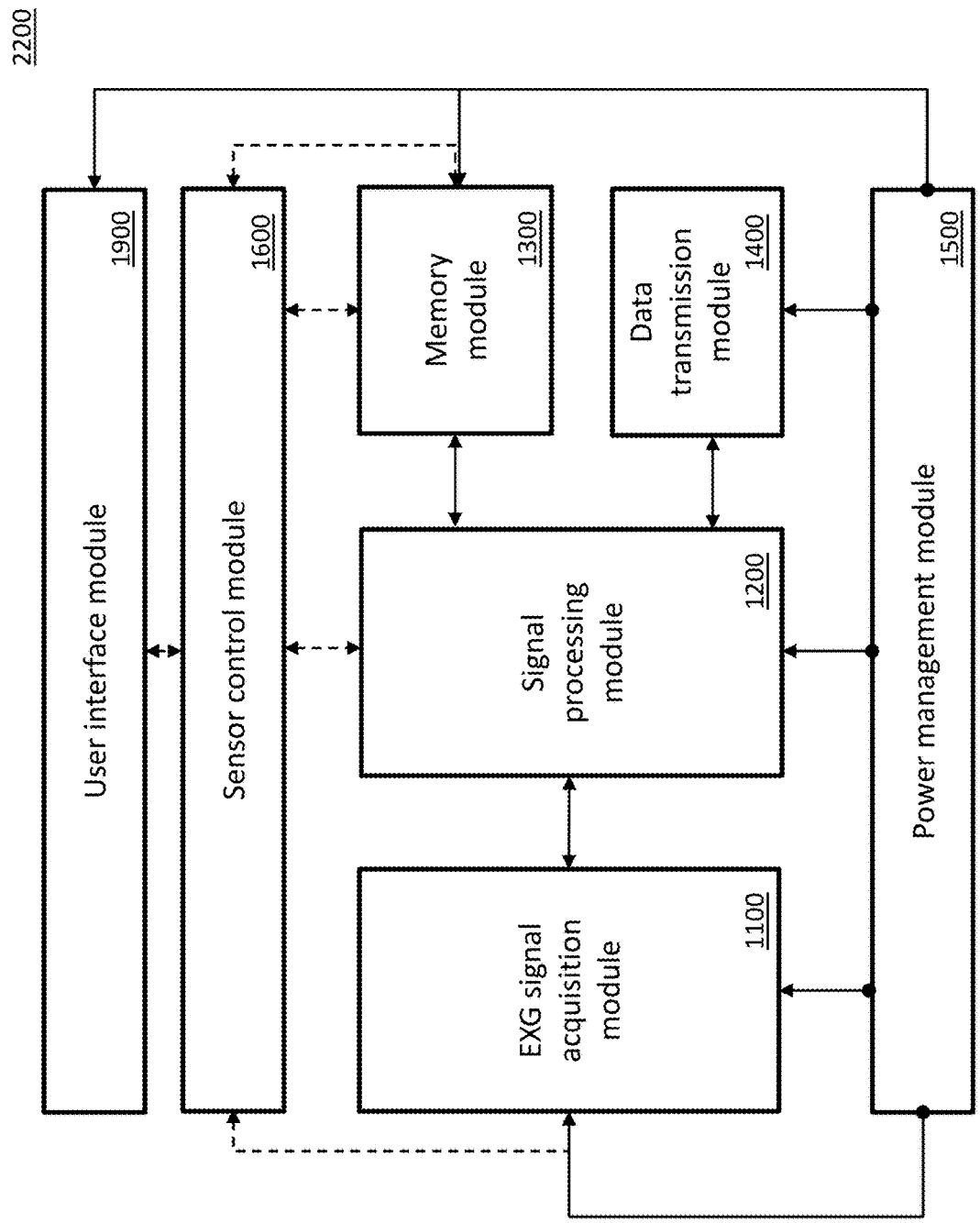
FIG. 22 is an exemplary an exemplary block-diagram of yet another alternative embodiment of the sensor module of FIG. 13-18.

FIG. 22 shows an alternative embodiment of the sensor module 2200 of FIG. 19, FIG. 20 or FIG. 21, wherein the sensor module 2200 can further include a user interface module 1900. The user interface module 1900 can be one or any combination of: a Light Emitting Diode (LED), a set of LEDs, a buzzer, a vibrating element, an audio speaker, or a display. In the case of a set of LEDs, the individual LED can be arranged in a shape that represents a specific shape such as a circle, a rectangle, a triangle, or any other geometric shape. The LED color and/or activation pattern can be designed in order to communicate different messages to the user. For example, the LED can be used to communicate start of the system, stop of the system, battery charge level, the detection of a contraction, the intensity of the contraction, the frequency of contraction, the duration between two contractions, etc. The LED can be controlled by the sensor control module 1600.

Figure 23:
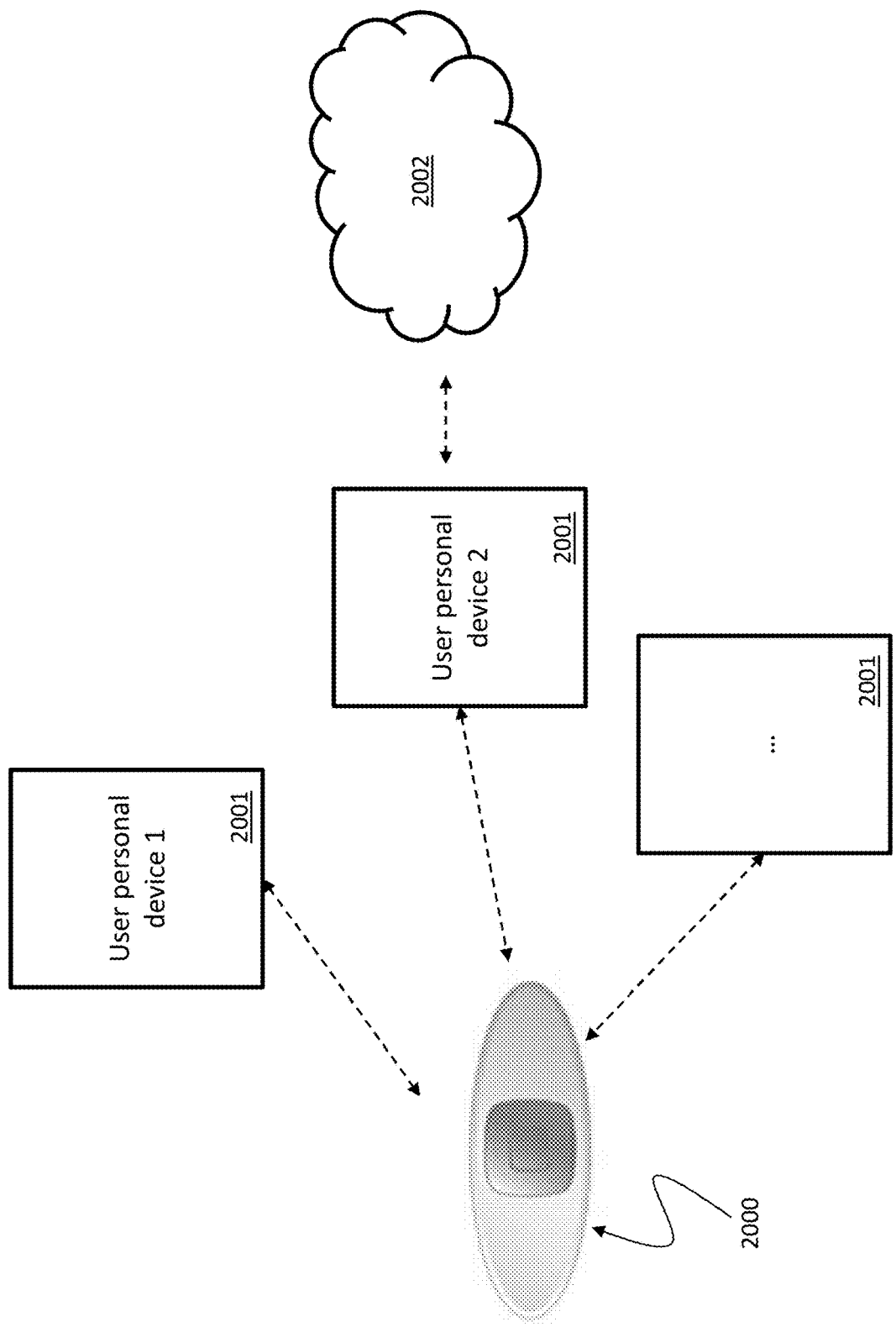
FIG. 23 shows an exemplary illustration of yet another embodiment of the device for contraction monitoring of FIG. 14, wherein the contraction monitoring device is communicating with user personal devices.

FIG. 23 shows an alternative embodiment of the contraction monitoring device 2000 of FIGS. 13-18, wherein the contraction monitoring device 2000 is used in combination with at least one user personal device 2001. The user personal device 2001 can be a smartphone, a tablet, a smart-watch, smart-glasses, a personal computer and/or any multimedia or digital device. In a further embodiment, the data monitored and transmitted by the contraction monitoring device 2000 to the user personal device 2001 can be displayed and/or stored on the user personal device 2001. In yet a further embodiment, the data monitored and transmitted by the contraction monitoring device 2000 can be further transmitted, via the user personal device 2001, to a cloud-based server, or database 2002.

In another alternative embodiment of the contraction monitoring device 2000 of FIGS. 13-18, the data from the contraction monitoring device 2000 can be combined with the data measured from a health or wellness monitoring device. For example, the data from the contraction monitoring device 2000 can be combined with data from a weight scale, an activity tracker, a heart rate chest-strap, a wrist-based pulse-rate monitor, a basal temperature sensor, or from any other ambulatory, wearable or portable monitoring system.

In yet another alternative embodiment, the contraction monitoring device 2000 of FIGS. 13-18 can be used to monitor at least one UC signal and/or UC statistics, and visualize the at least one UC signal and/or UC statistics on the display of the user personal device 2001. To achieve this task, the EXG signal acquisition module 1100 can acquire at least one EXG signal, and the signal processing module 1200 can process and analyze the EXG signals according to the method 100 of any of FIGS. 1-4. For example, turning to FIG. 1, the EXG signals can be processed to extract EHG signals, at 120, the EHG signals can be further processed to extract UC signals, at 130, and UC signals can be analyzed to compute relevant UC statistics, at 140 The data transmission module 1400 can then transmit the at least one UC signal to the user personal device 2001 for visualization.

In yet another alternative embodiment, the contraction monitoring device 2000 of FIGS. 13-18 can be used to classify contractions, wherein the signal processing module 1200 of FIG. 15 can process and analyze the EXG signals according to the method 100 of FIG. 5A or FIG. 5B. Turning to FIG. 5A or FIG. 5B, the EXG signals can be processed to extract UEMG signals, at 210, the UEMG signals can be further processed to extract UEMG markers, at 220, and the UEMG markers can be used to classify contraction types, at 230. In a further embodiment, the information about the contraction classification can be displayed to the user through the user interface module 1900 or on her user personal device 2001. In a further embodiment, the contraction monitoring device 2000 of FIGS. 13-18 can be used to distinguish between Braxton Hicks and true labor contractions.

In yet another alternative embodiment, the contraction monitoring device 2000 of FIGS. 13-18 can be used to detect labor, wherein the signal processing module 1200 of FIG. 15 can further analyze the UC signals and/or the contraction type to detect labor, at 240, according to the method 100 of FIG. 6. Additional labor detection embodiments are described elsewhere herein.

In yet another alternative embodiment, the contraction monitoring device 2000 of FIGS. 13-18 can be used to monitor maternal stress level, wherein the signal processing module 1200 of FIG. 15 can process and analyze the EXG signals according to the method 100 of FIG. 8. Turning to FIG. 8, the EXG signals can be processed to extract mECG signals, at 310, the mECG signals can be further processed to extract mHR and mHRV, at 320, and mHR and mHRV can be further processed to extract maternal stress level, at 330. In a further embodiment, the UC signals and/or UC statistics can be correlated with the maternal stress, at 340, and according to the method 100 for contraction monitoring of FIG. 8. The correlation between contractions and stress level can be visualized in one graph that overlays the UC statistics and the stress level over time. For example, the number of contractions per hour can be visualized together with the average stress level per hour. In another embodiment, the correlation between contractions and stress level can be summarized in a correlation score that summarizes in one number to what extent stress correlates with contractions for a certain user of the system. Thus, the contraction monitoring device 2000 of FIGS. 13-18 can advantageously be used to correlate UC signals and/or statistics with maternal stress level, providing new insights on the relationship that may exist between maternal stress and contractions.

In yet another alternative embodiment, the contraction monitoring device 2000 of FIGS. 13-18 can be used to monitor UC signals and at least one of fECG, fHR, or fHRV, wherein the signal processing module 1200 of FIG. 15 can process and analyze the EXG signals according to the method of FIG. 9A or FIG. 9B. Turning to FIG. 9A or FIG. 9B, the EXG signals can be processed to extract fECG signals, at 410, and the fECG signals can be further processed to extract fHR and fHRV, at 420. In a further embodiment, the contraction monitoring device 2000 of FIG. 13 can be used to monitor the position of the fetus, according to the method 100 of FIG. 9C. In a further embodiment, the contraction monitoring device of FIGS. 13-18 can be used to monitor the movement of the fetus, according to the method 100 of FIG. 9D.

In yet another alternative embodiment, the contraction monitoring device 2000 of FIGS. 13-18 can be used to jointly visualize the UC signals and the fHR. The signal processing module 1200 can simultaneously extract the UC signals and the fHR, and can correlate UC signals with fHR according to the method 100 of FIG. 10. The fHR and the UC signals can be transmitted to the user personal device 2001 where they can be displayed on top of each other, similar to the way signals are displayed on a cardiotocogram in hospital environments. Stated somehow differently, the contraction monitoring device 2000 of FIG. 18 advantageously provides similar information to a cardiotocogram with greatly improved user experience since the contraction monitoring device can be made much smaller and much more comfortable to use than traditional strapped cardiotocogram probes.

In yet another alternative embodiment, the contraction monitoring device 2000 of FIGS. 13-18 can be used to monitor maternal activity, according to the method 100 for monitoring uterine contractions of FIG. 11. In one embodiment, the maternal activity can be measured with the inertial sensing module 1800 of FIG. 21. In another embodiment, the maternal activity can be measured using an activity sensor integrated in the user personal device 2001, e.g. a smartphone. In yet another embodiment, the maternal activity can be measured using a separate activity tracker that can connect to the user personal device 2001.

In yet another embodiment, the UC signals and/or UC statistics can be correlated with the maternal activity, using correlating contractions with maternal activity, at 520, according to the method 100 for contraction monitoring of FIG. 11. The correlation between contractions and maternal activity can be visualized in one graph that overlays the UC statistics and the maternal activity over time. For example, the number of contractions per hour can be visualized together with the cumulated and/or average activity per hour. In another embodiment, the correlation between contractions and maternal activity can be summarized in a correlation score that summarizes in one number to what extent maternal activity correlates with contractions for a certain user of the system. Thus, the contraction monitoring device 2000 of FIGS. 13-18 can advantageously be used to correlate UC signals and/or statistics with maternal activity, providing new insight on the relationship that may exist between maternal activity and contractions.

In yet another alternative embodiment, the contraction monitoring device 2000 of FIGS. 13-18 can be used to monitor fetal activity, according to the method 100 for monitoring uterine contractions of FIG. 12. In one embodiment, the fetal activity can be extracted from the fECG, by processing fECG to extract movement of the fetus, at 430, according to the method 100 for monitoring contractions of FIG. 9D. In another embodiment, the fetal activity can be measured with the inertial sensing module 1800 of FIG. 21. In yet another embodiment, the UC signals and/or UC statistics can be correlated with the fetal activity, correlating contractions with fetal activity, at 620, according to the method 100 for contraction monitoring of FIG. 12. The correlation between contractions and fetal activity can be visualized in one graph that overlays the UC statistics and the fetal activity over time. For example, the number of contractions per hour can be visualized together with the cumulated and/or average fetal activity per hour. In another embodiment, the correlation between contractions and fetal activity can be summarized in a correlation score that summarizes in one number to what extent fetal activity correlates with contractions. Thus, the contraction monitoring device 2000 of FIGS. 13-18 can advantageously be used to correlate UC signals and/or statistics with fetal activity, providing new insight on the relationship that may exist between fetal activity and contractions.

In yet another alternative embodiment, the contraction monitoring device 2000 of FIGS. 13-18 can provide feedback to the user, according to the method 100 for monitoring contractions of FIGS. 13-18. Feedback can include further information on the data recorded with the contraction monitoring device. Alternatively or additionally, feedback can include recommendations for adaptations in lifestyle or behavior based on the data measured by the contraction monitoring device. Feedback can be provided through the user interface module 1900 of FIG. 22, through the user personal device 2001 of FIG. 19, and/or through any other communication tools to the user. Feedback can take the form of a noise, a certain LED pattern, a text message, a voice message, or any other multimedia communication.

Various methods described elsewhere herein may be used to ultimately identify a labor state of a pregnant female. One non-limiting embodiment of a computer-implemented method 2400 for identifying a labor state in a pregnant female is provided in FIG. 24. Such a method may be performed by any suitable device or system, such as, for example, any of the devices or systems described above.

Figure 27:
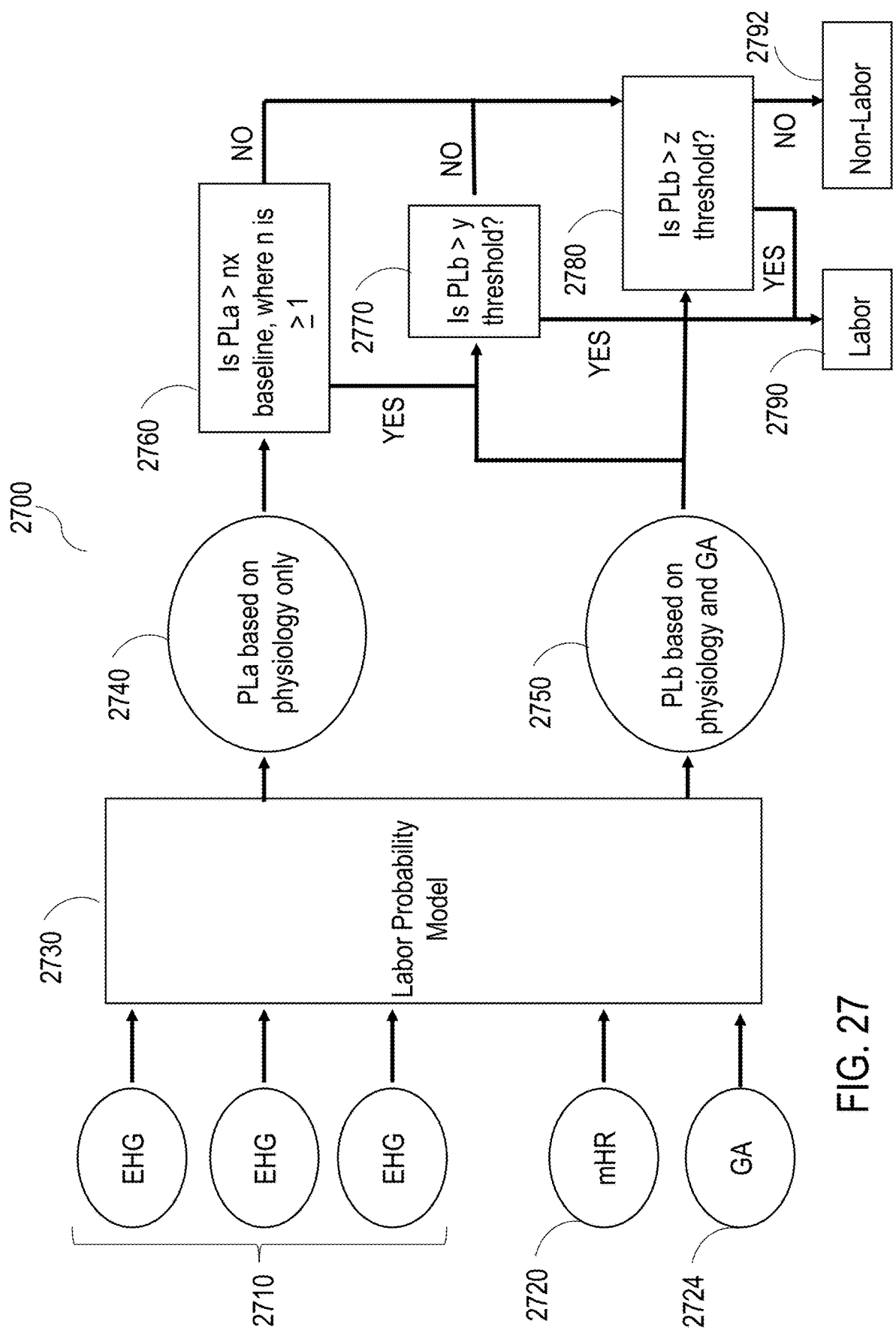
FIG. 27 is an exemplary flow diagram illustrating another embodiment of a method of identifying a labor state in a pregnant female.

As shown at block S2410, the depicted method includes acquiring a physiological signal from a physiological sensor. The physiological signal may be one or more biopotential signals, for example, EHG, maternal ECG, and/or fetal ECG signals. In some embodiments, the physiological signal is acquired using a plurality of physiological sensors. In some embodiments, a plurality of physiological signals is acquired. For example, acquiring a physiological signal may include acquiring an EHG signal and, additionally or alternatively, one or more signals indicative of maternal uterine activity, maternal uterine muscle contractions, maternal heart electrical activity, maternal heart rate, fetal movement, fetal heart rate, maternal activity, maternal stress, contraction force, contraction frequency, and/or fetal stress, as described elsewhere herein. In various embodiments, the one or more physiological signals are sensed by a sensor having a plurality of electrodes and recorded by a processor into memory. As shown in FIG. 27, the physiological signal sensed by one or more physiological sensors comprises an EHG 2710 and maternal heart rate 2720. The physiological signals may be sensed over time to determine a labor state.

At block S2420, the method includes processing the physiological signal to identify and extract a parameter of interest from the signal. The physiological signal may first undergo digital signal processing or signal processing via one or more signal processing components. The signal may be amplified, filtered, digitized, and/or otherwise processed to isolate a readable physiological signal from a noisy acquired signal. The physiological signal may undergo further processing by a computer processor to identify and extract a particular parameter of interest from the signal. The parameter of interest may be, for example, one or more of: a maternal heart rate metric, a maternal heart rate variability metric, a fetal heart rate metric, a fetal heart rate variability metric, a range of an electrohysterography signal, a power of an electrohysterography signal in a specific frequency band, a frequency feature of an electrohysterography signal, a time-frequency feature of an electrohysterography signal, a frequency of contractions, a duration of contractions, a force of contractions, and an amplitude of contractions. In some embodiments, the metric (e.g., the maternal heart rate metric or fetal heart rate variability metric) is a mean value, a median value, a standard deviation, or any other meaningful statistic calculated from the signal as descried elsewhere herein. The parameter of interest may be a physiological parameter and/or a behavioral parameter. For examples, in some embodiments, the parameter of interest may be a measure of maternal anxiety or stress, as described elsewhere herein. In some embodiments, the parameter of interest may be an action, observed behavior, or feeling that is entered into the system by the pregnant woman or other user.

The parameter of interest may be automatically selected using a machine-learning based feature selection process, such as random forest or other feature selection techniques. The parameter or parameters of interest selected may change over time or vary from user to user, based on those parameters that are most indicative of a labor state for a specific population or for a specific user. These parameters of interest represent physiological characteristics or markers that are discriminative of a labor state.

At block S2430, the method includes analyzing the parameter of interest to determine whether the parameter is indicative of a labor state. As shown in FIG. 27, the physiological signals (e.g., EHG and mHR) 2710, 2720 sensed at block S2410 along with a gestational age (GA) 2724 of the pregnancy are fed into a labor probability model 2730, which uses, for example, a generalized linear regression model. The labor probability model 2730 outputs a first labor probability, PLa, 2740 based only on the sensed physiological signals 2710 and a second labor probability, PLb, 2750 based on the sensed physiological signals 2720 and the gestational age 2724 of the pregnancy (e.g., calculated based on a first day of a last menstrual cycle or based on ultrasound). The first threshold (y) is the value of PLb above which the method indicates a labor condition, as long as the condition of PLa is true. The second threshold (z) is the value of PLb above which the method will always indicate a labor condition, regardless of the PLa value.

PLb is used in blocks 2770 and 2780 to determine whether PLb is greater than a first or y threshold and a second or z threshold, respectively. For example, the first or y threshold equals 0 to 1, 0.01 to 0.15, 0.02 to 0.14, 0.03 to 0.13, 0.04 to 0.12, 0.05 to 0.11, 0.06 to 0.1, 0.07 to 0.09, 0.08 to 0.12, substantially 0.08, substantially 0.09, substantially 0.1, substantially 0.11, at least 0.09, at least 0.1, etc. The second or z threshold equals 0 to 1, 0 to 0.5, 0.25 to 0.5, substantially 0.25, substantially 0.3, at least 0.25, at last 0.3, etc.

The processor determines whether PLa is nx greater than a personalized baseline 2760. For example, the personalized baseline is computed for each specific individual based on one or more previous parameter recordings or detected parameter signals or extracted parameters of interest. The personalized baseline may be computed as the standard deviation over one or more past recordings (e.g., past 7 recordings, one week, one month, all recordings to date, etc.). In any of the embodiments described herein, n equals an integer, for example 1, 2, 3, 4, 5, or 6. Alternatively, n equals a fraction, for example 1.25, 1.5, 1.75, 2.25, 2.5, 2.75, 3.25, 3.5, 3.75, etc. In one embodiment, n equals 3. If PLa is not nx greater than the baseline at 2760, then the method proceeds to block 2780, which determines whether PLb is greater than a second threshold. If PLb is not greater than the second or z threshold, then the method indicates a non-labor condition 2792. If PLb is greater than the second or z threshold, then the method indicates a labor condition 2790.

Alternatively, if PLa is nx greater than the baseline at 2760, then the method proceeds to block 2770, which determines whether PLb is greater than a first threshold. If PLb is not greater than the first or y threshold, then the method 2700 proceeds to block 2780. If PLb is greater than the first or y threshold, then the method 2700 indicates a labor condition 2790.

Analyzing the parameter of interest is performed by a computer processor. In some embodiments, analyzing the parameter of interest includes comparing the parameter to community data stored in a database. In such embodiments, the systems and methods described herein may acquire signals and extract parameters of interest from a plurality of system users. For example, the systems and methods may be used by hundreds, thousands, hundreds of thousands, or millions of users, and the acquired physiological signals and/or extracted parameters of interest may be stored in a database. Such a database of measured parameters may be used over time to determine which parameters are most indicative of a labor state. For example, for each user, the database may include physiological data throughout pregnancy, expected due date, actual baby's birth date, and notes associated with the data (e.g., times/dates when the user was in labor or times/dates when the user was experiencing false labor or Braxton Hicks contractions). The system or an administrator of the system may be able to identify or develop one or more trends, rules, correlations, and observations related to labor by tracking, aggregating, and analyzing the parameters from a plurality of users. For example, the data of a new user (i.e., a current user) may be compared with the data of all past users, to decide whether the new user is in a labor state or non-labor state. In one embodiment, the data from the new user may be compared to the data from past users using, for example a two-class classification engine based on the data from all past users. In such embodiments, a classification engine may take the parameter(s) of interest as input, and assign a class to the parameter(s) of interest, for example a labor or non labor classification (i.e., a binary classifier). Alternatively, in some embodiments, the classification engine may assign a probability of belonging to a labor class to each of the parameter(s) of interest, and a probability of belonging to the non-labor class (i.e., Prob(non-labor)=1−Prob(labor)). Based on this probability, the system may provide a likelihood of being in labor to the new user.

As used herein, community data may refer to the plurality of stored physiological signals or extracted parameters and/or the trends, rules, correlations, observations, or other data derived from the signals and parameters.

Additionally or alternatively, in some embodiments, analyzing the parameter of interest includes feeding the parameter into a machine learning model or algorithm trained to detect labor. The machine learning model or algorithm may be trained to detect labor based on past physiological data and recorded experiences provided by past users of the system. The machine learning model may mine through vast quantities of data to identify common trends, rules, or correlations. The machine learning model may compare recorded data to observed outcomes to identify patterns that can be used to predict or identify labor. The machine learning model of some embodiments includes one or more of a generalized linear model, a decision tree, a support vector machine, a k-nearest neighbor, a neural network, a deep neural network, a random forest, and a hierarchical model. In other embodiments, any other suitable machine learning model may be used.

Figure 25:
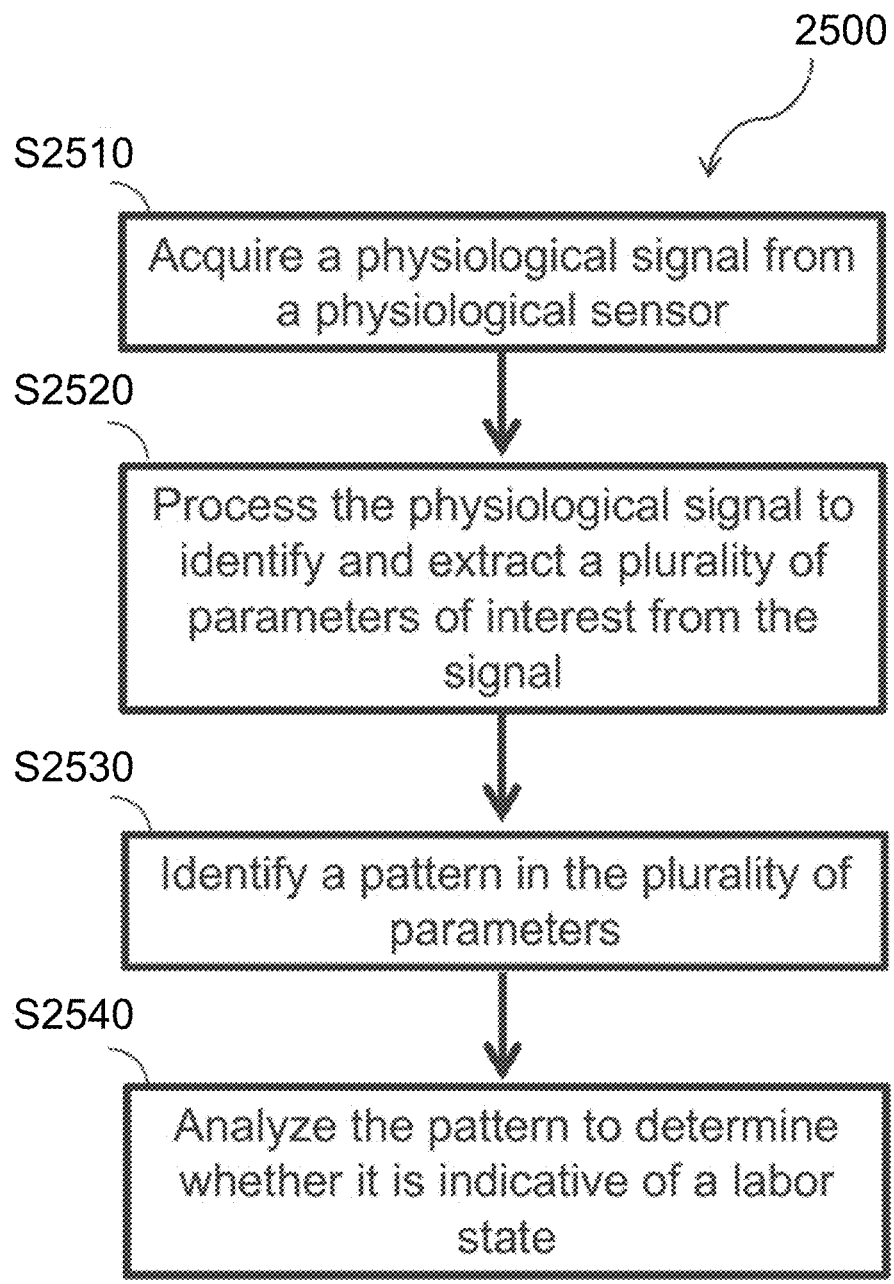
FIG. 25 is an exemplary flow diagram illustrating another embodiment of a method for identifying a labor state in a pregnant female.

An additional embodiment of a computer-implemented method 2500 for identifying a labor state in a pregnant female is provided in FIG. 25. As with the method 2400 above, the method 2500 of FIG. 25 includes: acquiring a physiological signal from a physiological sensor S2510, and processing the physiological signal to identify and extract a parameter of interest from the signal S2520. In the presently depicted method, a plurality of parameters is extracted. A plurality of parameters may be extracted from one physiological signal or one parameter each may be extracted from a plurality of physiological signals.

The method performed by a processor further includes identifying a pattern in the plurality of parameters S2530 and analyzing the pattern to determine whether the pattern is indicative of a labor state S2540. For example, a machine learning model may be trained with a reference dataset of known labor inducing patterns. The patterns determined to have the highest predictive power for labor detection may then be used to identify patterns based on sensed physiological signals and/or other data. In some embodiments, block S2540 is performed using simple decision trees, conditional logic, pattern recognition, or machine learning. Further, similar to the method 2400 described above, in the present embodiment, patterns may be identified and characterized using community data stored in a database and/or machine learning models. Some non-limiting examples of patterns include: regular contractions, contractions increasing in intensity and frequency over time, periodic changes in maternal heart rate associated with contractions, periodic changes in belly shape or deformation (e.g., measured using an accelerometer), or decreased heart rate variability over time due to increased load on the autonomic nervous system of the user.

Figure 26:
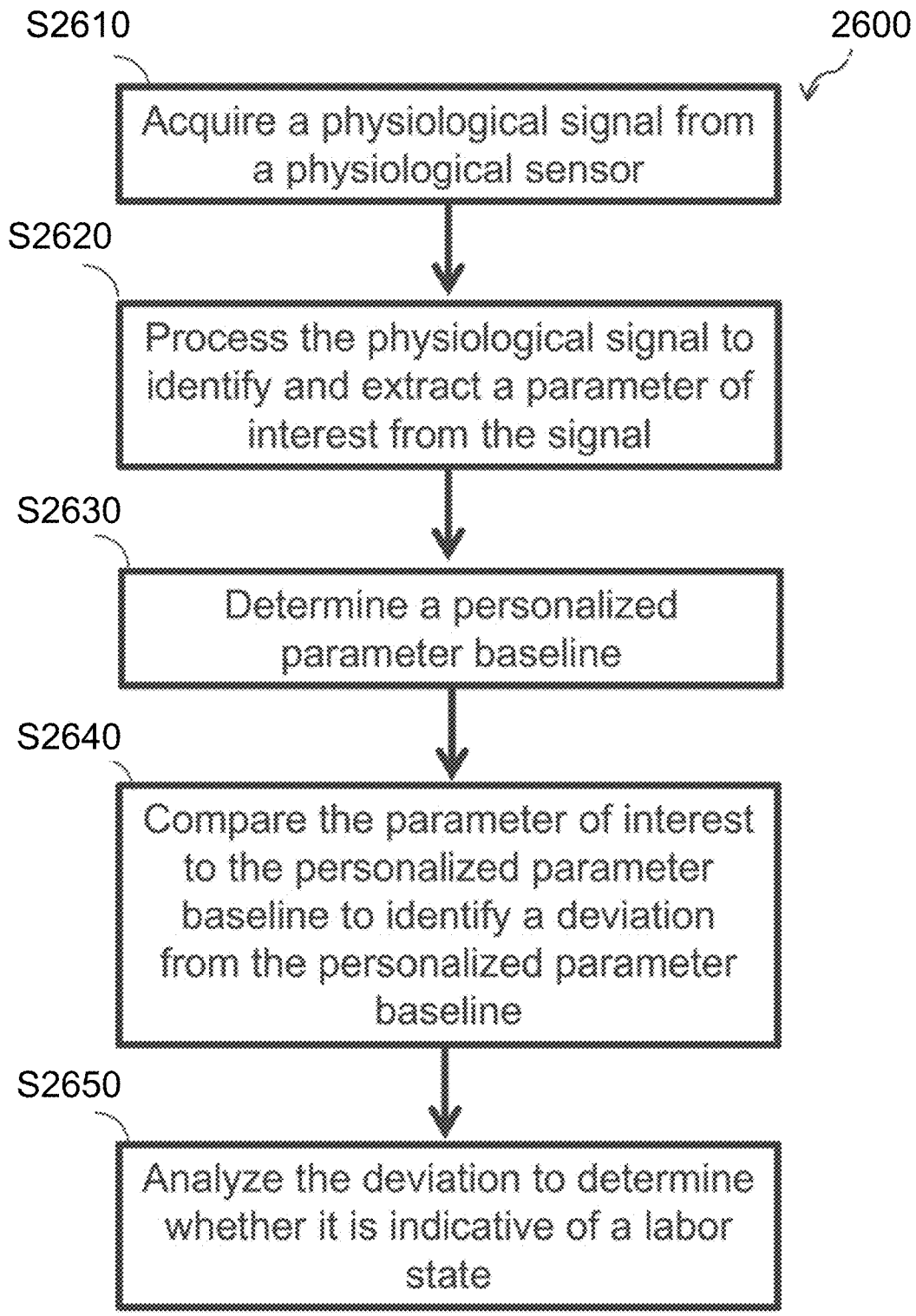
FIG. 26 is an exemplary flow diagram illustrating another embodiment of a method for identifying a labor state in a pregnant female.

Another embodiment of a computer-implemented method 2600 for identifying a labor state in a pregnant female is provided in FIG. 26. As with the above described methods, the method 2600 of FIG. 26 includes: acquiring a physiological signal from a physiological sensor S2610, and processing the physiological signal to identify and extract a parameter of interest from the signal S2620. In the method 2600 of FIG. 26, the processor additionally determines a personalized baseline for the pregnant woman at block S2630, compares the parameter of interest to the personalized baseline to identify a deviation from the personalized baseline at block S2640, and analyzes the deviation to determine whether the deviation is indicative of a labor state at block S2650.

At block S2630, the personalized baseline may be determined by tracking a parameter of interest over time and calculating a median value, a standard deviation, an observed range of values, or other meaningful metric for that parameter. For example, in some embodiments, a personalized baseline may be calculated by taking a reference measurement during a calibration phase. In such embodiments, a calibration phase may occur, for example, the first time a user uses the device, at a pre-determined or stochastic interval (e.g., weekly), or before every recording. Alternatively, in some embodiments, a personalized baseline may be calculated by measuring one or more parameters of interest during specific and/or controlled conditions, for example, during sleep, during relaxation, during meditation, or during an activity in which the parameter of interest is stable, is relatively constant, or has a predictable pattern.

In some embodiments, determining a personalized baseline includes computing or determining a personalized baseline by determining a value of the parameter over a given period of time. In one exemplary, non-limiting embodiment, determining a value of the parameter over time includes computing a standard deviation of the parameter over one or more past recordings, as described elsewhere herein. In the instance of PLa, the determined value may be the standard deviation of PLa over one or more past or previous recordings of one or more parameters. For example, the period of time may comprise 5-7 days of initial measurement or sensing using the devices described herein; 5-7 days of late pregnancy measurement, for example 5-7 days before an expected due date; and/or continuous measurement over time, for example for 10-20 weeks, 10-15 weeks, 5-10 weeks, 1-5 weeks, 2 to 6 weeks, etc.

At blocks S2640 and S2650, upon comparison of the parameter of interest to the personalized baseline, the processor determines whether the deviation is indicative of a labor state. In an exemplary case, the deviation is indicative of the labor state when the deviation is n times greater than the personalized baseline, where n equals, for example, 1, 2, or 3. The higher the value of n, the higher the specificity of the model (and the lower the sensitivity). As such, tuning n allows the model to be adjusted for specificity and sensitivity. In some embodiments, the method includes adjusting n to obtain more sensitive or more specific detection.

Similar to the method 2400 described above, in the present embodiment, deviations may be analyzed using community data stored in a database and/or machine learning models.

In some embodiments, a computer-implemented method for identifying a labor state in a pregnant female, such as any of the methods described above, also includes generating an alert related to the labor status. A command to generate the alert may be produced by the computer processor. The alert may be generated by a visual display, audio speakers, vibratory haptic feedback system, or other alert system located on the sensor module or mobile computing device. In some embodiments, the alert is a visual notification presented on a display screen providing an indication of labor status. In some embodiments, the alert is an auditory notification, such as an alarm, which sounds to provide an indication of labor status. In some embodiments, a vibration pattern may provide an indication of labor status.

The indication of labor status may include one or more of: a binary result (e.g., yes the woman is in labor or no the woman is not yet in labor), a probability that the woman is experiencing labor-inducing contractions, a degree of certainty around the determined probability, a probability that the pregnant female will enter the labor state within a given time period (e.g., within 12 hours, 24 hours, or 72 hours), and an estimate of time until the pregnant female enters the labor state. In some such embodiments, the method performed by the processor further includes calculating the relevant statistics, such as the probability that the woman is experiencing labor-inducing contractions, the degree of certainty around the determined probability, the probability that the pregnant female will enter the labor state within a given time period, and the estimate of time until the pregnant female enters the labor state.

In some embodiments, the computer-implemented method further includes sharing an alert related to the labor status with a contact. The alert may be sent automatically to one or more pre-selected contacts or pushed on demand when commanded by the pregnant user. For example, the alert may be shared with a gynecologist, obstetrician, other physician, nurse practitioner, veterinarian, other healthcare provider, doula, midwife, other birthing specialist, spouse, partner, parent, sibling, other family member, friend, a healthcare facility administrator, a service provider, or any other individual with whom the pregnant woman wishes to share such information. In some embodiments, upon detecting a positive labor status, the woman's healthcare provider and preferred healthcare facility are notified so that they may begin preparing for the woman's arrival. Alerts may be sent to contacts, for example, via an in-application notification, push notification, SMS text message, phone call, email, or any other suitable means of transmitting information.

In some embodiments, the computer-implemented method further includes sharing the acquired signal or the extracted parameters of interest with a contact such as a healthcare provider or birthing specialist for review.

In some embodiments, the method further includes performing an action based on the labor status. For example, in some embodiments, the method includes contacting a service provider to request services if the labor status is positive. Such services may include, but are not limited to, ride-sharing, taxi, childcare, pet-sitting, or other services a woman in labor may need to coordinate.

The disclosed embodiments are susceptible to various modifications and alternative forms, and specific examples thereof have been shown by way of example in the drawings and are herein described in detail. It should be understood, however, that the disclosed embodiments are not to be limited to the particular forms or methods disclosed, but to the contrary, the disclosed embodiments are to cover all modifications, equivalents, and alternatives.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processor in the sensor module and/or computing device. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

As used in the description and claims, the singular form "a", "an" and "the" include both singular and plural references unless the context clearly dictates otherwise. For example, the term "electrode" may include, and is contemplated to include, a plurality of electrodes. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for identifying a labor state in a pregnant female, the system comprising:
    a patch coupled to an abdominal region of the pregnant female;
    at least one physiological sensor coupled to the patch or integrated into the patch;
    a processor communicatively coupled to the at least one physiological sensor; and
    a computer-readable medium having non-transitory, processor-executable instructions stored thereon, wherein execution of the instructions causes the processor to perform a method comprising:
        receiving an input indicating a gestational age of a pregnancy;
        receiving context data pertaining to activities associated with the pregnant female;
        acquiring two or more physiological signals from the at least one physiological sensor, wherein the two or more physiological signals include a maternal heart rate signal and one or more of: an electrohysterography (EHG) signal, a uterine electromyogram (UEMG) signal, a contraction signal, a force of contraction signal, and a frequency of contraction signal;
        processing the two or more physiological signals to identify and extract parameters of interest; and
        determining whether one or more of the parameters of interest are indicative of a labor state associated with one or more predefined contraction patterns, the determining including:
            generating, based on the context data and the maternal heart rate signal, an estimation for a maternal stress level associated with the pregnant female;
            feeding the parameters of interest into a machine learning model trained to identify the one or more of the predefined contraction patterns, wherein the machine learning model is configured to:
                determine a first labor probability based on at least one of the parameters of interest,
                determine a second labor probability based on at least one of the parameters of interest and the gestational age of the pregnancy, and
                classify the labor state of the pregnant female based on the first labor probability, the second labor probability, and the predefined contraction patterns; and
            determining a correlation between the estimation of the maternal stress level and the classified labor state; and
        generating, based on the correlation, a recommendation for reducing the maternal stress level.

2. The system of claim 1, wherein the machine learning model is further configured to:
    determine whether the first labor probability is greater than a baseline,
    determine whether the second probability is greater than one or more of: a first threshold and a second threshold, and
    when the first labor probability is greater than the baseline and the second labor probability is greater than one or both of the first threshold and the second threshold, outputting an indication of a labor status of the pregnant female.

3. The system of claim 2, wherein the method performed by the processor further comprises generating an alert based on the indication of the labor status of the pregnant female.

4. The system of claim 2, wherein the baseline comprises a personalized baseline, and wherein determining the personalized baseline comprises:
    tracking the parameter of interest over time;
    determining a value of the parameter of interest over a period of time; and
    calculating a personalized baseline based on the determined value.

5. The system of claim 4, wherein the method performed by the processor further comprises comparing the parameter of interest to the personalized baseline to identify a deviation from the personalized baseline, and determining whether the deviation is indicative of the labor state.

6. The system of claim 5, wherein the deviation is indicative of the labor state when the deviation is n standard deviations greater than the personalized baseline.

7. The system of claim 5, wherein the deviation is further analyzed using community data stored in a database, the community data comprising one or more of: recorded trends, rules, correlations, and observations generated from tracking, aggregating, and analyzing parameters from a plurality of users.

8. The system of claim 1, wherein the parameters of interest comprise physiological parameters and behavioral parameters.

9. The system of claim 1, wherein the machine learning models comprises one or more of a generalized linear model, a decision tree, a support vector machine, a k-nearest neighbor, a neural network, a deep neural network, a random forest, and a hierarchical model.

10. The system of claim 1, wherein the at least one physiological sensor comprises a measurement electrode and reference electrode.

11. The system of claim 1, wherein the at least one physiological sensor comprises one or more physiological sensors configured to measure one or more of the electrohysterography signal, the maternal heart rate signal, the contraction signal, the force of contraction signal, and the frequency of contraction signal.

12. The system of claim 1, wherein the parameter of interest comprises one or more of a maternal heart rate metric, a maternal heart rate variability metric, a range of an electrohysterography signal, a power of an electrohysterography signal in a specific frequency band, a frequency feature of an electrohysterography signal, and a time-frequency feature of an electrohysterography signal.

13. The system of claim 1, wherein the patch comprises a portable sensor module coupled to the patch or integrated into the patch, wherein the sensor module comprises the at least one physiological sensor, the processor, and the computer-readable medium and further comprises an electronic circuit and a wireless antenna, and wherein the sensor module is in wireless communication with a mobile computing device.

14. The system of claim 1, wherein the method performed by the processor further comprises determining a degree of certainty around one or more of the first labor probability and the second labor probability.

15. The system of claim 1, wherein the method performed by the processor further comprises determining an estimate of time until the pregnant female enters the labor state.

16. The system of claim 1, wherein the input further includes one or more of: clinical data, demographic information, activity, movement patterns, and behavioral parameters.

17. The system of claim 1, wherein the predefined contraction patterns comprise regular contractions, contractions increasing in intensity and frequency over time, periodic changes in maternal heart rate associated with contractions, periodic changes in belly shape or deformation, and decreased maternal heart rate variability over time.

18. The system of claim 1, wherein:
the parameters of interest comprise a plurality of UEMG markers; and
the classifying comprises classifying the plurality of UEMG markers into contraction types, wherein the plurality of UEMG markers comprise a spatial propagation feature including a spatial distribution of a firing of one or more uterine contractile cells of the pregnant female.

19. The system of claim 1, wherein the two or more physiological signals are acquired and processed for a plurality of time periods, and wherein the method performed by the processor further comprises:
determining, for a baseline time period in the plurality of time periods, a first amount in which the first labor probability deviates from a predefined threshold;
determining, for one or more of the plurality of time periods occurring after the baseline time period, a second amount in which a first labor probability for the one or more of the plurality of time periods deviates from the predefined threshold; and
updating, based on the first amount and the second amount, the machine learning model to adjust model sensitivity, the adjusting including increasing or decreasing the predefined threshold to respectively increase or decrease model sensitivity during use of the model for time periods after the plurality of time periods.

20. A computer-implemented method for identifying a labor state in a pregnant female, comprising:
receiving, using a processor, an input indicating a gestational age of a pregnancy;
receiving context data pertaining to activities associated with the pregnant female;
acquiring two or more physiological signals from at least one physiological sensor coupled to or integrated into a patch coupled to an abdominal region of the pregnant female, wherein the two or more physiological signals include a maternal heart rate signal and one or more of: an electrohysterography signal, a contraction signal, a force of contraction signal, and a frequency of contraction signal;
processing, using the processor, the two or more physiological signals to identify and extract parameters of interest; and
determining whether one or more of the parameters of interest are indicative of a labor state associated with one or more predefined contraction patterns, the determining including:
generating, based on the context data and the maternal heart rate signal, an estimation for a maternal stress level associated with the pregnant female;
feeding, using the processor, the parameters of interest into a machine learning model trained to identify the one or more of the predefined contraction patterns, wherein the machine learning model is configured to:
determine a first labor probability based on at least one of the parameters of interest,
determine a second labor probability based on at least one of the parameters of interest and the gestational age of the pregnancy, and
classify the labor state of the pregnant female based on the first labor probability, the second labor probability, and the predefined contraction patterns; and
determining a correlation between the estimation of the maternal stress level and the classified labor state; and
generating, based on the correlation, a recommendation for reducing the maternal stress level.

* * * * *